(12) United States Patent
Staples et al.

(10) Patent No.: US 11,605,444 B2
(45) Date of Patent: Mar. 14, 2023

(54) SYSTEMS AND METHODS FOR LEVERAGING RELATEDNESS IN GENOMIC DATA ANALYSIS

(71) Applicant: Regeneron Pharmaceuticals, Inc., Tarrytown, NY (US)

(72) Inventors: Jeffrey Staples, Tarrytown, NY (US); Lukas Habegger, Tarrytown, NY (US); Jeffrey Reid, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1220 days.

(21) Appl. No.: 16/124,702

(22) Filed: Sep. 7, 2018

(65) Prior Publication Data

US 2019/0205502 A1 Jul. 4, 2019

Related U.S. Application Data

(60) Provisional application No. 62/555,597, filed on Sep. 7, 2017.

(51) Int. Cl.
| | |
|---|---|
| *G16B 20/00* | (2019.01) |
| *G16H 70/60* | (2018.01) |
| *G16H 50/50* | (2018.01) |
| *G16H 10/60* | (2018.01) |
| *G06F 16/28* | (2019.01) |
| *G16B 40/00* | (2019.01) |
| *G16B 20/20* | (2019.01) |
| *G16B 5/00* | (2019.01) |
| *G16B 30/00* | (2019.01) |

(52) U.S. Cl.
CPC ........... *G16B 20/00* (2019.02); *G06F 16/288* (2019.01); *G16B 5/00* (2019.02); *G16B 20/20* (2019.02); *G16B 30/00* (2019.02); *G16B 40/00* (2019.02); *G16H 10/60* (2018.01); *G16H 50/50* (2018.01); *G16H 70/60* (2018.01)

(58) Field of Classification Search
CPC .......... G16B 20/00; G16B 5/00; G16B 20/20; G16B 40/00; G16B 30/00; G16H 70/60; G16H 50/50; G16H 10/60; G06F 16/288
See application file for complete search history.

(56) References Cited

U.S. PATENT DOCUMENTS

2015/0094961 A1 4/2015 Ghaffarzadeh
2015/0211054 A1 7/2015 Kostem et al.

FOREIGN PATENT DOCUMENTS

WO WO2013/067001 A1 5/2013

OTHER PUBLICATIONS

Ryan Tewhey et al., "The Importance of Phase Information for Human Genomics," Nature Review Genetics, vol. 12, No. 3, Feb. 8, 2011, pp. 215-223.
Richard A. Morton et al., "Mate Choice and the Origin of Menopause," PLOS Computational Biology, vol. 9, No. 6, Jun. 13, 2013, p. e1003092.
International Search Report, PCT Application No. PCT/US2018/049967, Application Filing Date Sep. 7, 2018, dated Nov. 28, 2018.
International Search Report, PCT Application No. PCT/US2018/049960, Application Filing Date Sep. 7, 2018, dated Dec. 5, 2018.
Kong A. et al., Detection of sharing by descent, long-range phasing and haplotype imputation. Nat Genet, Aug. 17, 2008, vol. 40, No. 9, pp. 1068-1075.
Loh P.-R. et al., Reference-based phasing using the Haplotype Reference Consortium panel. Nat Genet, Oct. 3, 2016, vol. 48, No. 11, pp. 1443-1448.
Browning S.R. and Browning B.L., Haplotype phasing: existing methods and new developments. Nat Rev Genet, Sep. 16, 2011, vol. 12, pp. 703-714.
Staples J. et al., Profiling and Leveraging Relatedness in a Precision Medicine Cohort of 92,455 Exomes. Am J Hum Genet, May 3, 2018, vol. 102, No. 5, pp. 874-889.
Singapore Search Report, Application No. 11202001715Y, Date of Completion Oct. 2, 2021.

*Primary Examiner* — Jerry Lin
(74) *Attorney, Agent, or Firm* — Kramer Levin Naftalis & Frankel LLP

(57) ABSTRACT

Methods, non-transitory computer-implemented methods and systems for identifying compound heterozygous mutations (CHMs) and de novo mutations (DNMs) in populations are provided. Also provided are methods for phasing genetic variants in a population by leveraging the population's relatedness. Further provided is a prediction model of relatedness in a human population.

20 Claims, 57 Drawing Sheets
(31 of 57 Drawing Sheet(s) Filed in Color)

Figure 2

11 Identify variants in DNA sequence samples from a plurality of human subjects

12 Establish an ancestral superclass designation for subjects based on identified variants

13 Generate first identity-by-descent estimates of subjects within an ancestral superclass

14 Generate second identity-by-descent estimates of subjects independent from subjects' ancestral superclass

15 Cluster subjects into primary first-degree family networks based on one or more of the second identity-by-descent estimates

16 Generate third identity-by-descent estimates of subjects within a primary first-degree family network

17 Merge first and third identity-by-descent estimates to obtain merged identity-by-descent estimates

18 Construct secondary first-degree family networks based on merged identity-by-descent estimates

19 Phase variants in samples according to population-allele frequencies

20 Classify a phased variant as a potential CHM based on the presence of two or more variants in the same subject and gene

21 Phase a potential CHM as cis or trans with another variant in the same subject and gene, and then classifying the potential CHM phased as trans as CHM

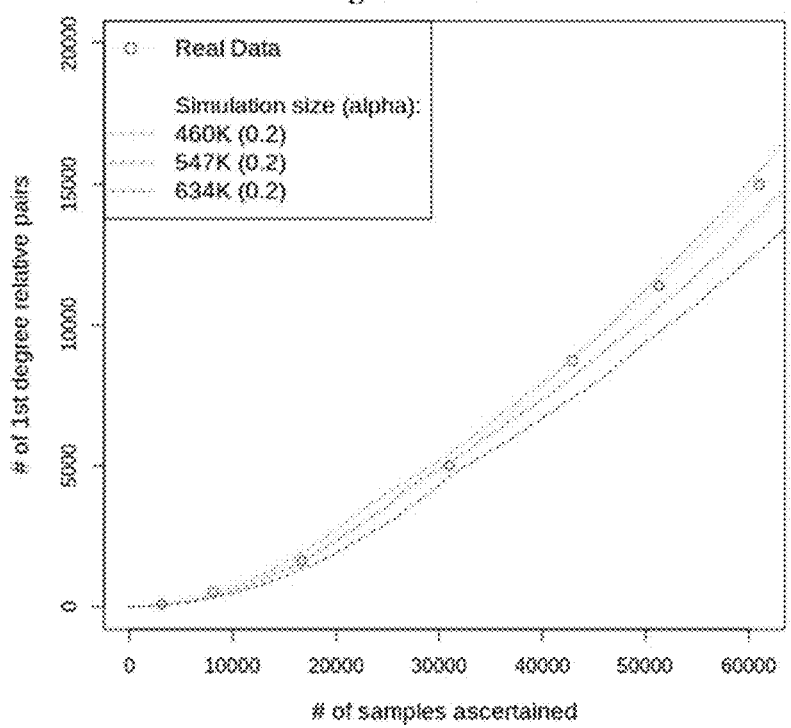

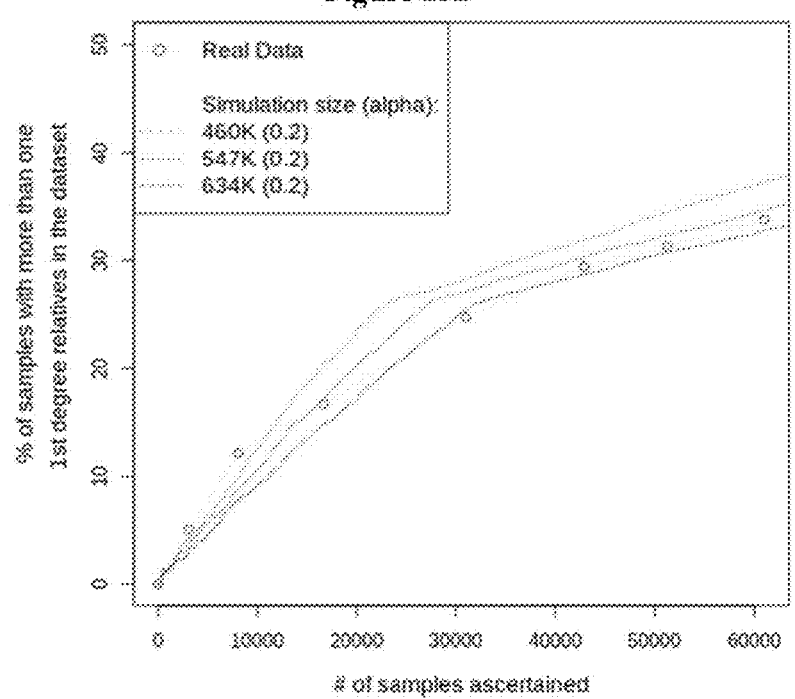

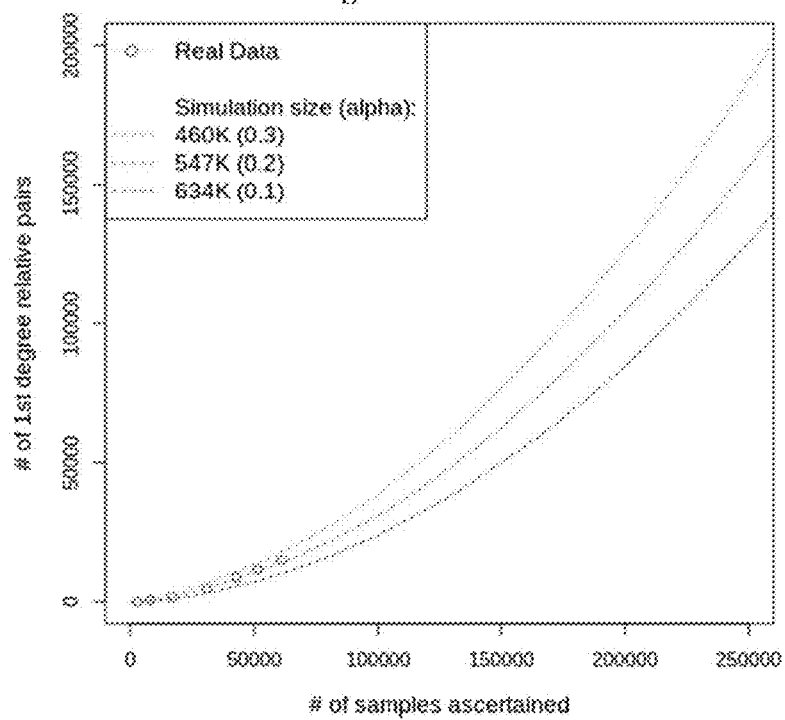

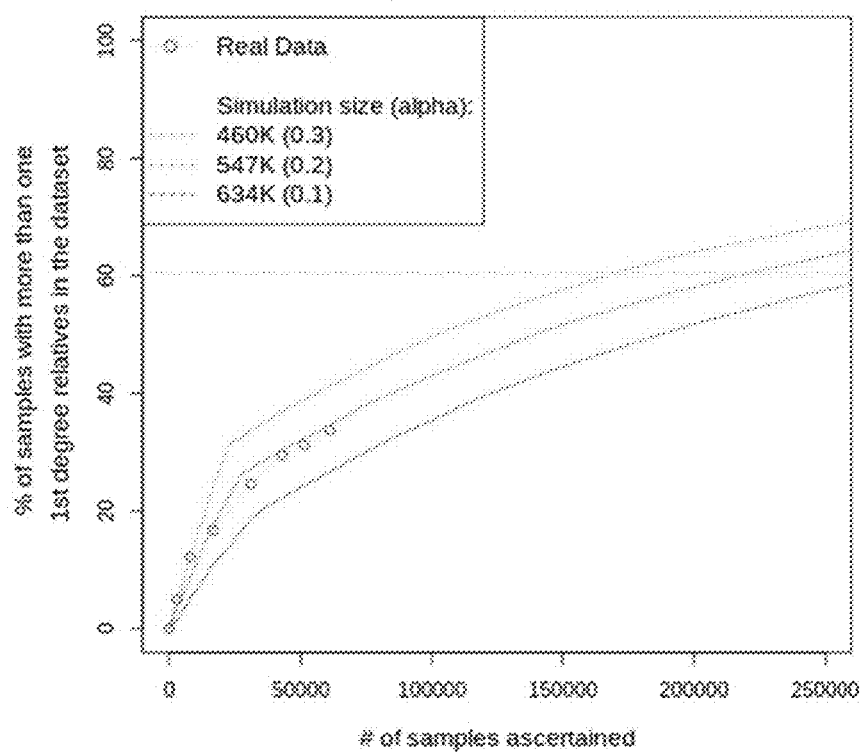

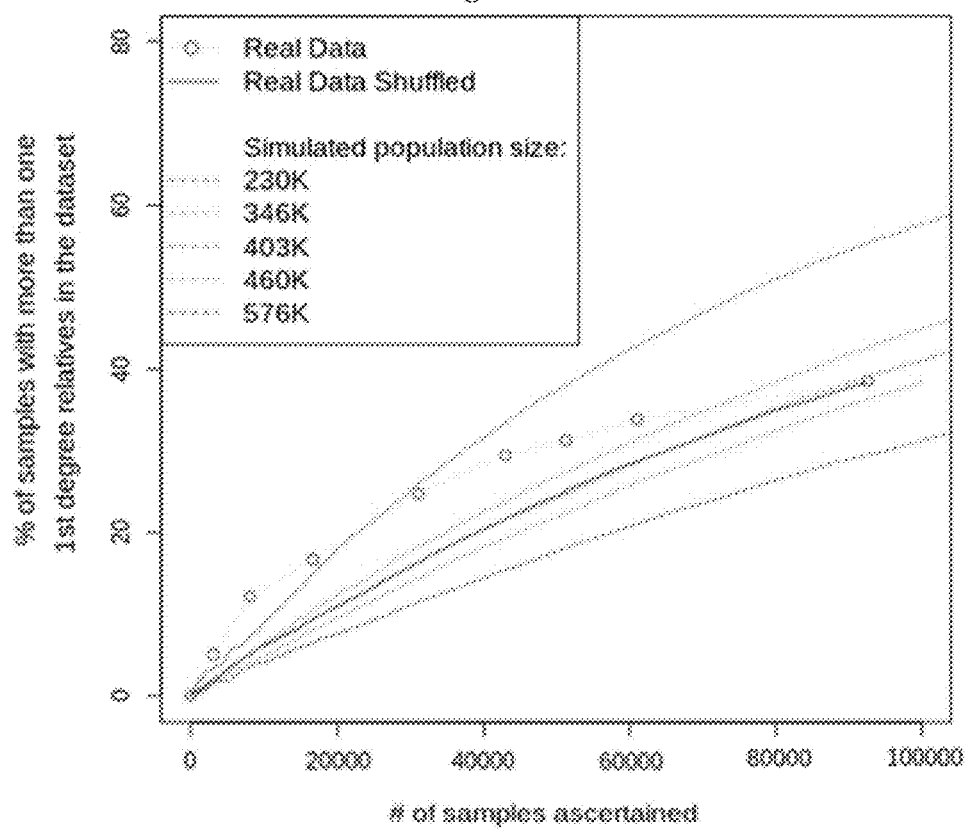

Figure 21A
Figure 21B
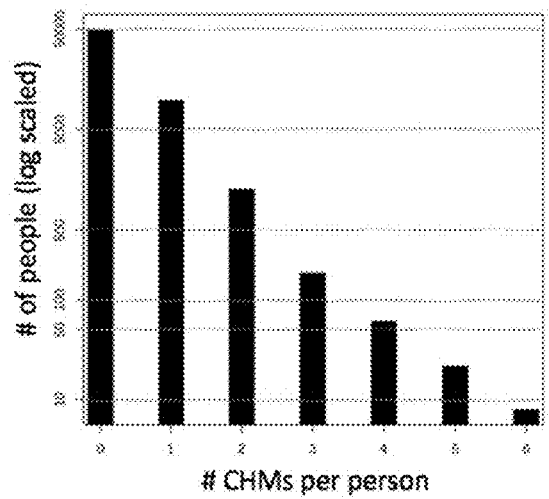
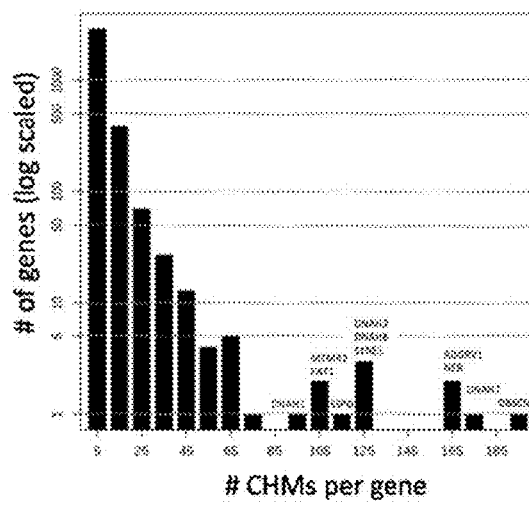
Figure 21C
Figure 21D

*ACTA2* (p.Arg118Gln): Aortic aneurysms

*KCNH2* (p.Pro1093Leu): Long QT syndrome

*RET* (p.Ser891Ala): Thyroid cancer

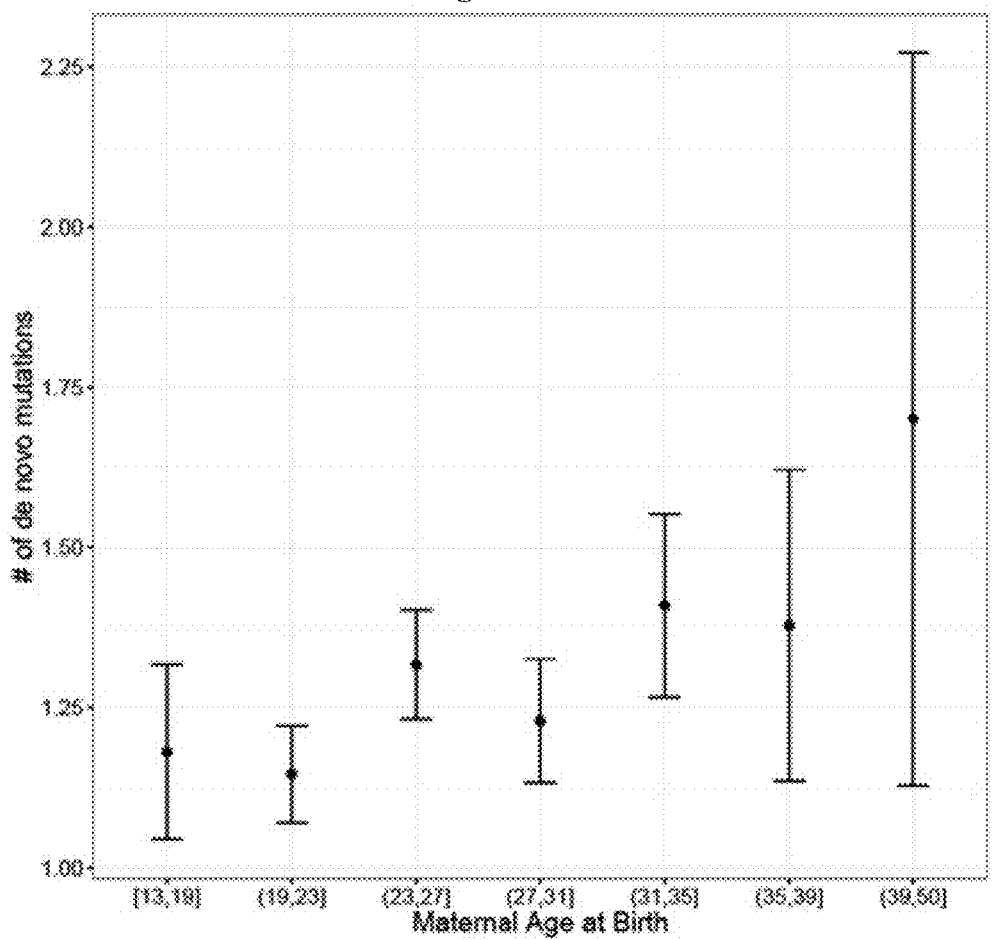

SYSTEMS AND METHODS FOR LEVERAGING RELATEDNESS IN GENOMIC DATA ANALYSIS

CROSS-REFERENCE TO RELATED APPLICATIONS

This application claims the benefit of U.S. Provisional Patent Application No. 62/555,597, filed on Sep. 7, 2017, the content of which is hereby incorporated by reference in its entirety. In addition, application entitled "Systems and Methods for a Prediction Model of Relatedness in a Human Population" filed on Sep. 7, 2018 is also incorporated by reference in its entirety.

FIELD

The disclosure relates generally to methods and systems for the analysis of genomic data and using relatedness in a large population cohort to connect rare genetic variations to disease and disease susceptibility. More particularly, the disclosure relates to systems and methods for establishing identity by descent, and for phasing genetic variants as compound heterozygous mutations or de novo mutations.

BACKGROUND

Human disease conditions are not only caused and influenced by environmental factors, but also by genetic factors. An understanding of genetic variation in human populations is therefore important for an understanding of the etiology and progression of human diseases, as well as for the identification of novel drug targets for the treatment of these diseases.

Genetic studies of health care populations are particularly useful in this regard because of the availability of extensive health care data, which simplify the research of how genetic variants contribute to disease conditions in humans. In the past, such studies were usually based on genome-wide genetic linkage analyses to map disease loci, which, once identified, could then be further analyzed in detail on the molecular level.

Over the last few years, the widespread availability of high-throughput DNA sequencing technologies has allowed the parallel sequencing of the genomes of hundreds of thousands of humans. In theory, these data represent a powerful source of information that can be used to decipher the genetic underpinnings of human diseases. However, these ever growing datasets have required constant innovation of bioinformatics tools and analysis pipelines to continue handling these extremely large datasets efficiently. Furthermore, the utility of relatedness and family structure in these large datasets and the extent as to which it can be leveraged for the identification and characterization of variants has not been fully recognized and exploited.

There remains a need for improved bioinformatics tools for the analysis of large scale genomic data. The disclosure addresses this need.

SUMMARY

In one aspect, the disclosure provides methods for phasing genetic variants in a population by leveraging the population's relatedness including: removing low-quality sequence variants from a dataset of nucleic acid sequence samples obtained from a plurality of human subjects, establishing an ancestral superclass designation for each of one or more of the samples, removing low-quality samples from the dataset, generating first identity-by-descent estimates of subjects within an ancestral superclass, generating second identity-by-descent estimates of subjects independent from subjects' ancestral superclass, clustering subjects into primary first-degree family networks based on one or more of the second identity-by-descent estimates, generating third identity-by-descent estimates of subjects within a primary first-degree family network, merging first and third identity-by-descent estimates to obtain merged identity-by-descent estimates, constructing secondary first-degree family networks of samples based on merged identity-by-descent estimates, and phasing variants in accordance with merged identity-by-descent estimates and secondary first-degree family networks as being or not being a compound heterozygous mutation (CHM), or identifying variants in accordance with merged identity-by-descent estimates and secondary first-degree family networks as a de novo mutation (DNM).

In some exemplary embodiments, merging first and third identity-by-descent estimates includes augmenting the first identity-by-descent estimates with pairwise identity-by-descent estimates unique to the third identity-by-descent estimates.

In some exemplary embodiments, phasing variants as a compound heterozygous mutation (CHM) includes: (1) phasing variants according to population allele frequencies, (2) removing variants outside of Hardy-Weinberg equilibrium (HWE) or within 10 base pairs of another variant in the same sample or both; and removing single nucleotide polymorphisms (SNPs) with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof, (3) selecting remaining variants as potential compound heterozygous mutations (pCHMs) where there are one or more pairs of variants in the same sample and in the same gene, and (4) phasing pCHMs as either cis or trans pCHMs, and then classifying the pCHM phased as trans pCHM as CHM.

In some exemplary embodiments, phasing variants as a compound heterozygous mutation comprises: removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof.

In some exemplary embodiments, the method further includes: (1) scoring CHMs according to functional effect priority, and (2) selecting CHMs having the highest functional effect priority score per gene per sample, such that when the human has more than one CHM in the same gene, the CHM most likely to result in protein function inhibition is identified.

In some exemplary embodiments, phasing variants as a de novo mutation includes: (1) identifying variants in samples in secondary first-degree family networks and trios thereof, (2) assigning genotype likelihood scores to variants in parent samples and corresponding child sample in a trio and calculating a probability that the variant is a de novo mutation, and identifying the variant as a probable de novo mutation when the calculated probability is statistically significant, (3) identifying a variant in a child sample in a trio and identifying the variant as a probable de novo mutation when the variant is not present in either parent sample in the trio, (4) filtering probable de novo mutations identified by removing probable de novo mutations having a genotype quality (GQ) annotation in the child sample of less than about 35, or having an alternate allele count (AC) of 10 or greater across the samples from the plurality of human subjects, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof, and (5) combining filtered probable de novo mutations identified, thereby forming a probable de novo mutation dataset.

In some exemplary embodiments, the method further includes: classifying a probable de novo mutation in the probable de novo mutation dataset as a moderate confidence de novo mutation when the probable de novo mutation has an allele balance of about 0.15 or greater in the child sample and about 0.02 or less in each parent sample, and does not have a mapping quality of less than about 40, and does not have a quality by depth (QD) value of less than about 2, and has MAC of less than about 20 across the samples, and has about 3 soft-clipped reads or less at the variant site in the carrier of the probable de novo mutation, and is not an INDEL with a mono-polymer run of more than about 4.

In some exemplary embodiments, the method further includes: classifying a moderate confidence de novo mutation as a high confidence de novo mutation when the moderate confidence de novo mutation has a genotype quality annotation in the parent sample of about 90 or greater, and has a read depth of about 10 or greater in each parent sample, and has an alternate read depth of about 7 or greater in the child sample, and has QD greater than about 3 for SNPs, and has QD greater than about 5 for INDELs.

In one aspect, the disclosure provides a method for identifying compound heterozygous mutations (CHMs) in a population, including: identifying variants in DNA sequence samples from a plurality of human subjects; establishing an ancestral superclass designation for subjects based on identified variants; generating first identity-by-descent estimates of subjects within an ancestral superclass; generating second identity-by-descent estimates of subjects independent from subjects' ancestral superclass; clustering subjects into primary first-degree family networks based on one or more of the second identity-by-descent estimates; generating third identity-by-descent estimates of subjects within a primary first-degree family network; merging first and third identity-by-descent estimates to obtain merged identity-by-descent estimates; constructing secondary first-degree family networks based on merged identity-by-descent estimates; phasing variants in samples according to population-allele frequencies; classifying a phased variant as a potential CHM based on the presence of two or more variants in the same subject and gene; and phasing a potential CHM as cis or trans with another variant in the same subject and gene, and then classifying the potential CHM phased as trans as CHM.

In some exemplary embodiments, the method further includes filtering identified variants before ancestral superclass designations for subjects are established.

In some exemplary embodiments, the method further includes filtering identified variants before first and second identity-by-descent estimates of subjects are generated.

In some exemplary embodiments, filtering variants includes removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof.

In some exemplary embodiments, the method further includes removing low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates includes augmenting the first identity-by-descent estimates with pairwise identity-by-descent estimates unique to the third identity-by-descent estimates.

In some exemplary embodiments, identity-by-descent estimates comprise genome-wide calculations of IBD 0, 1, and 2 values among sample pairs.

In some exemplary embodiments, the method further includes filtering variants after variants have been phased according to population-allele frequencies.

In some exemplary embodiments, filtering variants phased according to population-allele frequencies includes removing variants outside of Hardy-Weinberg equilibrium (HWE) or within 10 base pairs of another variant in the same sample or both; and removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof.

In some exemplary embodiments, phasing variants according to population-allele frequencies includes dividing DNA sequence samples of human subjects into genomic segments having approximately equal size, substantial segment overlap and break points in intergenic regions.

In some exemplary embodiments, potential CHMs are phased based on trio data, or parent-child data, or full-sibling data, or distant relative data, or a combination thereof; or are phased based on minor allele counts (MAC); or are phased based on population-allele frequencies; or a combination thereof.

In some exemplary embodiments, the method further includes scoring CHMs according to functional effect priority, and selecting CHMs having the highest functional effect priority score per gene per sample, thereby obtaining a collection of medically relevant mutations.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a Kolmogorov-Smirnov (KS) test.

In some exemplary embodiments, filtering variants phased according to population-allele frequencies includes removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof.

In another aspect, the disclosure provides non-transitory computer-implemented methods for identifying compound heterozygous mutations (CHMs) in a population. In general, the non-transitory computer-implemented methods comprise using a data processor of a computing device for identifying variants in DNA sequence samples from a plurality of human subjects; using the data processor for establishing an ancestral superclass designation for subjects based on identified variants; using the data processor for generating first identity-by-descent estimates of subjects within an ancestral superclass; using the data processor for generating second identity-by-descent estimates of subjects independent from subjects' ancestral superclass; using the data processor for clustering subjects into primary first-degree family networks based on one or more of the second identity-by-descent estimates; using the data processor for generating third identity-by-descent estimates of subjects within a primary first-degree family network; using the data processor for merging first and third identity-by-descent estimates to obtain merged identity-by-descent estimates; using the data processor for constructing secondary first-degree family networks based on merged identity-by-descent estimates; using the data processor for phasing variants in samples according to population-allele frequencies; using the data processor for classifying a phased variant as a potential CHM based on the presence of two or more variants in the same subject and gene; and using the data processor for phasing a potential CHM as cis or trans with another variant in the same subject and gene, and then classifying the potential CHM phased as trans as CHM.

In some exemplary embodiments, the non-transitory computer-implemented method further includes using the data processor to filter identified variants before ancestral superclass designations for subjects are established.

In some exemplary embodiments, the non-transitory computer-implemented method further includes using the data processor to filter identified variants before second identity-by-descent estimates of subjects are generated.

In some exemplary embodiments, filtering variants includes removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof.

In some exemplary embodiments, the non-transitory computer-implemented method further includes using the data processor to remove low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates includes augmenting the first identity-by-descent estimates with pairwise identity-by-descent estimates unique to the third identity-by-descent estimates.

In some exemplary embodiments, identity-by-descent estimates comprise genome-wide calculations of IBD 0, 1, and 2 values among sample pairs.

In some exemplary embodiments, the non-transitory computer-implemented method further includes using the data processor to filter variants after variants have been phased according to population-allele frequencies.

In some exemplary embodiments, filtering variants phased according to population-allele frequencies includes removing variants outside of Hardy-Weinberg equilibrium or within 10 base pairs of another variant in the same sample or both; and removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof.

In some exemplary embodiments, phasing variants according to population-allele frequencies includes dividing DNA sequence samples of human subjects into genomic segments having approximately equal size, substantial segment overlap and break points in intergenic regions.

In some exemplary embodiments, potential CHMs are phased based on trio data, or parent-child data, or full-sibling data, or distant relative data, or a combination thereof or are phased based on minor allele counts (MAC); or are phased based on population-allele frequencies; or a combination thereof.

In some exemplary embodiments, the non-transitory computer-implemented method further includes using the data processor to score CHMs according to functional effect priority, and select CHMs having the highest functional effect priority score per gene per sample, thereby obtaining a collection of medically relevant mutations.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a KS test.

In some exemplary embodiments, filtering variants phased according to population-allele frequencies includes removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof.

In another aspect, the disclosure provides systems to implement the methods and non-transitory computer-implemented methods. The systems generally include a data processor; a memory coupled with the data processor; and a program stored in the memory, the program including instructions for: identifying variants in DNA sequence samples from a plurality of human subjects; establishing an ancestral superclass designation for subjects based on identified variants; generating first identity-by-descent estimates of subjects within an ancestral superclass; generating second identity-by-descent estimates of subjects independent from subjects' ancestral superclass; clustering subjects into primary first-degree family networks based on one or more of the second identity-by-descent estimates; generating third identity-by-descent estimates of subjects within a primary first-degree family network; merging first and third identityby-descent estimates to obtain merged identity-by-descent estimates; constructing secondary first-degree family networks based on merged identity-by-descent estimates; phasing variants in samples according to population-allele frequencies; classifying a phased variant as a potential CHM based on the presence of two or more variants in the same subject and gene; and phasing a potential CHM as cis or trans with another variant in the same subject and gene, and then classifying the potential CHM phased as trans as CHM.

In some exemplary embodiments, the program includes instructions for filtering identified variants before ancestral superclass designations for subjects are established.

In some exemplary embodiments, the program includes instructions for filtering identified variants before first and second identity-by-descent estimates of subjects are generated.

In some exemplary embodiments, filtering variants comprises removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof.

In some exemplary embodiments, the program includes instructions for removing low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates comprises augmenting the first identity-by-descent estimates with pairwise identity-by-descent estimates unique to the third identity-by-descent estimates.

In some exemplary embodiments, identity-by-descent estimates include genome-wide calculations of IBD 0, 1, and 2 values among sample pairs.

In some exemplary embodiments, the program includes instructions for filtering variants after variants have been phased according to population-allele frequencies.

In some exemplary embodiments, filtering variants phased according to population-allele frequencies includes removing variants outside of Hardy-Weinberg equilibrium (HWE) or within 10 base pairs of another variant in the same sample or both; and removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof.

In some exemplary embodiments, phasing variants according to population-allele frequencies comprises dividing DNA sequence samples of human subjects into genomic segments having approximately equal size, substantial segment overlap and break points in intergenic regions.

In some exemplary embodiments, potential CHMs are phased based on trio data, or parent-child data, or full-sibling data, or distant relative data, or a combination thereof; or are phased as based on minor allele counts (MAC); or are phased based on population-allele frequencies; or a combination thereof.

In some exemplary embodiments, the program includes instructions for scoring CHMs according to functional effect priority, and selecting CHMs having the highest functional effect priority score per gene per sample, thereby obtaining a collection of medically relevant mutations.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a KS test.

In some exemplary embodiments, filtering variants phased according to population-allele frequencies includes removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof.

In another aspect, the disclosure provides methods for identifying de novo mutations (DNMs) in a population. In general, the methods comprise identifying variants in DNA sequence samples from a plurality of human subjects; establishing an ancestral superclass designation for subjects based on identified variants; generating first identity-by-descent estimates of subjects within an ancestral superclass; generating second identity-by-descent estimates of subjects independent from subjects' ancestral superclass; clustering subjects into primary first-degree family networks based on one or more of the second identity-by-descent estimates; generating third identity-by-descent estimates of subjects within a primary first-degree family network; merging first and third identity-by-descent estimates to obtain merged identity-by-descent estimates; constructing nuclear families based on merged identity-by-descent estimates; identifying variants in nuclear families; assigning a genotype likelihood score to a variant in samples from each parent and child in a trio in a constructed nuclear family and calculating a probability that the variant is a de novo mutation, and independently naively identifying a variant in a child sample that is not present in either parent sample in a trio and calculating a probability that the variant is a de novo mutation, and then combining both probabilities, thereby forming a dataset of probable de novo mutations.

In some exemplary embodiments, the method further includes filtering identified variants before ancestral superclass designations for subjects are established.

In some exemplary embodiments, the method further includes filtering identified variants before second identity-by-descent estimates of subjects are generated.

In some exemplary embodiments, filtering variants includes removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof.

In some exemplary embodiments, the method further includes removing low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates includes augmenting the first identity-by-descent estimates with pairwise identity-by-descent estimates unique to the third identity-by-descent estimates.

In some exemplary embodiments, identity-by-descent estimates include genome-wide calculations of IBD 0, 1, and 2 values among sample pairs.

In some exemplary embodiments, the genotype likelihood score is based on DNA sequence samples from a plurality of human subjects in a plurality of nuclear families.

In some exemplary embodiments, the method further includes filtering variants after probabilities have been calculated that variants are de novo mutations based on genotype likelihood scores.

In some exemplary embodiments, the method further includes filtering variants after probabilities have been calculated that variants are de novo mutations based on naively identifying a variant in a child sample that is not present in either parent sample.

In some exemplary embodiments, filtering variants includes removing variants having a genotype quality (GQ) annotation in the child sample of less than about 35, or having an alternate allele count (AC) of 10 or greater among the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof.

In some exemplary embodiments, the method further includes annotating variants with quality control metrics.

In some exemplary embodiments, the method further includes filtering variants based on sample BAM file data after probable de novo mutations have been identified based on naively identifying a variant in a child sample that is not present in either parent sample.

In some exemplary embodiments, the method further includes classifying a probable de novo mutation as a moderate confidence de novo mutation when the probable de novo mutation has an allele balance of about 0.15 or greater in the child sample.

In some exemplary embodiments, the method further includes classifying a probable de novo mutation as a moderate confidence de novo mutation when the probable de novo mutation has an allele balance of about 0.02 or less in each parent sample.

In some exemplary embodiments, the method further includes classifying a probable de novo mutation as a moderate confidence de novo mutation when the probable de novo mutation does not have a mapping quality of less than about 40.

In some exemplary embodiments, the method further includes classifying a probable de novo mutation as a moderate confidence de novo mutation when the probable de novo mutation does not have a quality by depth (QD) value of less than about 2.

In some exemplary embodiments, the method further includes classifying a probable de novo mutation as a moderate confidence de novo mutation when the probable de novo mutation has MAC of less than about 20 across the samples.

In some exemplary embodiments, the method further includes classifying a probable de novo mutation as a moderate confidence de novo mutation when the probable de novo mutation has about 3 soft-clipped reads or less at the variant site in the carrier of the probable de novo mutation.

In some exemplary embodiments, the method further includes classifying a probable de novo mutation as a moderate confidence de novo mutation when the probable de novo mutation is not an INDEL with a mono-polymer run of more than about 4.

In some exemplary embodiments, the method further includes classifying a probable de novo mutation as a moderate confidence de novo mutation when the probable de novo mutation has an allele balance (AB) of about 0.15 or greater in the child sample and about 0.02 or less in each parent sample, and does not have a mapping quality (MQ) of less than about 40, and does not have a quality by depth (QD) value of less than about 2, and has minor allele count (MAC) of less than about 20 across the samples, and has about 3 soft-clipped reads or less at the variant site in the carrier of the probable de novo mutation, and is not an INDEL with a mono-polymer run of more than about 4.

In some exemplary embodiments, the method further includes classifying a moderate confidence de novo mutation as a high confidence de novo mutation when the moderate confidence de novo mutation has a genotype quality (GQ) annotation in the parent sample of about 90 or greater, and has a read depth (DP) of about 10 or greater in each parent sample, and has an alternate DP of about 7 or greater in the child sample, and has QD greater than about 3 for SNPs, and has QD greater than about 5 for INDELs.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a KS test.

In another aspect, the disclosure provides non-transitory computer-implemented methods for identifying de novo mutations (DNMs) in a population. In general, the non-transitory computer-implemented methods comprise using a data processor of a computing device for identifying variants in DNA sequence samples from a plurality of human subjects; using a data processor for establishing an ancestral superclass designation for subjects based on identified variants; using a data processor for generating first identity-by-descent estimates of subjects within an ancestral superclass; using a data processor for generating second identity-by-descent estimates of subjects independent from subjects' ancestral superclass; using a data processor for clustering subjects into primary first-degree family networks based on one or more of the second identity-by-descent estimates; using a data processor for generating third identity-by-descent estimates of subjects within a primary first-degree family network; using a data processor for merging first and third identity-by-descent estimates to obtain merged identity-by-descent estimates; using a data processor for constructing nuclear families based on merged identity-by-descent estimates; using a data processor for identifying variants in nuclear families; using a data processor for assigning a genotype likelihood score to a variant in samples from each parent and child in a trio in a constructed nuclear family and calculating a probability that the variant is a de novo mutation, and independently naively identifying a variant in a child sample that is not present in either parent sample in a trio and calculating a probability that the variant is a de novo mutation, and then combining both probabilities, thereby forming a dataset of probable de novo mutations.

In some exemplary embodiments, the non-transitory computer-implemented method further includes using the data processor to filter identified variants before ancestral superclass designations for subjects are established.

In some exemplary embodiments, the non-transitory computer-implemented method further includes using the data processor to filter identified variants before second identity-by-descent estimates of subjects are generated.

In some exemplary embodiments, filtering variants includes removing variants having alternate allele frequency greater than about 10% across the samples from the plurality of human subjects, or variants violating Hardy-Weinberg equilibrium with a p-value >about $10^{-6}$, or variants having missing calls in >about 5% of the samples from the plurality of human subjects, or a combination thereof.

In some exemplary embodiments, the non-transitory computer-implemented method further includes using the data processor to remove low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates includes augmenting the first identity-by-descent estimates with pairwise identity-by-descent estimates unique to the third identity-by-descent estimates.

In some exemplary embodiments, identity-by-descent estimates include genome-wide calculations of IBD 0, 1, and 2 values among sample pairs.

In some exemplary embodiments, the genotype likelihood score is based on DNA sequence samples from a plurality of human subjects in a plurality of nuclear families.

In some exemplary embodiments, the non-transitory computer-implemented method further includes using the data processor to filter variants after probabilities have been calculated that variants are de novo mutations based on genotype likelihood scores.

In some exemplary embodiments, the non-transitory computer-implemented method further includes using the data processor to filter variants after probabilities have been calculated that variants are de novo mutations based on naively identifying a variant in a child sample that is not present in either parent sample.

In some exemplary embodiments, filtering variants includes removing variants having a genotype quality (GQ) annotation in the child sample of less than about 35, or having an alternate allele count (AC) of 10 or greater across the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof.

In some exemplary embodiments, the non-transitory computer-implemented method further includes using the data processor to annotate variants with quality control metrics.

In some exemplary embodiments, the non-transitory computer-implemented method further includes using the data processor to filter variants based on sample BAM file data after probable de novo mutations have been identified based on naively identifying a variant in a child sample that is not present in either parent sample.

In some exemplary embodiments, the non-transitory computer-implemented method further includes using the data processor to classify a probable de novo mutation as a moderate confidence de novo mutation when the probable de novo mutation has an allele balance of about 0.15 or greater in the child sample.

In some exemplary embodiments, the non-transitory computer-implemented method further includes using the data processor to classify a probable de novo mutation as a moderate confidence de novo mutation when the probable de novo mutation has an allele balance of about 0.02 or less in each parent sample.

In some exemplary embodiments, the non-transitory computer-implemented method further includes using the data processor to classify a probable de novo mutation as a moderate confidence de novo mutation when the probable de novo mutation does not have a mapping quality of less than about 40.

In some exemplary embodiments, the non-transitory computer-implemented method further includes using the data processor to classify a probable de novo mutation as a moderate confidence de novo mutation when the probable de novo mutation does not have a quality by depth (QD) value of less than about 2.

In some exemplary embodiments, the non-transitory computer-implemented method further includes using the data processor to classify a probable de novo mutation as a moderate confidence de novo mutation when the probable de novo mutation has MAC of less than about 20 across the samples.

In some exemplary embodiments, the non-transitory computer-implemented method further includes using the data processor to classify a probable de novo mutation as a moderate confidence de novo mutation when the probable de novo mutation has about 3 soft-clipped reads or less at the variant site in the carrier of the probable de novo mutation.

In some exemplary embodiments, the non-transitory computer-implemented method further includes using the data processor to classify a probable de novo mutation as a moderate confidence de novo mutation when the probable de novo mutation is not an INDEL with a mono-polymer run of more than about 4.

In some exemplary embodiments, the non-transitory computer-implemented method further includes using the data processor to classify a probable de novo mutation as a moderate confidence de novo mutation when the probable de novo mutation has an allele balance (AB) of about 0.15 or greater in the child sample and about 0.02 or less in each parent sample, and does not have a mapping quality (MQ) of less than about 40, and does not have a quality by depth (QD) value of less than about 2, and has minor allele count (MAC) of less than about 20 across the samples, and has about 3 soft-clipped reads or less at the variant site in the carrier of the probable de novo mutation, and is not an INDEL with a mono-polymer run of more than about 4.

In some exemplary embodiments, the non-transitory computer-implemented method further includes using the data processor to classify a moderate confidence de novo mutation as a high confidence de novo mutation when the moderate confidence de novo mutation has a genotype quality (GQ) annotation in the parent sample of about 90 or greater, and has a read depth (DP) of about 10 or greater in each parent sample, and has an alternate DP of about 7 or greater in the child sample, and has QD greater than about 3 for SNPs, and has QD greater than about 5 for INDELs.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a KS test.

In another aspect, the disclosure provides systems. The systems may be used, for example, to implement the methods and non-transitory computer-implemented methods. The systems generally include a data processor; a memory coupled with the data processor; and a program stored in the memory, the program including instructions for: identifying variants in DNA sequence samples from a plurality of human subjects; establishing an ancestral superclass designation for subjects based on identified variants; generating first identity-by-descent estimates of subjects within an ancestral superclass; generating second identity-by-descent estimates of subjects independent from subjects' ancestral superclass; clustering subjects into primary first-degree family networks based on one or more of the second identity-by-descent estimates; generating third identity-by-descent estimates of subjects within a primary first-degree family network; merging first and third identity-by-descent estimates to obtain merged identity-by-descent estimates; constructing nuclear families based on merged identity-by-descent estimates; identifying variants in nuclear families; assigning a genotype likelihood score to a variant in samples from each parent and child in a trio in a constructed nuclear family and calculating a probability that the variant is a de novo mutation, and independently naively identifying a variant in a child sample that is not present in either parent sample in a trio and calculating a probability that the variant is a de novo mutation, and then combining both probabilities, thereby forming a dataset of probable de novo mutations.

In some exemplary embodiments, the program includes instructions for filtering identified variants before ancestral superclass designations for subjects are established.

In some exemplary embodiments, the program includes instructions for filtering identified variants before second identity-by-descent estimates of subjects are generated.

In some exemplary embodiments, filtering variants includes removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof.

In some exemplary embodiments, the program includes instructions for removing low-quality samples after identified variants have been filtered.

In some exemplary embodiments, low-quality samples are samples having a D-stat of >0.12 or 20× read coverage of <75%, or both.

In some exemplary embodiments, merging first and third identity-by-descent estimates includes augmenting the first identity-by-descent estimates with pairwise identity-by-descent estimates unique to the third identity-by-descent estimates.

In some exemplary embodiments, identity-by-descent estimates include genome-wide calculations of IBD 0, 1, and 2 values among sample pairs.

In some exemplary embodiments, the genotype likelihood score is based on DNA sequence samples from a plurality of human subjects in a plurality of nuclear families.

In some exemplary embodiments, the program includes instructions for filtering variants after probabilities have been calculated that variants are de novo mutations based on genotype likelihood scores.

In some exemplary embodiments, the program includes instructions for filtering variants after probabilities have been calculated that variants are de novo mutations based on naively identifying a variant in a child sample that is not present in either parent sample.

In some exemplary embodiments, filtering variants includes removing variants having a genotype quality (GQ) annotation in the child sample of less than about 35, or having an alternate allele count (AC) of 10 or greater across the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof.

In some exemplary embodiments, the program includes instructions for annotating variants with quality control metrics.

In some exemplary embodiments, the program includes instructions for filtering variants based on sample BAM file data after probable de novo mutations have been identified based on naively identifying a variant in a child sample that is not present in either parent sample.

In some exemplary embodiments, the program includes instructions for classifying a probable de novo mutation as a moderate confidence de novo mutation when the probable de novo mutation has an allele balance of about 0.15 or greater in the child sample.

In some exemplary embodiments, the program includes instructions for classifying a probable de novo mutation as a moderate confidence de novo mutation when the probable de novo mutation has an allele balance of about 0.02 or less in each parent sample.

In some exemplary embodiments, the program includes instructions for classifying a probable de novo mutation as a moderate confidence de novo mutation when the probable de novo mutation does not have a mapping quality of less than about 40.

In some exemplary embodiments, the program includes instructions for classifying a probable de novo mutation as a moderate confidence de novo mutation when the probable de novo mutation does not have a quality by depth (QD) value of less than about 2.

In some exemplary embodiments, the program includes instructions for classifying a probable de novo mutation as a moderate confidence de novo mutation when the probable de novo mutation has MAC of less than about 20 across the samples.

In some exemplary embodiments, the program includes instructions for classifying a probable de novo mutation as a moderate confidence de novo mutation when the probable de novo mutation has about 3 soft-clipped reads or less at the variant site in the carrier of the probable de novo mutation.

In some exemplary embodiments, the program includes instructions for classifying a probable de novo mutation as a moderate confidence de novo mutation when the probable de novo mutation is not an INDEL with a mono-polymer run of more than about 4.

In some exemplary embodiments, the program includes instructions for classifying a probable de novo mutation as a moderate confidence de novo mutation when the probable de novo mutation has an allele balance (AB) of about 15% or greater in the child sample and about 2% or less in each parent sample, and does not have a mapping quality (MQ) of less than about 40, and does not have a quality by depth (QD) value of less than about 2, and has minor allele count (MAC) of less than about 20 across the samples, and has about 3 soft-clipped reads or less at the variant site in the carrier of the probable de novo mutation, and is not an INDEL with a mono-polymer run of more than about 4.

In some exemplary embodiments, the program includes instructions for classifying a moderate confidence de novo mutation as a high confidence de novo mutation when the moderate confidence de novo mutation has a genotype quality (GQ) annotation in the parent sample of about 90 or greater, and has a read depth (DP) of about 10 or greater in each parent sample, and has an alternate DP of about 7 or greater in the child sample, and has QD greater than about 3 for SNPs, and has QD greater than about 5 for INDELs.

In some exemplary embodiments, DNA sequence samples comprise exome sequences.

In some exemplary embodiments, the plurality of human subjects comprises greater than 10K subjects.

In some exemplary embodiments, D-stats of low-quality samples are determined by comparing the samples' distribution of actual allele balance with an expected distribution of allele balance using a KS test.

In some exemplary embodiments, the method, non-transitory computer-implemented method or system comprises assigning a genotype likelihood score to a variant in samples from each parent and child in a trio in a constructed nuclear family and calculating a probability that the variant is a de novo mutation, and selecting the variants with a significantly high probability that the variant is a de novo mutation, and independently naively identifying a called variant in a child sample that is not called in either parent sample in a trio, and then combining the two sets of de novo mutations, thereby forming a dataset of probable de novo mutations.

In another aspect, the disclosure provides a prediction model of relatedness in a human population. The prediction model may be prepared by a process that comprises establishing a first population dataset; performing a burn-in phase of 120 years to establish a second population dataset; and modifying the second population dataset by conducting the following steps: (a) move individuals in the second population dataset to an age pool in accordance with the age of the individuals; (b) chose pairs of a single men and a single women being more distantly related than first-cousins at random from single men and single women in the second population dataset and let them marry at specified marriage by age parameters, wherein pairs are chosen until a number of marriages is reached as specified by marriage rate parameters; (c) divorce married couples at a specified divorce rate, wherein married couples are chosen at random from the second population dataset and marked as single upon divorce; (d) chose pairs of a single man and a single woman or married couples at random from the second population dataset in a specified ratio and allow them to reproduce according to specified fertility rates until a target number of successful conceptions is reached, wherein parents are restricted to being more distantly related than first cousins, and wherein all individuals in the second population dataset are limited to having one child per year; (e) allow individuals in the second population dataset to pass away at a specified death rate and at specified mortality by age parameters; (f) allow individuals to migrate to and from the second population dataset, whereby the population's age and sex distributions and the proportion of married fertile aged individuals in the second population dataset are maintained; and (g) allow individuals to move within the second population dataset, whereby individuals from a sub-population are selected at random and assigned at random to another sub-population if present until a specified move rate between sub-populations is achieved; repeat steps (a) to (g) reiteratively at one year intervals for a pre-determined number of years, wherein steps are applied to the population dataset resulting from the previous reiteration.

In some exemplary embodiments, establishing the first population dataset further includes specifying a number of sub-populations and sizes.

In some exemplary embodiments, establishing the first population dataset further includes assigning ages to individuals in the first population dataset between zero and a maximum age of fertility.

In some exemplary embodiments, the maximum age of fertility is 49 years.

In some exemplary embodiments, performing the burn-in phase further includes keeping numbers of births and deaths of individuals in the second population dataset equal and the rate of net migration of individuals zero.

In some exemplary embodiments, performing the burn-in phase further includes moving individuals second population dataset from a juvenile pool to a mating pool as individuals age above a minimum age of fertility; and moving individuals from the mating pool to an aged pool as individuals age above a maximum age of fertility; and removing individuals from all age pools if the individuals emigrate or pass away.

In some exemplary embodiments, the minimum age of fertility is 15 years and the maximum age of fertility is 49 years.

In another aspect, the disclosure provides a method of using the prediction model, wherein ascertaining individuals is performed at random.

In another aspect, the disclosure provides a method of using the prediction model, wherein ascertaining individuals is performed in a clustered fashion.

In some exemplary embodiments, ascertaining individuals further includes gathering relatedness data and relevant statistics about ascertained individuals including first- or second-degree relationships among ascertained individuals, or both.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a flow chart of an exemplary embodiment wherein compound heterozygous mutations (CHMs) are identified in a population.

FIGS. 15A, 15B, 15C, and 15D show a simulated population and ascertainment fit to the accumulation of first-degree relatedness within the DiscovEHR cohort ascertained according to an exemplary embodiment. Panel A shows accumulation of pairs of first-degree relatives; Panel B shows the proportion of the ascertained participants that have one or more first-degree relatives; Panel C shows simulated ascertainment projections with upper and lower bounds of the number of first-degree relationships; and Panel D shows simulated projections with upper and lower bounds of the proportion of the ascertained participants that have 1 or more first-degree relatives.

FIGS. 17A and 17B show a comparison between the ascertainment of first-degree relatives among 92K expanded DiscovEHR participants compared to random ascertainment of simulated populations according to an exemplary embodiment. Panel A shows ascertainment of first-degree relative pairs and Panel B shows ascertainment of number of individuals with more than one first-degree relatives

FIGS. 21A, 21B, 21C and 21D show the number of compound heterozygous mutations (CHMs) and de novo mutations (DNMs) identified per individual and per gene in the DiscovEHR cohort according to an exemplary embodiment. Panel A shows a number of CHMs per individual in the DiscovEHR cohort; Panel B shows a number of CHMs per gene in the DiscovEHR cohort; Panel C shows the distribution of the number of exonic high confidence DNMs among the children of trios in the DiscovEHR cohort; and Panel D shows a number of non-synonymous DNMs per gene.

FIGS. 36A and 36B show the relationship between paternal and maternal ages at birth in the DiscovEHR cohort and the number of exonic DNMs identified in the child according to an exemplary embodiment.

DETAILED DESCRIPTION

Figure 1:
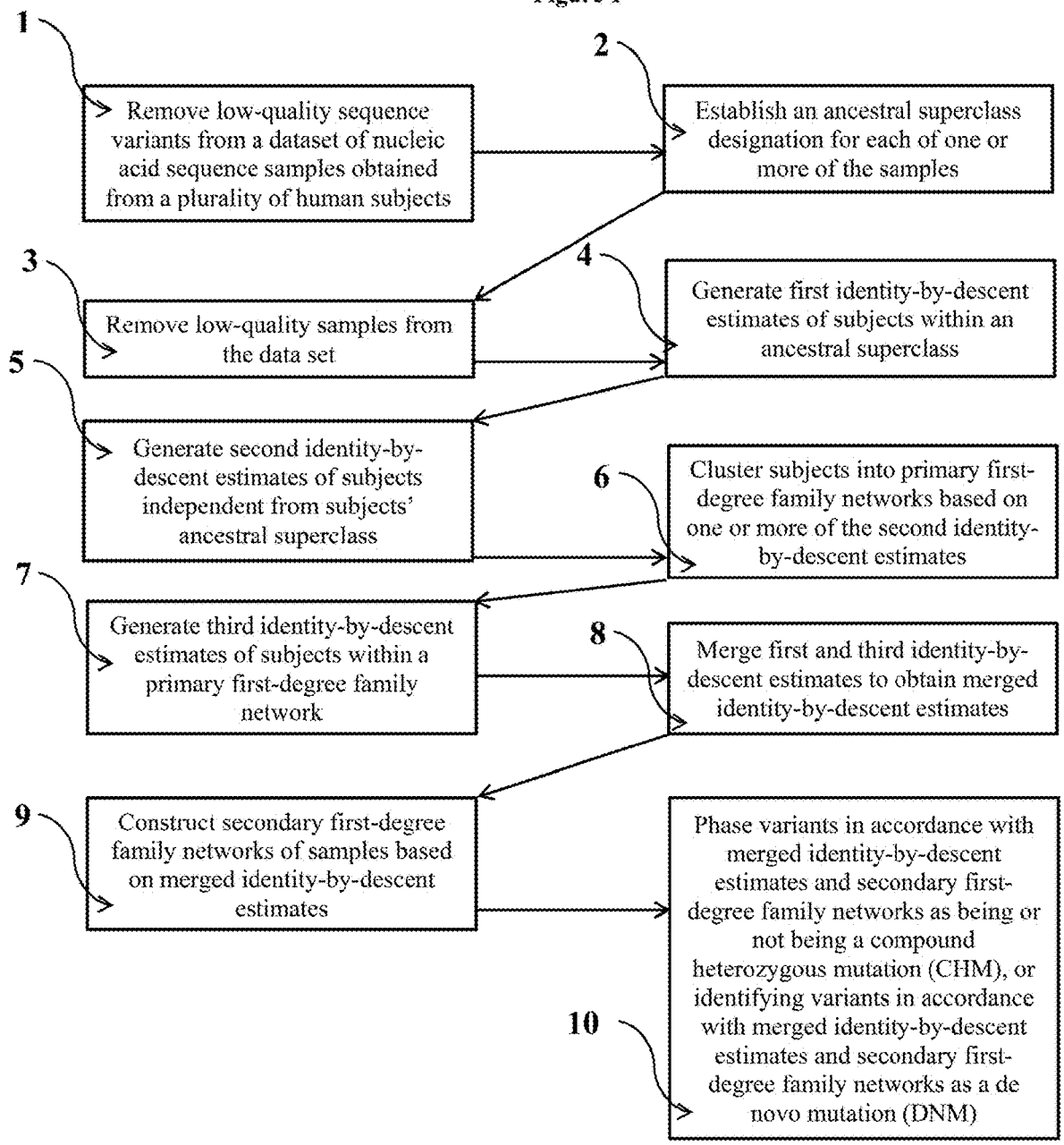
FIG. 1 is a flow chart of an exemplary embodiment wherein genetic variants in a population are phased/identified by leveraging the population's relatedness.

The term "a" should be understood to mean "at least one"; and the terms "about" and "approximately" should be understood to permit standard variation as would be understood by those of ordinary skill in the art; and where ranges are provided, endpoints are included.

Previous large scale human genomic studies typically collected human samples across a number of different geographic areas and/or health care systems and combined them to generate cohorts for analysis. While the total number of individuals sampled in these cohorts was often high, the extent of relatedness and family structure in these cohorts tended to be relatively low. Many statistical methods commonly used in the context of genome analysis, including association analysis and principle component analysis, require that all samples are unrelated. Otherwise, the statistical outputs of these tests will be biased, resulting in inflated p-values and false positive findings (FIG. 8) (Kang et al. (2010), Nature Publishing Group 42, 348-354; Sun and Dimitromanolakis (2012), Methods Mol. Biol. 850, 47-57; Devlin and Roeder (1999), Biometrics 55, 997-104; and Voight and Pritchard (2005), PLoS Genet 1, e32-10).

Removal of family structure from a dataset is a viable option if the dataset has only a handful of closely related samples (Lek, et al. (2016), Nature Publishing Group 536, 285-291; Fuchsberger et al. (2016), Nature Publishing Group 536, 41-47; Locke et al. (2015), Nature 518, 197-206; and Surendran et al. (2016) Nat Genet 48, 1151-1161). Removal of family structure is also a possible option if the unrelated subset of the data is adequate for the statistical analysis, such as computing principle components (PCs) and then projecting the remaining samples onto these PCs (Dewey et al. (2016), Science 354, aaf6814-aaf6814). A number of methods exist to help investigators retain the maximally sized unrelated set of individuals (Staples at al. (2013), Genet. Epidemiol. 37, 136-141; Chang at al. (2015), Gigascience 4, 7). Unfortunately, removal of related individuals not only reduces the sample size but also discards the valuable relationship information. In fact, such a loss of information is unacceptable for many analyses if the dataset has even a moderate level of family structure.

The disclosure is based, at least in part, on the recognition that information about family and pedigree structure and relatedness within a dataset of genomic samples of a plurality of subjects is useful because it opens the door to a number of analyses that allow investigating the connection between rare genetic variations (e.g., compound heterozygous and/or de novo mutations) and diseases, among other things.

The disclosure is also based, at least in part, on the recognition that genome-wide identity-by-decent (IBD) estimates are an excellent metric to quantify the level of relatedness within a dataset of genomic samples of a plurality of subjects and between two pairs of individuals.

Several statistical methods have been developed that model accurate pairwise relationships. For example, genome-wide association studies that use mixed models are better powered and outperform methods that do not model the confounding relatedness (Kang et al. (2010), Nature Publishing Group 42, 348-354; Zhang et al. (2010), Nat Genet 42, 355-360; Yang et al. (2014), Nat Genet 46, 100-106; and Kirkpatrick and Bouchard-Côté (2016), arXiv q-bio.QM), but mixed models do not fully leverage the information contained within the family structure and may not scale practically to datasets with hundreds of thousands of samples and hundreds to thousands of phenotypes. Pairwise relationships can also be used in a pedigree-free QTL linkage analysis (Day-Williams et al. (2011), Genet. Epidemiol. 35, 360-370). Additional software packages that model population structure and family structure exist for pairwise relationship estimation (PCrelate) (Conomos et al. (2016), Am. J. Hum. Genet. 98, 127-148) and principle component analysis (PC-AiR) (Conomos et al. (2015), Genet. Epidemiol. 39, 276-293).

In contrast to traditional genome-wide association studies, recent and future large-scale genomic studies, for example, those embodied in the disclosure, sample tens to hundreds of thousands of participants from individual geographical areas. As a result, these studies ascertain a much larger proportion of people from the same geographical area and thus family and pedigree structure within the sampled dataset to identify rare variants segregating in families that are underappreciated in traditional population-wide association analyses.

Figure 8A:
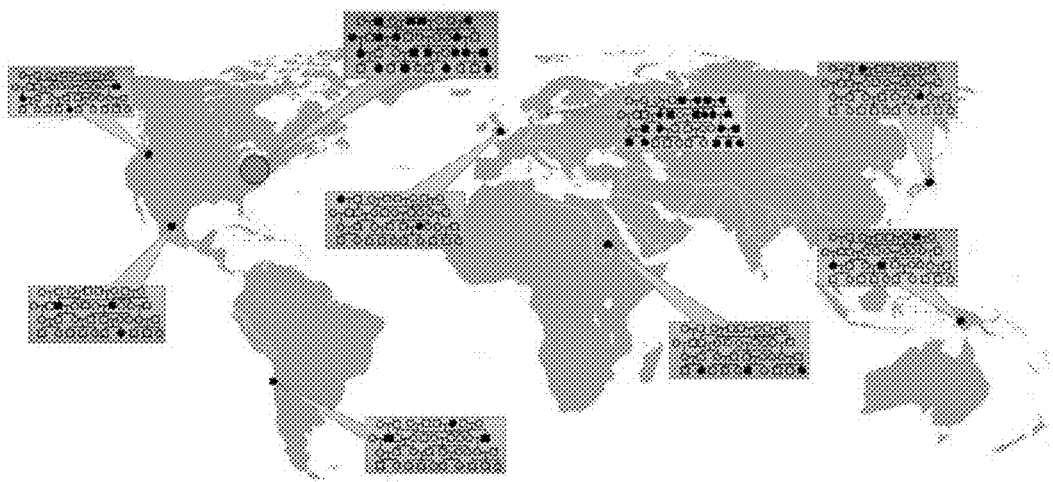
FIGS. 8A, 8B, 8C and 8D represent a scheme that provides an overview of different types of population-based genomic studies and corresponding sampling methods and illustrates that heavy ascertainment increases family structure and impacts statistical analysis approaches that should be used. Panel A shows a schematic illustration of (1) traditional population-based genomic studies (gray boxes); (2) health-care population-based genomic (HPG) studies (green box), and (3) family-based genomic studies (yellow box); Panel B shows a line graph of family structure in the aforesaid three ascertainment approaches; Panel C shows a scatter graph of family structure in the aforesaid three ascertainment approaches (the lines indicate first-degree and second-degree pairwise relationships ascertained from the three aforesaid ascertainment approaches); Panel D shows a statistical analysis approaches binned into four categories based on the level of family structure.
Figure 8B:
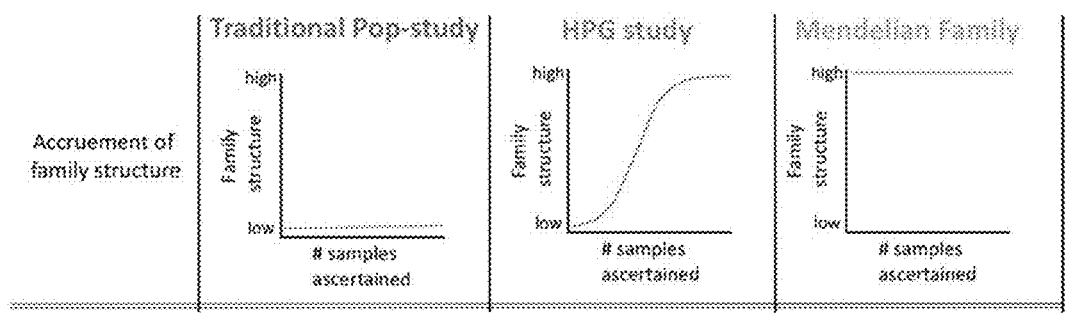
Figure 8C:
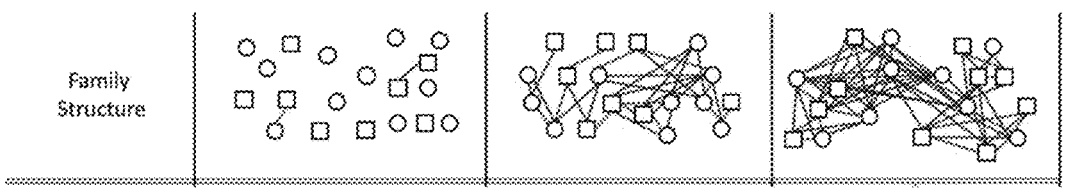
Figure 8D:
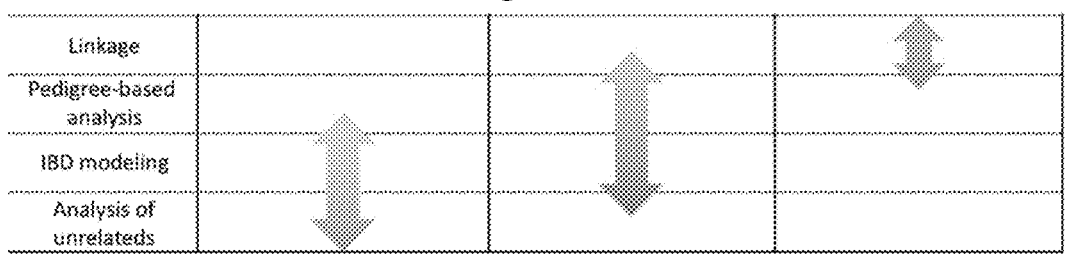

The data of such large-scale genomic studies are enriched for family structure and distant cryptic relatedness for several reasons. First, the studies heavily sample from specific geographical areas, for example through a healthcare system populations, and the number of pairs of related individuals ascertained increases combinatorially as more samples are ascertained from a single population (FIG. 8A). Second, families who live in the same geographic area are likely obtaining medical care from the same doctors at the same healthcare system due to shared insurance coverage and convenience. Third, shared genetic and environmental factors can increase the frequency of healthcare interactions for certain families. Both family structure and distant cryptic relatedness are even more pronounced in populations with low migration rates (Henn et al. (2012), PLoS ONE 7, e34267). The impact of family structure can be observed through the effect of the sampling methods on linkage, pedigree-based analysis, IBD modeling, and analysis of unrelateds (FIG. 8, panel D). "Linkage" refers to traditional linkage analyses using one or more informative pedigrees; "Pedigree-based analysis" refers to statistical methods beyond linkage that use pedigree structures within a larger cohort that includes unrelated individuals; "IBD modeling" refers to analysis that model the pairwise relationships between individuals without using the entire pedigree structure; and "Analysis of Unrelateds" refers to analyses that assume all individuals in the cohort to be unrelated.

The disclosure focuses on family structure and demonstrates a high-level of family structure using both real and simulated data. One of the improvements of the disclosure is that it identifies and/or phases compound heterozygous mutations (CHMs) and/or de novo mutations (DNMs) more accurately and reliably than traditional approaches (see data disclosed in Examples section).

Thus, the disclosure provides methods for phasing genetic variants in an ascertained population by leveraging the population's relatedness. A flow outlining exemplary phasing methods is provided in FIG. 1.

The methods may be applied to various types of genetic variants in different populations. Non-limiting examples of types of genetic variants that may be assessed include point mutations, insertions, deletions, inversions, duplications and multimerizations. Non-limiting examples of types of populations include single-healthcare-network-populations; multi-healthcare-network-populations; racially, culturally or socially homogeneous or heterogeneous populations; mixed-age populations or populations homogenous in terms of age; geographically concentrated or dispersed populations; or combination thereof. Non-limiting examples of means by which the genetic variants may be acquired include the following steps:

Sample preparation and sequencing (Dewey et al. (2016), Science 354, aaf6814-1 to aaf6814-10);

Upon completion of sequencing, raw data from each sequencing run are gathered in local buffer storage and uploaded to the DNAnexus platform (Reid et al. (2014); BMC Bioinformatics 15, 30) for automated analysis.

Sample-level read files are generated with CASAVA (Illumina Inc., San Diego, Calif.) and aligned to GRCh38 with BWA-mem (Li and Durbin (2009); Bioinformatics 25, 1754-176; Li (2013); arXiv q-bio.GN).

The resultant BAM files are processed using GATK (McKenna et al. (2010); Genome Res. 20, 1297-1303) and Picard to sort, mark duplicates, and perform local realignment of reads around putative indels.

Sequenced variants are annotated with snpEFF (Cingolani et al. (2012); Fly (Austin) 6, 80-92) using Ensembl85 gene definitions to determine the functional impact on transcripts and genes.

It is understood that the methods are not limited to any of the aforesaid steps, and that the acquisition of sequence variants may be conducted by any suitable means.

FIG. 1 is a flow chart of an exemplary embodiment wherein genetic variants in a population are phased/identified by leveraging the population's relatedness. Low-quality sequence variants from a dataset of nucleic acid sequence samples obtained from a plurality of human subjects may be removed at step 1 by any suitable means. Non-limiting examples of such means include PLINK (Chang et al. (2015); Gigascience 4, 7) and those disclosed in the Examples.

An ancestral superclass designation for each of one or more of the samples may be established at step 2 by any suitable means. Non-limiting examples of such means include PLINK (Chang et al. (2015); Gigascience 4, 7) and those disclosed in the Examples.

Low-quality samples may be removed at step 3 from the dataset by any suitable means. Non-limiting examples of such means include those disclosed in Dewey et al. (2016), Science 354, aaf6814-1 to aaf6814-10, and those disclosed in the Examples.

First identity-by-descent estimates of subjects within an ancestral superclass may be generated at step 4 by any suitable means. Non-limiting examples of such means include PLINK (Chang et al. (2015); Gigascience 4, 7), and those disclosed in the Examples.

Second identity-by-descent estimates of subjects independent from subjects' ancestral superclass may be generated at step 5 and at step 6, subjects may be clustered into primary first-degree family networks based on one or more of the second identity-by-descent estimates by any suitable means. Non-limiting examples of such means include PLINK (Chang et al. (2015); Gigascience 4, 7), and those disclosed in the Examples.

Third identity-by-descent estimates of subjects within a primary first-degree family network may be generated at step 7 by any suitable means. Non-limiting examples of such means include PLINK (Chang et al. (2015); Gigascience 4, 7), and those disclosed in the Examples.

First and third identity-by-descent estimates may be merged at step 8 to obtain merged identity-by-descent estimates by any suitable means. Non-limiting examples of such means include PLINK (Chang et al. (2015); Gigascience 4, 7), and those disclosed in the Examples.

Secondary first-degree family networks of subjects based on merged identity-by-descent estimates may be constructed at step 9 by any suitable means. Non-limiting examples of such means include PLINK (Chang et al. (2015); Gigascience 4, 7), and those disclosed in the Examples.

Variants may be phased at step 10 in accordance with merged identity-by-descent estimates and secondary first-degree family networks as being or not being a compound heterozygous mutation (CHM) by any suitable means, or variants may be identified in accordance with merged identity-by-descent estimates and secondary first-degree family networks as a de novo mutation (DNM) by any suitable means. Non-limiting examples of such means include those disclosed in FIGS. 6 and 7 and in the Examples.

Figure 6A:
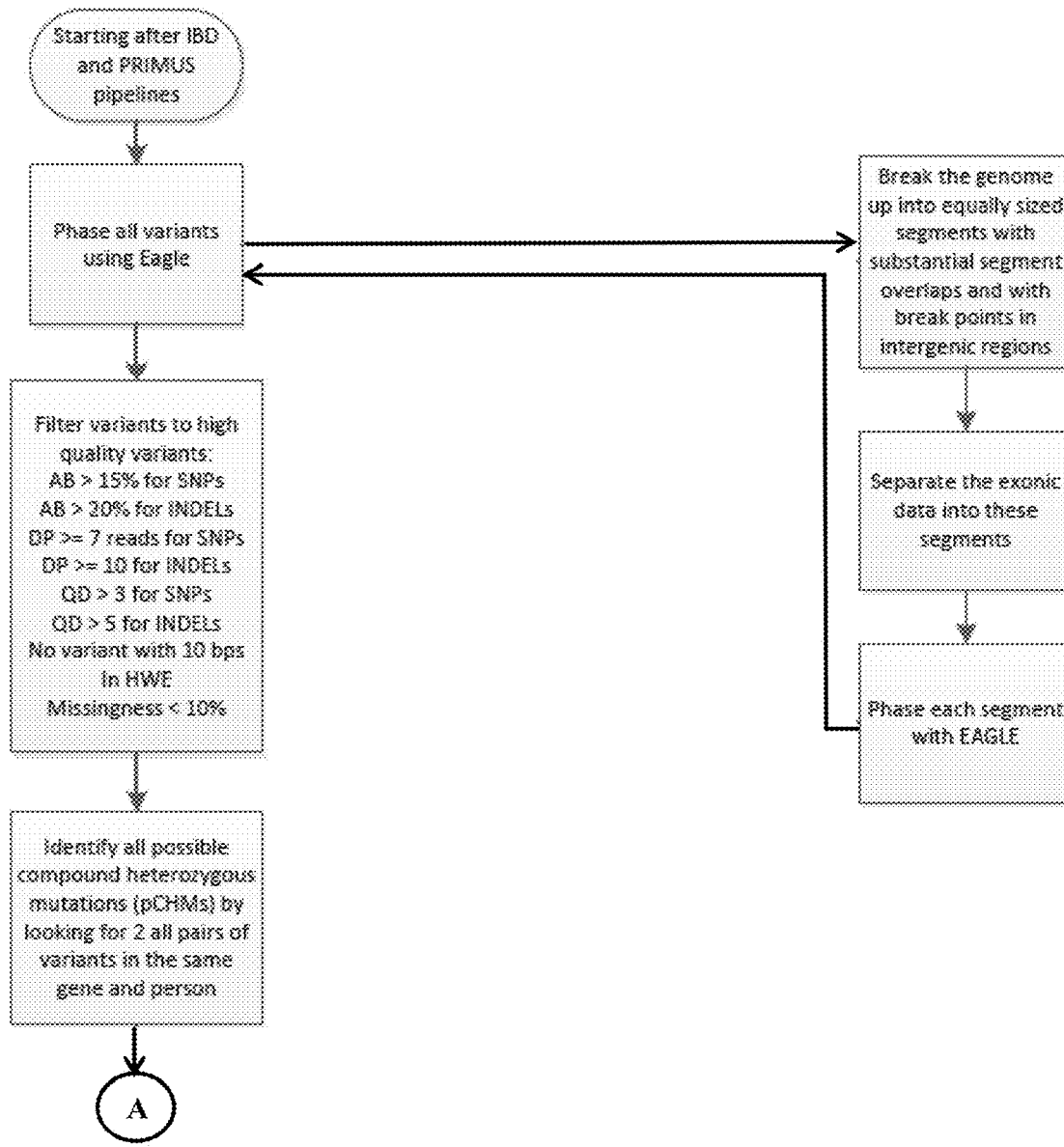
FIGS. 6A-C represent a flow chart of an exemplary embodiment wherein compound heterozygous mutations (CHMs) are identified/phased in a population.
Figure 6B:
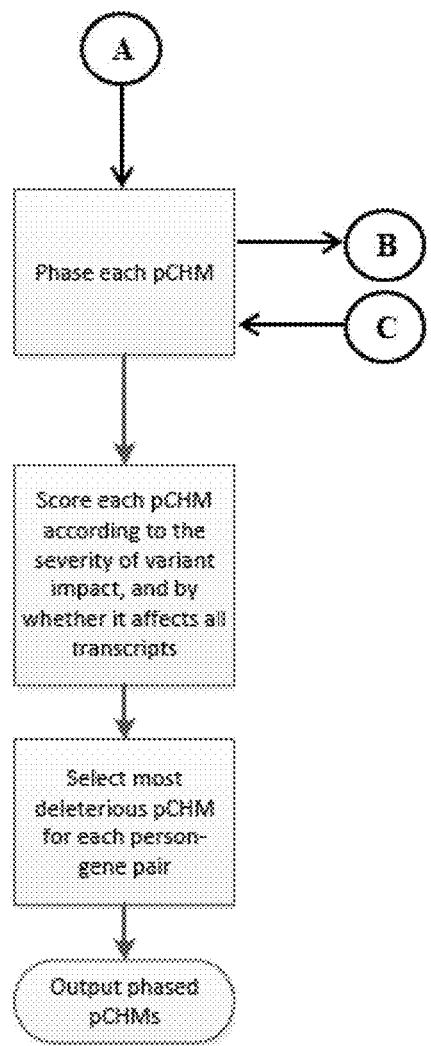
Figure 6C:
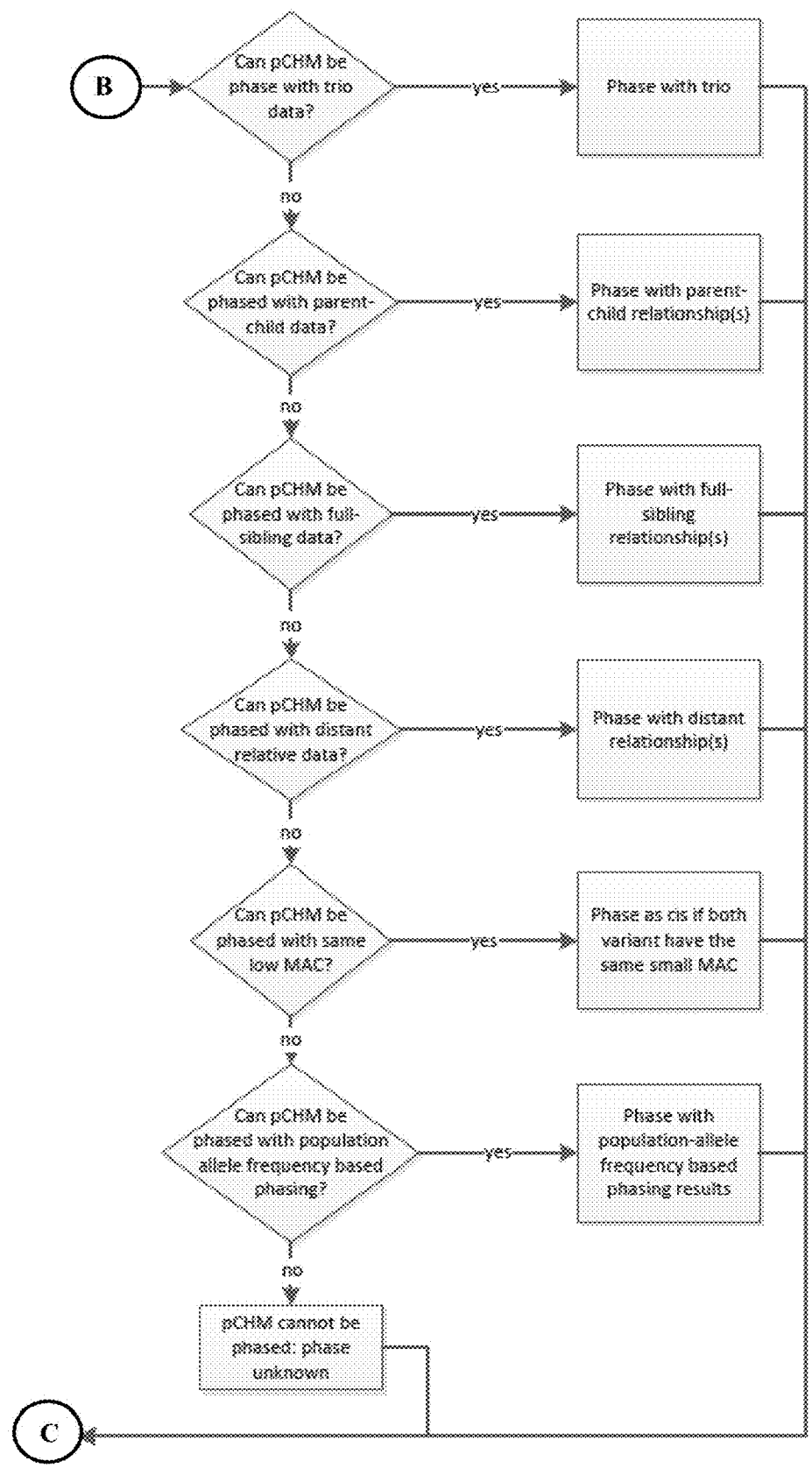
Figure 7A:
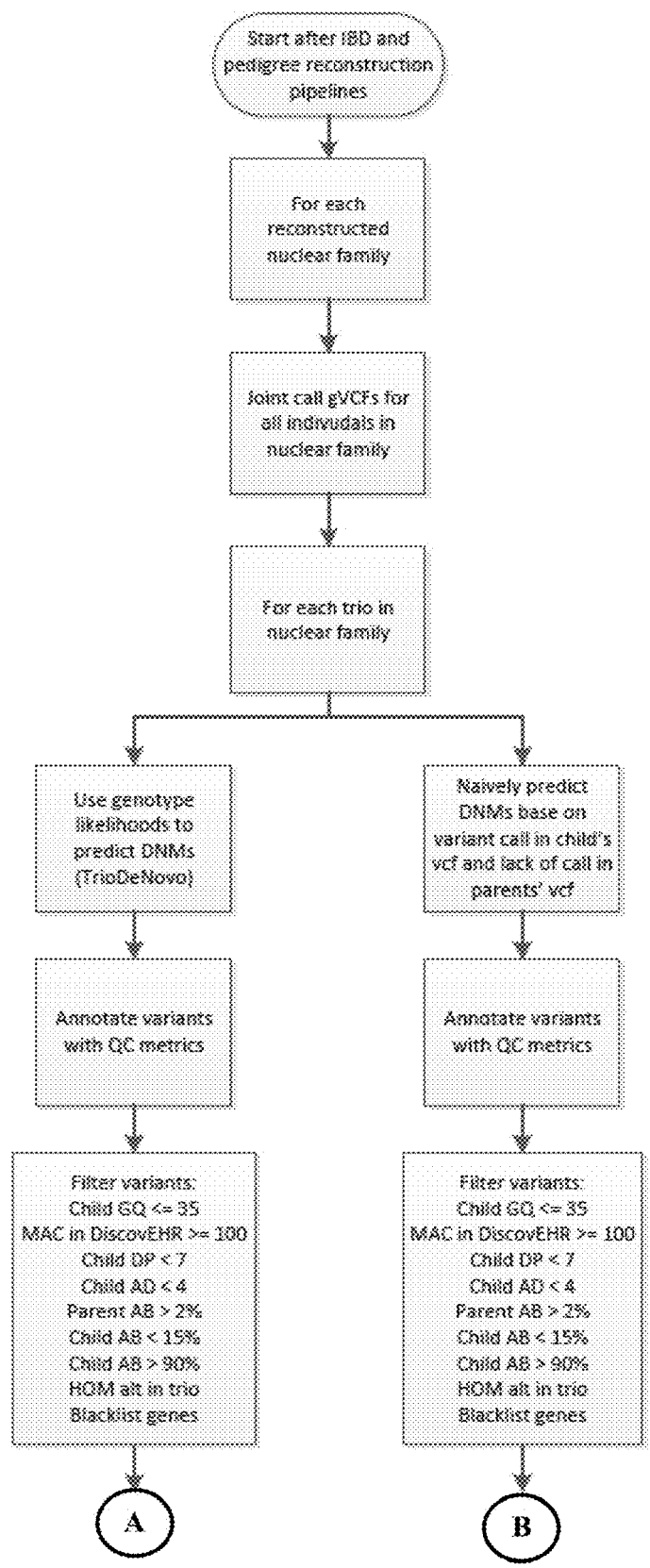
FIGS. 7A and 7B represent a flow chart of an exemplary embodiment wherein de novo mutations (DNMs) are identified in a population. DNM calling, filtering, and confidence ranking workflow. GQ=genotype quality; MAC is minor allele count in DiscovEHR; DP=read depth at the DNM site; AD=the alternate allele depth; AB=alternate allele balance; MQ=mapping quality; QD=quality by depth for the DNM site in the joint called DiscovEHR pVCF; Homopolymer INDEL is an INDEL with more than 4 consecutive base pairs of the same nucleotide. Blacklisted genes include PDE4DIP, PRAMEF1, PABPC3, NBPF10, NBPF14, olfactory genes (OR*), MUC genes (MUC*), and HLA genes (HLA-*).
Figure 7B:
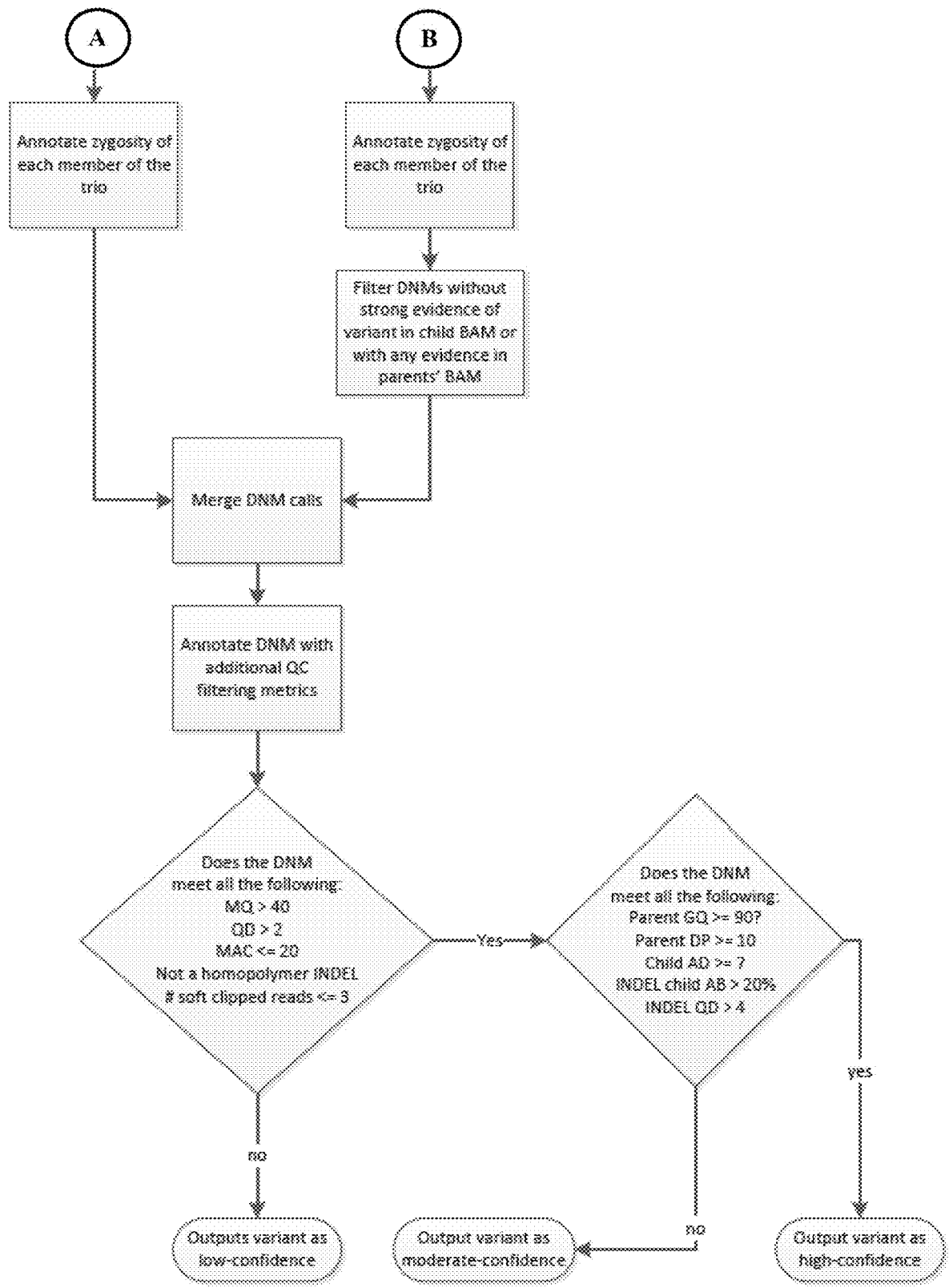

To illustrate, but not to limit, a methodology for generating identity-by-descent (IBD) estimates, as well as using the IBD estimates to phase gene variants as compound heterozygous mutations (CHM) or potential compound heterozygous mutations (pCHM), or de novo mutations (DNM), FIGS. 5 through 7 provide a basic operational logic. Programs identified in the logic (e.g., EAGLE, PLINK, etc.) are exemplary for the steps in which they are identified, but it is understood that such programs are not the only way for carrying out such steps.

Phasing variants as a compound heterozygous mutation (CHM) may comprise: (1) phasing variants according to population allele frequencies, (2) removing variants outside of Hardy-Weinberg equilibrium (HWE) or within 10 base pairs of another variant in the same sample or both; and removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof, (3) selecting remaining variants as potential compound heterozygous mutations (pCHMs) where there are one or more pairs of variants in the same sample and in the same gene, and (4) phasing pCHMs as either cis or trans pCHMs, and then classifying the pCHM phased as trans pCHM as CHM. Phasing variants according to population allele frequencies may be facilitated by any suitable means, including but not limited to EAGLE (Loh et al. (2016), Nat Genet 48, 1443-1448). Variants not satisfying certain selection criteria may be removed, remaining variants selected as potential compound heterozygous mutations and potential compound heterozygous mutations phased by any suitable means, including those described in the Examples. These exemplary embodiments are also illustrated in FIG. 6.

Phasing variants as a compound heterozygous mutation may comprise: removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof. These steps may be conducted as described elsewhere herein except that the exclusion parameters are set to a more stringent level.

In some exemplary embodiments, the method further comprises: (1) scoring CHMs according to functional effect priority, and (2) selecting CHMs having the highest functional effect priority score per gene per sample, such that when the human has more than one CHM in the same gene, the CHM most likely to result in protein function inhibition is identified. These steps may be conducted by any suitable means, including but not limited to SIFT (Loh et al. (2016); Nat Genet 48, 1443-1448) (damaging), PolyPhen2 HDIV45 (damaging and possibly damaging), PolyPhen2 HVAR (damaging and possibly damaging), LRT46 (deleterious), and MutationTaster (Schwarz et al. (2014); Nat. Methods 11, 361-362) (disease causing automatic and disease causing).

Phasing variants as a de novo mutation may comprise: (1) identifying variants in samples in second first-degree family networks and trios thereof, (2) assigning genotype likelihood scores to variants in parent samples and corresponding child sample in a trio and calculating a probability that the variant is a de novo mutation, and identifying the variant as a probable de novo mutation when the calculated probability is statistically significant, (3) identifying a variant in a child sample in a trio and identifying the variant as a probable de novo mutation when the variant is not present in either parent sample in the trio, (4) filtering probable de novo mutations identified by removing probable de novo mutations having a genotype quality (GQ) annotation in the child sample of less than about 35, or having an alternate allele count (AC) of 10 or greater across the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof, and (5) combining filtered probable de novo mutations identified, thereby forming a probable de novo mutation dataset. These steps may be conducted by any suitable means, including those described in the Examples. These exemplary embodiments are also illustrated in FIG. 7.

In some exemplary embodiments, the method further comprises: classifying a probable de novo mutation in the probable de novo mutation dataset as a moderate confidence de novo mutation when the probable de novo mutation has an allele balance of about 0.15 or greater in the child sample and about 0.02 or less in each parent sample, and does not have a mapping quality of less than about 40, and does not have a quality by depth (QD) value of less than about 2, and has MAC of less than about 20 across the samples, and has about 3 soft-clipped reads or less at the variant site in the carrier of the probable de novo mutation, and is not an INDEL with a mono-polymer run of more than about 4. In some exemplary embodiments, the method further includes: classifying a moderate confidence de novo mutation as a high confidence de novo mutation when the moderate confidence de novo mutation has a genotype quality annotation in the parent sample of about 90 or greater, and has a read depth of about 10 or greater in each parent sample, and has an alternate read depth of about 7 or greater in the child sample, and has QD greater than about 3 for SNPs, and has QD greater than about 5 for INDELs. Both exemplary embodiments may be practiced in any of the ways, including but not limited to those disclosed in the Examples.

The disclosure also provides methods for identifying compound heterozygous mutations (CHMs) in a population. A flow chart illustrating an example of a method for identifying CHMs is provided in FIG. 2.

The method may be applied to any type of DNA sequence samples from any type of human subjects derived by any means. Non-limiting examples of variants include point mutations, insertions, deletions, inversions, duplications and multimerizations. Non-limiting examples of types of human subjects include human subjects from single-healthcare-network-populations; multi-healthcare-network-populations; racially, culturally or socially homogeneous or heterogeneous populations; mixed-age populations or populations homogenous in terms of age; geographically concentrated or dispersed populations; or combination thereof. DNA sequence samples may be acquired in any of the many ways, including but not limited to those disclosed in Dewey et al. (2016), Science 354, aaf6814-1 to aaf6814-10.

In some exemplary embodiments, DNA sequence samples comprise exome sequences. Exome DNA may be isolated by any of the commonly used methods, or as described in Dewey et al. (2016), Science 354, aaf6814-1 to aaf6814-10.

Variants in DNA sequence samples from a plurality of human subjects may be identified at step 11 by any suitable means. Non-limiting examples of means by which the variants may be identified include the following steps:

Upon completion of sequencing, raw data from each sequencing run are gathered in local buffer storage and uploaded to the DNAnexus platform (Reid et al. (2014); BMC Bioinformatics 15, 30) for automated analysis.

Sample-level read files are generated with CASAVA software (Illumina Inc., San Diego, Calif.) and aligned to GRCh38 with BWA-mem (Li and Durbin (2009); Bioinformatics 25, 1754-176; Li (2013); arXiv q-bio.GN).

The resultant BAM files are processed using GATK (McKenna et al. (2010); Genome Res. 20, 1297-1303) and Picard to sort, mark duplicates, and perform local realignment of reads around putative indels.

Sequenced variants are annotated with snpEFF (Cingolani et al. (2012); Fly (Austin) 6, 80-92) using Ensembl85 gene definitions to determine the functional impact on transcripts and genes.

It is understood that the methods are not limited to any of the aforesaid steps, and that the acquisition of sequence variants may be conducted by any suitable means.

FIG. 2 is a flow chart of an exemplary embodiment wherein compound heterozygous mutations (CHMs) are identified in a population. An ancestral superclass designation for subjects based on identified variants may be established at step 12; first identity-by-descent estimates of subjects within an ancestral superclass may be generated at step 13; second identity-by-descent estimates of subjects independent from subjects' ancestral superclass may be generated at step 14; subjects may be clustered at step 15 into primary first-degree family networks based on one or more of the second identity-by-descent estimates; third identity-by-descent estimates of subjects within a primary first-degree family network may be generated at step 16; first and third identity-by-descent estimates may be merged at step 17 to obtain merged identity-by-descent estimates; and secondary first-degree family networks may be constructed at step 18 based on merged identity-by-descent estimates by any suitable means. Non-limiting examples of such means include PLINK (Chang et al. (2015); Gigascience 4, 7), and those disclosed in the Examples. In some exemplary embodiments, identity-by-descent estimates comprise genome-wide calculations of IBD 0, 1, and 2 values among sample pairs.

Variants in samples may be phased at step 19 according to population-allele frequencies by any suitable means, including but not limited to EAGLE (Loh et al. (2016), Nat Genet 48, 1443-1448).

A pair of phased variants may be classified at step 20 as a potential CHM based on the presence of the two variants in the same subject and gene, which was ascertained by testing all possible combinations of heterozygous pLoFs and/or deleterious missense variants within a gene of the same person.

Figure 9:
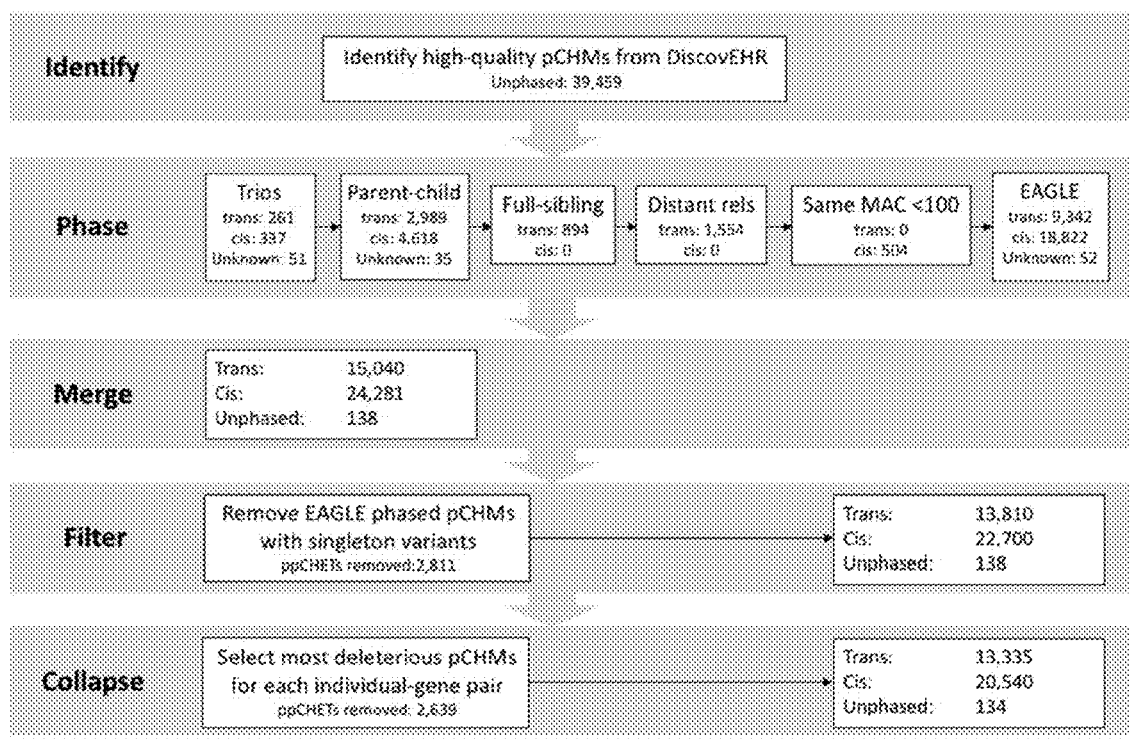
FIG. 9 is a flow-chart of an exemplary embodiment outlining the cascading analysis conducted for determining phase of potential compound heterozygous mutations (pCHMs) among the dataset analyzed (DiscovEHR dataset; see Examples).

A potential CHM may be phased at step 21 as cis or trans, and the potential CHM phased as trans may be classified as CHM. A potential CHM may be phased by any of suitable means. In a non-limiting example, a combination of population allele-frequency-based phasing with EAGLE and pedigree/relationship-based phasing is used to determine if the potential CHM is phase cis or trans (this exemplary process is also illustrated in FIG. 9).

In some exemplary, the method further includes filtering identified variants before ancestral superclass designations for subjects are established; and in some exemplary embodiments, the method further includes filtering identified variants before second identity-by-descent estimates of subjects are generated. Variants may be filtered by any suitable means. Non-limiting examples of such means include PLINK (Chang et al. (2015); Gigascience 4, 7) and those disclosed in the Examples.

In some exemplary embodiments, filtering variants includes removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof. Variants not satisfying certain selection criteria may be removed, remaining variants selected as potential compound heterozygous mutations and potential compound heterozygous mutations phased by any suitable means, including those described in the Examples. These exemplary embodiments are also illustrated in FIG. 6.

In some exemplary embodiments, the method further comprises removing low-quality samples after identified variants have been filtered. Low-quality samples may be removed by any suitable means. Non-limiting examples of such means include those disclosed in Dewey et al. (2016), Science 354, aaf6814-1 to aaf6814-10, which are generally known, and those disclosed in the Examples. In some exemplary embodiments, the parameters are adjusted such that samples having a D-stat of >0.12 or 20× read coverage of <75%, or both, are low-quality samples that are removed.

Merging first and third identity-by-descent estimates may comprise augmenting the first identity-by-descent estimates with pairwise identity-by-descent estimates unique to the third identity-by-descent estimates, which may be facilitated by, for example but not limited to, PLINK (Chang et al. (2015); Gigascience 4, 7), and those means disclosed in the Examples.

In some exemplary embodiments, the method further comprises filtering variants after variants have been phased according to population-allele frequencies, the latter of which may in some exemplary embodiments include dividing DNA sequence samples of human subjects into genomic segments having approximately equal size, substantial segment overlap and break points in intergenic regions. Phasing variants according to population allele frequencies may be facilitated by any suitable means, including but not limited to EAGLE (Loh et al. (2016), Nat Genet 48, 1443-1448). Filtering variants phased according to population-allele frequencies may comprise removing variants outside of Hardy-Weinberg equilibrium (HWE) or within 10 base pairs of another variant in the same sample or both; and removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof. Filtering variants phased according to population-allele frequencies may comprise removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof. Variants not satisfying certain selection criteria may be removed, remaining variants selected as potential compound heterozygous mutations and potential compound heterozygous mutations phased by any suitable means, including those described in the Examples. These exemplary embodiments are also illustrated in FIG. 6.

Potential CHMs can be phased based on trio data, or parent-child data, or full-sibling data, or distant relative data, or a combination thereof or are phased based on minor allele counts (MAC); or are phased based on population-allele frequencies; or a combination thereof. Phasing may be facilitated by any suitable method commonly used in the art. In a non-limiting example, a combination of population allele-frequency-based phasing with EAGLE and pedigree/relationship-based phasing is used to phase potential CHMs. This exemplary process is also illustrated in FIG. 9.

In some exemplary embodiments, the method further comprises scoring CHMs according to functional effect priority, and selecting CHMs having the highest functional effect priority score per gene per sample, thereby obtaining a collection of medically relevant mutations. These steps may be conducted by any suitable means, including but not limited to SIFT (Loh et al. (2016); Nat Genet 48, 1443-1448) (damaging), PolyPhen2 HDIV (damaging and possibly damaging), PolyPhen2 HVAR (damaging and possibly damaging), LRT (deleterious), and MutationTaster (Schwarz et al. (2014); Nat. Methods 11, 361-362) (disease causing automatic and disease causing).

In some exemplary embodiments, D-stats of low-quality samples are determined by comparing the samples' distribution of actual allele balance with an expected distribution of allele balance using a KS test.

The disclosure also provides methods for identifying de novo mutations (DNMs) in a population. A flow chart illustrating an example of a method for identifying DNMs is provided in FIG. 3.

The methods may be applied to any type of DNA sequence samples from any type of human subjects derived by any means. Non-limiting examples of variants include point mutations, insertions, deletions, inversions, duplications and multimerizations. Non-limiting examples of types of human subjects include human subjects from single-healthcare-network-populations; multi-healthcare-network-populations; racially, culturally or socially homogeneous or heterogeneous populations; mixed-age populations or populations homogenous in terms of age; geographically concentrated or dispersed populations; or combination thereof. DNA sequence samples may be acquired in any of the many ways, including but not limited to those disclosed in Dewey et al. (2016), Science 354, aaf6814-1 to aaf6814-10.

The DNA sequence samples comprise or are exome sequences. Exome DNA may be isolated by any of the commonly used methods, or as described in Dewey et al. (2016), Science 354, aaf6814-1 to aaf6814-10.

Variants in DNA sequence samples from a plurality of human subjects may be identified 22 by any suitable means. Non-limiting examples of means by which the variants may be identified include the following steps:

Upon completion of sequencing, raw data from each sequencing run are gathered in local buffer storage and uploaded to the DNAnexus platform (Reid et al. (2014); BMC Bioinformatics 15, 30) for automated analysis.

Sample-level read files are generated with CASAVA (Illumina Inc., San Diego, Calif.) and aligned to GRCh38 with BWA-mem (Li and Durbin (2009); Bioinformatics 25, 1754-176; Li (2013); arXiv q-bio.GN).

The resultant BAM files are processed using GATK (McKenna et al. (2010); Genome Res. 20, 1297-1303) and Picard to sort, mark duplicates, and perform local realignment of reads around putative indels.

Sequenced variants are annotated with snpEFF (Cingolani et al. (2012); Fly (Austin) 6, 80-92) using Ensembl85 gene definitions to determine the functional impact on transcripts and genes.

It is understood that the disclosure is not limited to any of the aforesaid steps, and that the acquisition of sequence variants may be conducted by any suitable means.

Figure 3:
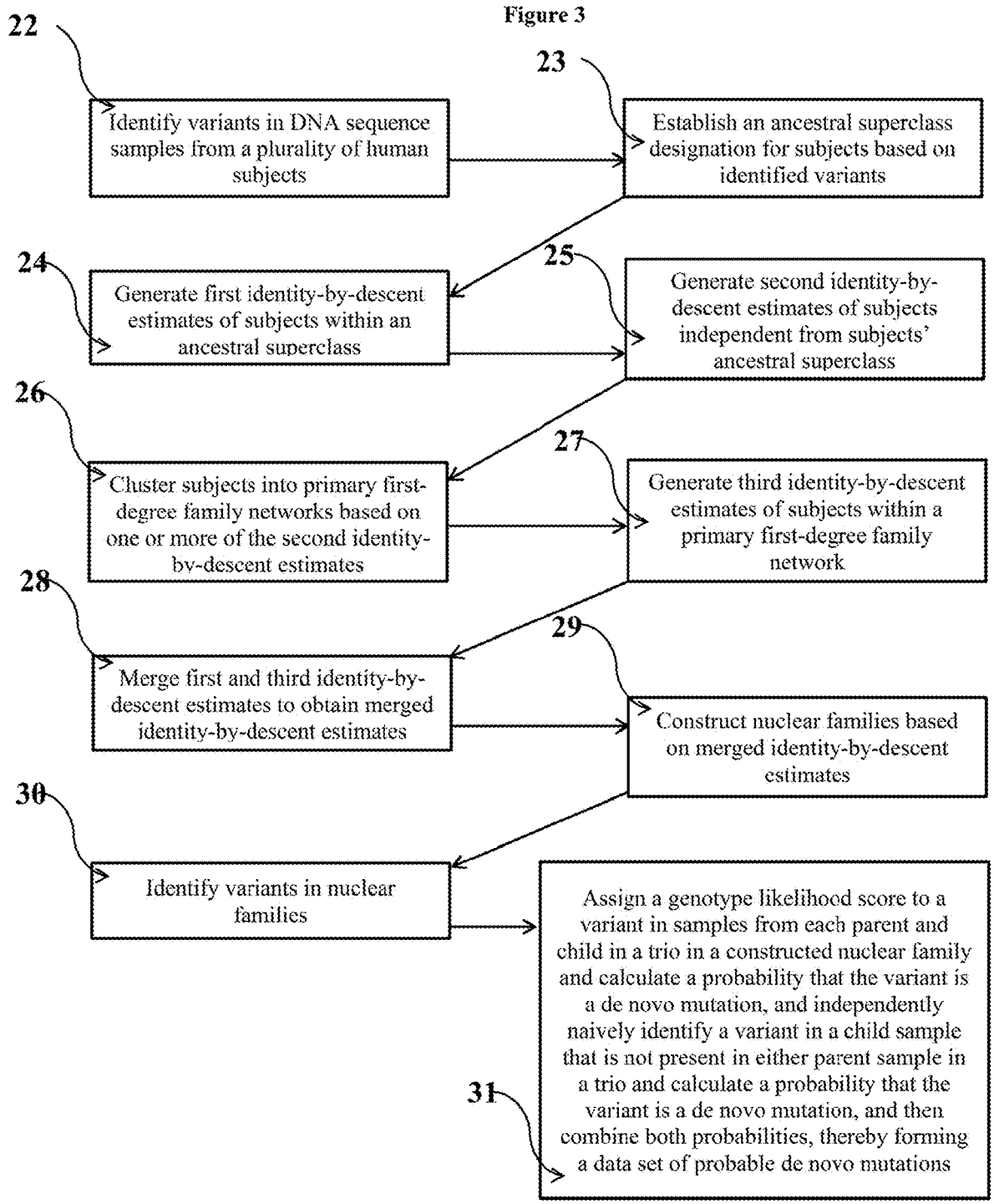
FIG. 3 is a flow chart of an exemplary embodiment wherein de novo mutations (DNMs) are identified in a population.
Figure 4:
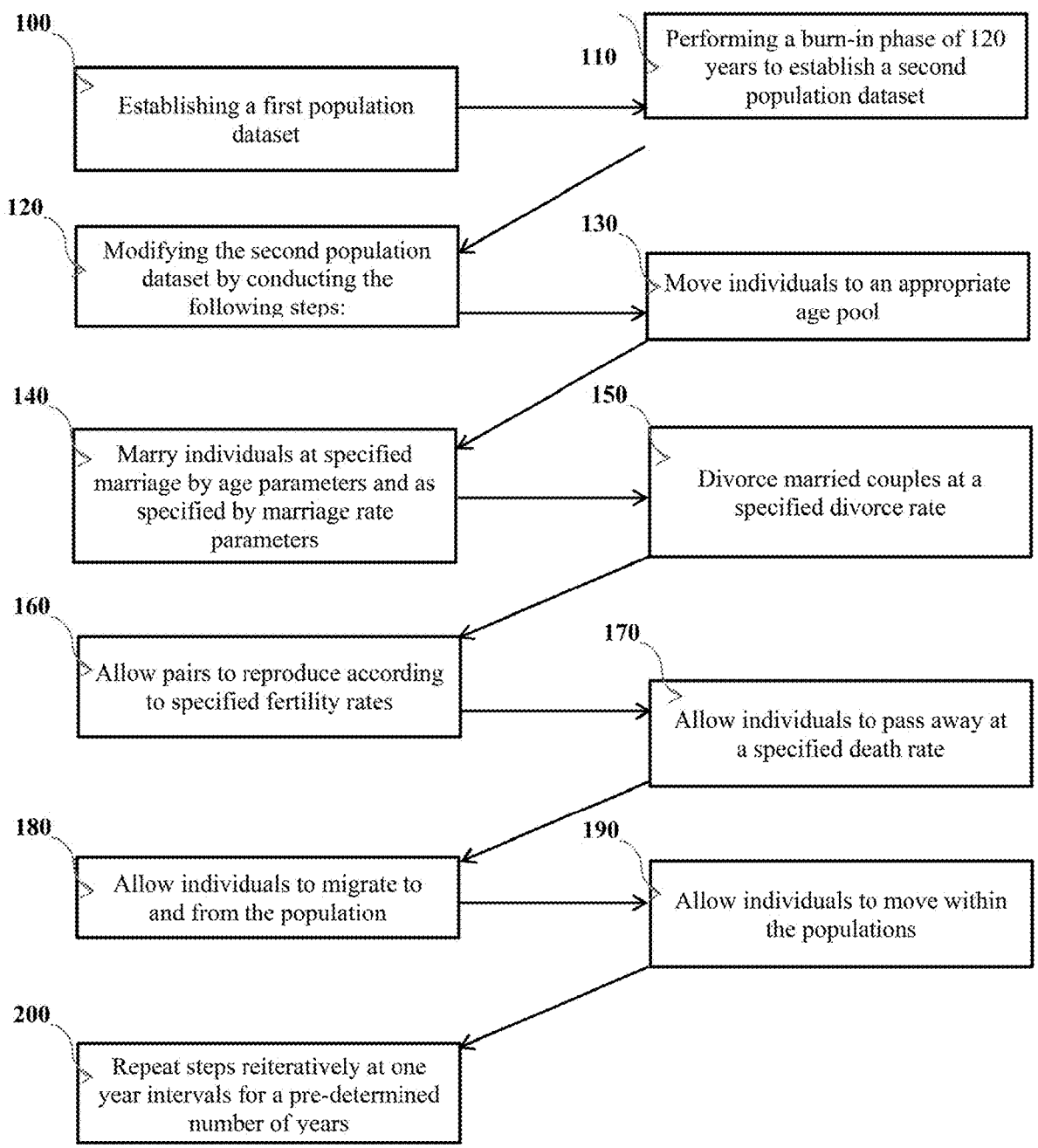
FIG. 4 is a flow chart of a method of making a prediction model of relatedness in a human population according to an exemplary embodiment.
Figure 5A:
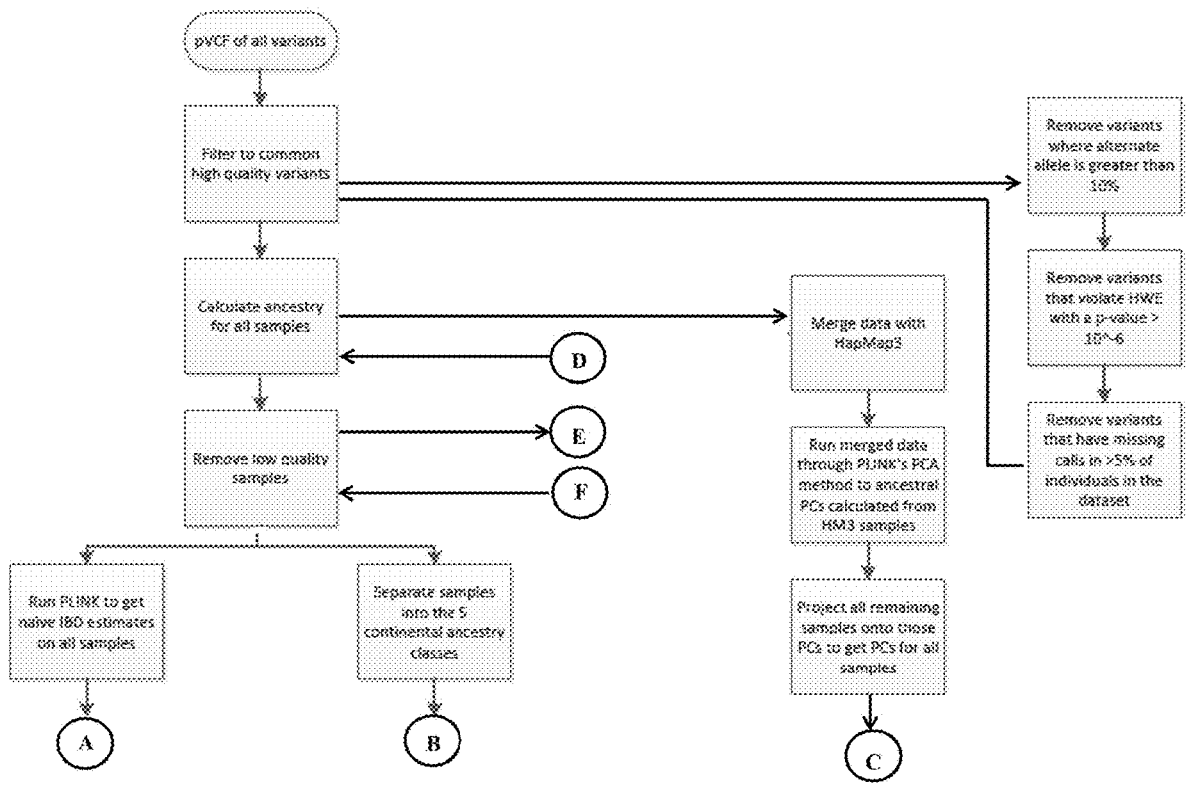
FIGS. 5A-D represent a flow chart of an exemplary embodiment wherein identity-by-descent is determined.
Figure 5B:
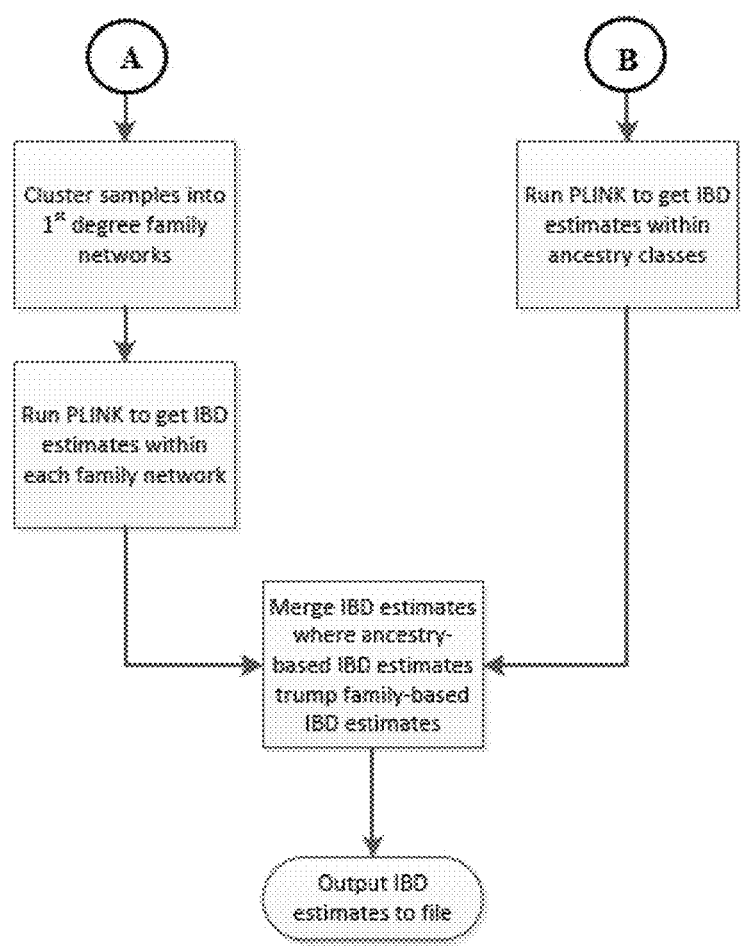
Figure 5C:
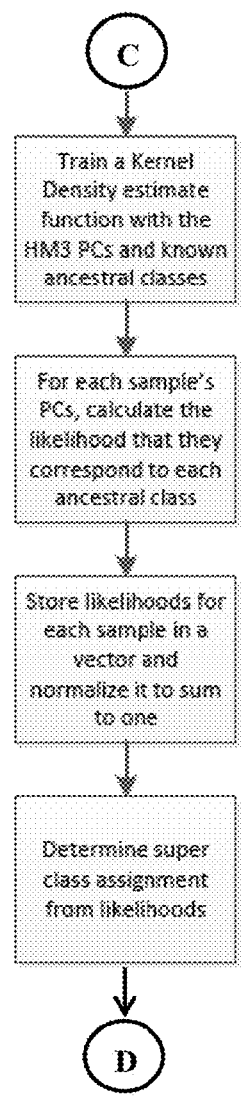
Figure 5D:
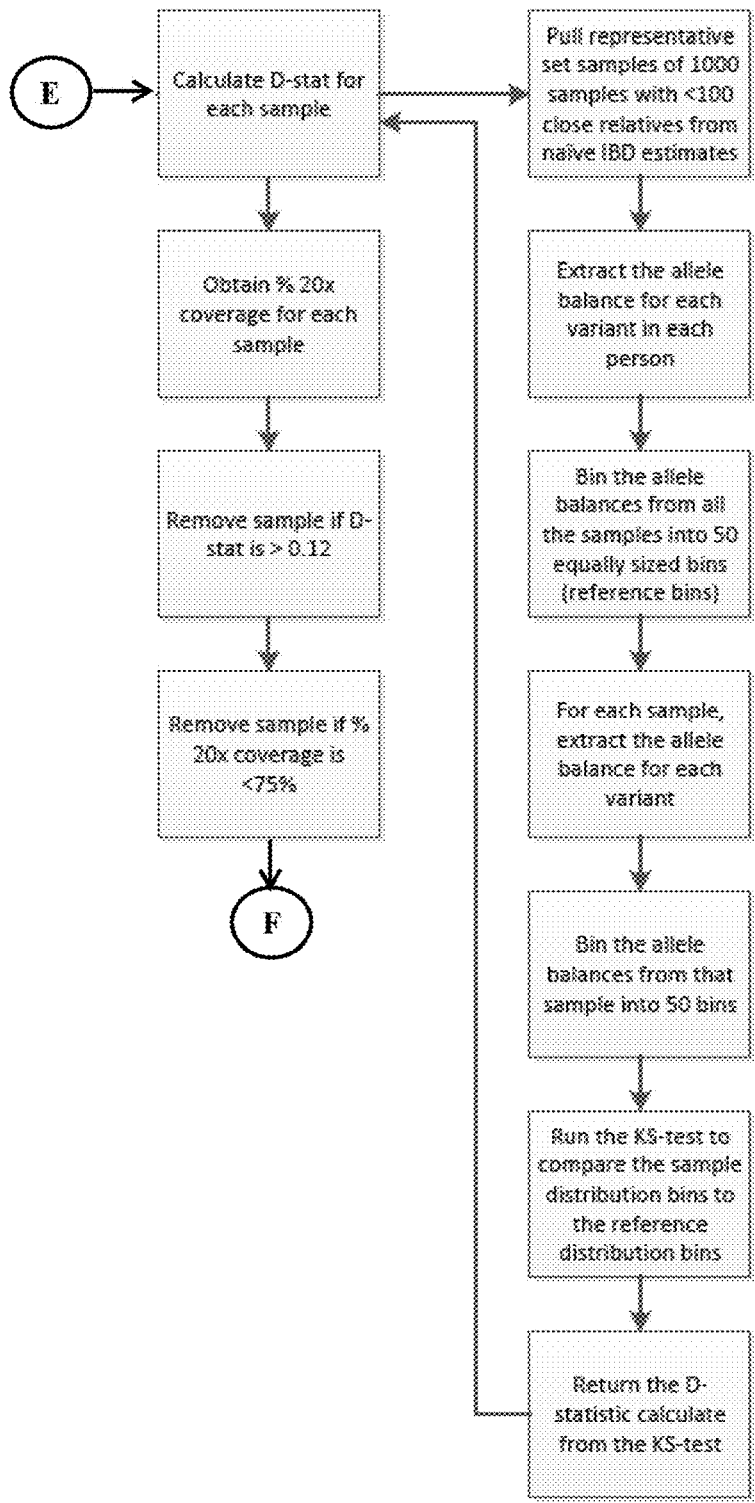

FIG. 3 is a flow chart of an exemplary embodiment wherein de novo mutations (DNMs) are identified in a population. An ancestral superclass designation for subjects based on identified variants may be established at step 23; first identity-by-descent estimates of subjects within an ancestral superclass may be generated at step 24; second identity-by-descent estimates of subjects independent from subjects' ancestral superclass may be generated at step 25; subjects may be clustered at step 26 into primary first-degree family networks based on one or more of the second identity-by-descent estimates; third identity-by-descent estimates of subjects within a primary first-degree family network may be generated at step 27; and first and third identity-by-descent estimates may be merged at step 28 to obtain merged identity-by-descent estimates by any suitable means. Non-limiting examples of such means include PLINK (Chang et al. (2015); Gigascience 4, 7), and those disclosed in the Examples. Identity-by-descent estimates may comprise genome-wide calculations of IBD 0, 1, and 2 values among sample pairs.

Moreover, nuclear families may be constructed at step 29 based on merged identity-by-descent estimates; variants in nuclear families may be identified at step 30; a genotype likelihood score may be assigned at step 31 to a variant in samples from each parent and child in a trio in a constructed nuclear family and a probability may be calculated that the variant is a de novo mutation, and independently a variant in a child sample may be naively identified that is not present in either parent sample in a trio and a probability may be calculated that the variant is a de novo mutation, and then both sets of probable de novo mutations may be combined, thereby forming a dataset of probable de novo mutations. Non-limiting examples of means to conduct the aforesaid steps include those disclosed in the Examples.

In some exemplary embodiments, the method further comprises filtering identified variants before ancestral superclass designations for subjects are established; and in some exemplary embodiments, the method further comprises filtering identified variants before second identity-by-descent estimates of subjects are generated. Variants may be filtered by any suitable means. Non-limiting examples of such means include PLINK (Chang et al. (2015); Gigascience 4, 7) and those disclosed in the Examples.

Filtering variants may comprise removing variants having alternate allele frequency greater than about 10% across the samples from the plurality of human subjects, or variants violating Hardy-Weinberg equilibrium (HWE) with a p-value >about $10^{-6}$, or variants having missing calls in >about 5% of the samples from the plurality of human subjects, or a combination thereof. Variants not satisfying certain selection criteria may be removed, remaining variants selected as potential compound heterozygous mutations and potential compound heterozygous mutations phased by any suitable means, including those described in the Examples.

In some exemplary embodiments, the method further comprises removing low-quality samples after identified variants have been filtered. Low-quality samples may be removed by any suitable means. Non-limiting examples of such means include those disclosed in Dewey et al. (2016), Science 354, aaf6814-1 to aaf6814-10, which are generally known and thus not further detailed herein, and those disclosed in the Examples. In some exemplary embodiments, the parameters are adjusted such that samples having a D-stat of >0.12 or 20× read coverage of <75%, or both, are low-quality samples that are removed. In some exemplary embodiments, D-stats of low-quality samples are determined by comparing the samples' distribution of actual allele balance with an expected distribution of allele balance using a KS test.

Merging first and third identity-by-descent estimates may comprise augmenting the first identity-by-descent estimates with pairwise identity-by-descent estimates unique to the third identity-by-descent estimates, which may be facilitated by, for example but not limited to, PLINK (Chang et al. (2015); Gigascience 4, 7), and those means disclosed in the Examples.

Filtering variants may comprise removing variants having a genotype quality (GQ) annotation in the child sample of less than about 35, or having an alternate allele count (AC) of 10 or greater across the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof. Classifying a probable de novo mutation as a moderate confidence de novo mutation may occur when the probable de novo mutation has an allele balance (AB) of about 15% or greater in the child sample and about 2% or less in each parent sample, and does not have a mapping quality (MQ) of less than about 40, and does not have a quality by depth (QD) value of less than about 2, and has minor allele count (MAC) of less than about 20 across the samples, and has about 3 soft-clipped reads or less at the variant site in the carrier of the probable de novo mutation, and is not an INDEL with a mono-polymer run of more than about 4. Classifying a moderate confidence de novo mutation as a high confidence de novo mutation may occur when the moderate confidence de novo mutation has a genotype quality (GQ) annotation in the parent sample of about 90 or greater, and has a read depth (DP) of about 10 or greater in each parent sample, and has an alternate DP of about 7 or greater in the child sample, and has QD greater than about 3 for SNPs, and has QD greater than about 5 for INDELs. These steps may be conducted by any suitable means, including those described in the Examples. These exemplary embodiments are also illustrated in FIG. 7.

The term D-stat as used herein refers to a QC metric that may be generated and used to identify low-quality samples. The low quality of a sample may be caused by contamination, which may cause problems with downstream analyses. A D-stat of a sample may be calculated, for example, by comparing the distribution of the actual allele balance of the sample with a reference allele balance distribution (e.g., an expected distribution of allele balance). The reference distribution may be calculated, for example, from a plurality of samples without any evidence of contamination which were captured and sequenced using the same platform as the one used to query the sample to be analyzed. The value of the D-stat QC metric as used herein is equivalent to the D statistic generated from a K-S (Kolmogorov-Smirnov) test prior to calculating a p-value. A D-stat does not have units. The D statistic from the K-S test results in a value between 0 and 1, with 1 signifying the maximum difference between the cumulative distributions of the reference distribution and the sample distribution. In some exemplary embodiments, low quality samples are identified by comparing the distribution of a sample's actual allele balance with an expected distribution/reference distribution of allele balance calculated according to a K-S test. In some exemplary embodiments, samples determined to have a specific D-stat value are considered low quality samples and removed from further analysis. In some exemplary embodiments, the D-stat value of a sample considered to be low quality and to be removed is >0.01, 0.02, 0.03, 0.04, 0.05, 0.06, 0.07, 0.08, 0.09, 0.1, 0.11, or 0.12. In a preferred embodiment, the D-stat value of a sample considered to be low quality and to be removed is >about 0.12. In an even more preferred embodiment, the D-stat value of a sample considered to be low quality and to be removed is >0.12.

Any of the methods described or exemplified may be practiced as a non-transitory computer-implemented method and/or as a system. Any suitable computer system known by the person having ordinary skill in the art may be used for this purpose.

Figure 10:
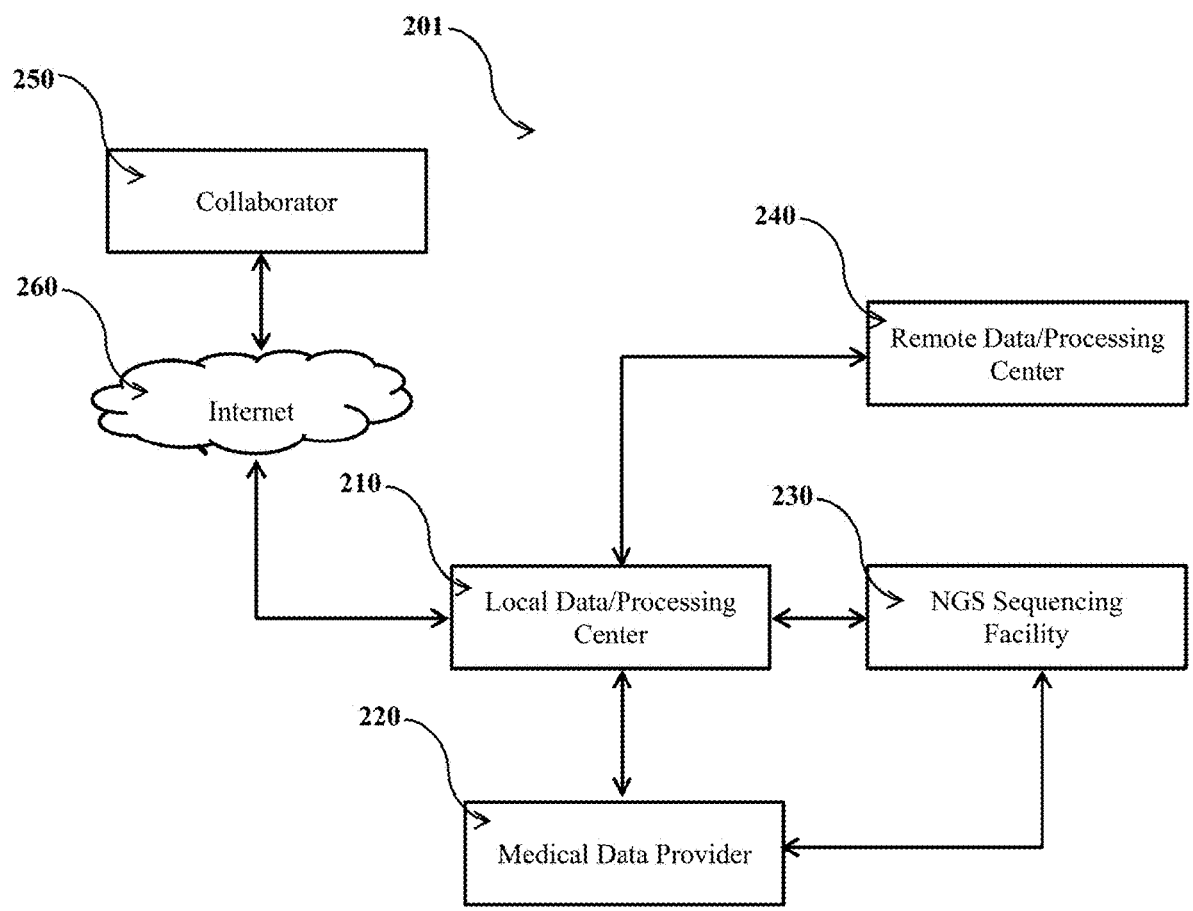
FIG. 10 is an exemplary operating environment.

FIG. 10 illustrates various aspects of an exemplary environment 201 in which the present methods and systems can operate. The present methods may be used in various types of networks and systems that employ both digital and analog equipment. Provided herein is a functional description and that the respective functions can be performed by software, hardware, or a combination of software and hardware.

The environment 201 can comprise a Local Data/Processing Center 210. The Local Data/Processing Center 210 can comprise one or more networks, such as local area networks, to facilitate communication between one or more computing devices. The one or more computing devices can be used to store, process, analyze, output, and/or visualize biological data. The environment 201 can, optionally, comprise a Medical Data Provider 220. The Medical Data Provider 220 can comprise one or more sources of biological data. For example, the Medical Data Provider 220 can comprise one or more health systems with access to medical information for one or more patients. The medical information can comprise, for example, medical history, medical professional observations and remarks, laboratory reports, diagnoses, doctors' orders, prescriptions, vital signs, fluid balance, respiratory function, blood parameters, electrocardiograms, x-rays, CT scans, MM data, laboratory test results, diagnoses, prognoses, evaluations, admission and discharge notes, and patient registration information. The Medical Data Provider 220 can comprise one or more networks, such as local area networks, to facilitate communication between one or more computing devices. The one or more computing devices can be used to store, process, analyze, output, and/or visualize medical information. The Medical Data Provider 220 can de-identify the medical information and provide the de-identified medical information to the Local Data/Processing Center 210. The de-identified medical information can comprise a unique identifier for each patient so as to distinguish medical information of one patient from another patient, while maintaining the medical information in a de-identified state. The de-identified medical information prevents a patient's identity from being connected with his or her particular medical information. The Local Data/Processing Center 210 can analyze the de-identified medical information to assign one or more phenotypes to each patient (for example, by assigning International Classification of Diseases "ICD" and/or Current Procedural Terminology "CPT" codes).

The environment 201 can comprise a NGS Sequencing Facility 230. The NGS Sequencing Facility 230 can comprise one or more sequencers (e.g., Illumina HiSeq 2500, Pacific Biosciences PacBio RS II, and the like). The one or more sequencers can be configured for exome sequencing, whole exome sequencing, RNA-seq, whole-genome sequencing, targeted sequencing, and the like. In an exemplary aspect, the Medical Data Provider 220 can provide biological samples from the patients associated with the de-identified medical information. The unique identifier can be used to maintain an association between a biological sample and the de-identified medical information that corresponds to the biological sample. The NGS Sequencing Facility 230 can sequence each patient's exome based on the biological sample. To store biological samples prior to sequencing, the NGS Sequencing Facility 230 can comprise a biobank (for example, from Liconic Instruments). Biological samples can be received in tubes (each tube associated with a patient), each tube can comprise a barcode (or other identifier) that can be scanned to automatically log the samples into the Local Data/Processing Center 210. The NGS Sequencing Facility 230 can comprise one or more robots for use in one or more phases of sequencing to ensure uniform data and effectively non-stop operation. The NGS Sequencing Facility 230 can thus sequence tens of thousands of exomes per year. In one aspect, the NGS Sequencing Facility 230 has the functional capacity to sequence at least 1000, 2000, 3000, 4000, 5000, 6000, 7000, 8000, 9000, 10,000, 11,000 or 12,000 whole exomes per month.

The biological data (e.g., raw sequencing data) generated by the NGS Sequencing Facility 230 can be transferred to the Local Data/Processing Center 210 which can then transfer the biological data to a Remote Data/Processing Center 240. The Remote Data/Processing Center 240 can comprise cloud-based data storage and processing center comprising one or more computing devices. The Local Data/Processing Center 210 and the NGS Sequencing Facility 230 can communicate data to and from the Remote Data/Processing Center 240 directly via one or more high capacity fiber lines, although other data communication systems are contemplated (e.g., the Internet). In an exemplary aspect, the Remote Data/Processing Center 240 can comprise a third party system, for example Amazon Web Services (DNAnexus). The Remote Data/Processing Center 240 can facilitate the automation of analysis steps, and allows sharing data with one or more Collaborators 250 in a secure manner. Upon receiving biological data from the Local Data/Processing Center 210, the Remote Data/Processing Center 240 can perform an automated series of pipeline steps for primary and secondary data analysis using bioinformatic tools, resulting in annotated variant files for each sample. Results from such data analysis (e.g., genotype) can be communicated back to the Local Data/Processing Center 210 and, for example, integrated into a Laboratory Information Management System (LIMS) can be configured to maintain the status of each biological sample.

The Local Data/Processing Center 210 can then utilize the biological data (e.g., genotype) obtained via the NGS Sequencing Facility 230 and the Remote Data/Processing Center 240 in combination with the de-identified medical information (including identified phenotypes) to identify associations between genotypes and phenotypes. For example, the Local Data/Processing Center 210 can apply a phenotype-first approach, where a phenotype is defined that may have therapeutic potential in a certain disease area, for example extremes of blood lipids for cardiovascular disease. Another example is the study of obese patients to identify individuals who appear to be protected from the typical range of comorbidities. Another approach is to start with a genotype and a hypothesis, for example that gene X is involved in causing, or protecting from, disease Y.

In an exemplary aspect, the one or more Collaborators 250 can access some or all of the biological data and/or the de-identified medical information via a network such as the Internet 260.

Figure 11:
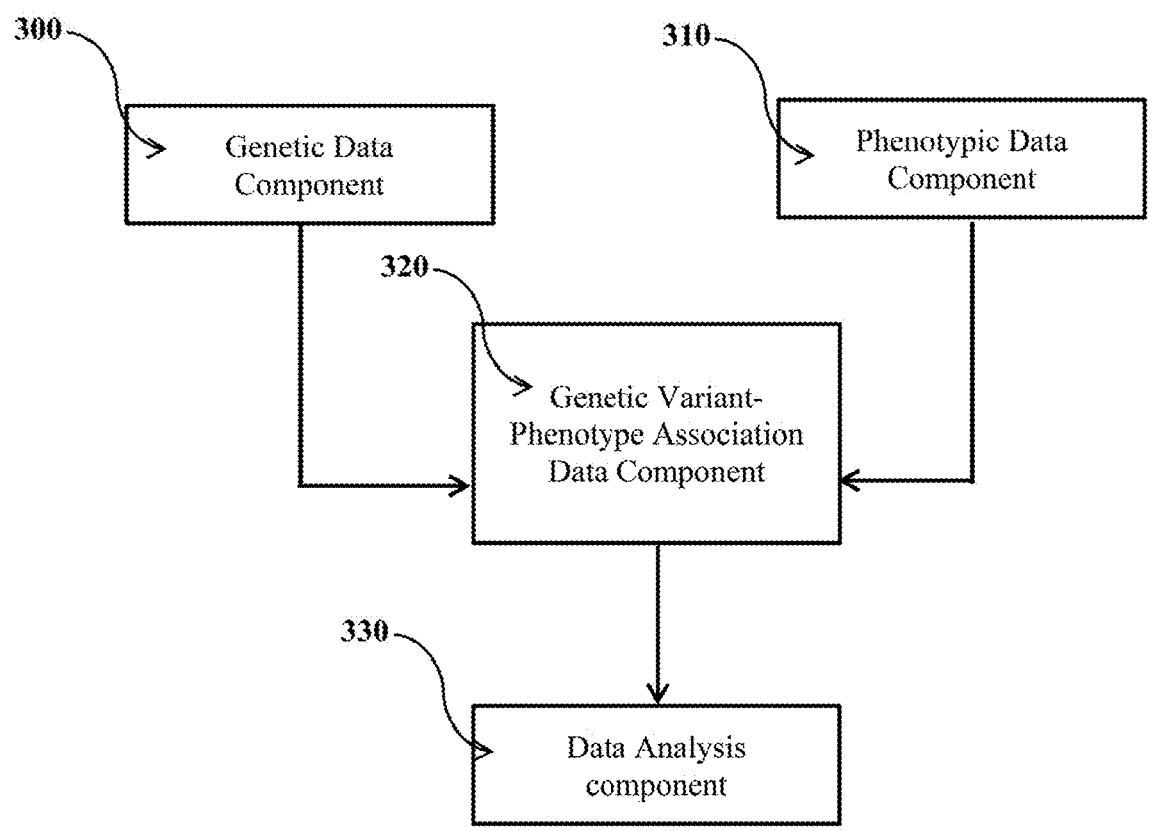
FIG. 11 illustrates a plurality of system components configured for performing the disclosed methods.

In an exemplary aspect, illustrated in FIG. 11, one or more of the Local Data/Processing Center 210 and/or the Remote Data/Processing Center 240 can comprise one or more computing devices that comprise one or more of a genetic data component 300, a phenotypic data component 310, a genetic variant-phenotype association data component 320, and/or a data analysis component 330. The genetic data component 300, the phenotypic data component 310, and/or the genetic variant-phenotype association data component 320 can be configured for one or more of, a quality assessment of sequence data, read alignment to a reference genome, variant identification, annotation of variants, phenotype identification, variant-phenotype association identification, data visualization, combinations thereof, and the like.

In an exemplary aspect, one or more of the components may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., non-transitory computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

In an exemplary aspect, the genetic data component 300 can be configured for functionally annotating one or more genetic variants. The genetic data component 300 can also be configured for storing, analyzing, receiving, and the like, one or more genetic variants. The one or more genetic variants can be annotated from sequence data (e.g., raw sequence data) obtained from one or more patients (subjects). For example, the one or more genetic variants can be annotated from each of at least 100,000, 200,000, 300,000, 400,000 or 500,000 subjects. A result of functionally annotating one or more genetic variants is generation of genetic variant data. By way of example, the genetic variant data can comprise one or more Variant Call Format (VCF) files. A VCF file is a text file format for representing SNP, indel, and/or structural variation calls. Variants are assessed for their functional impact on transcripts/genes and potential loss-of-function (pLoF) candidates are identified. Variants are annotated with snpEff using the Ensembl75 gene definitions and the functional annotations are then further processed for each variant (and gene).

The consecutive labeling of method steps as provided herein with numbers and/or letters is not meant to limit the method or any exemplary embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, in this document.

The disclosure will be more fully understood by reference to the following Examples, which are provided to describe the disclosure in greater detail. They are intended to illustrate and should not be construed as limiting the scope of the disclosure.

EXAMPLES

Example 1.1

Relationship Estimation and Relatedness Description in a Cohort of 61K Human Exomes A cohort of 61K human exomes was analyzed. This cohort originated from a study by the Regeneron Genetics Center (RGC) and the Geisinger Health System (GHS) initiated in 2014 (Dewey et al. (2016), Science 354, aaf6814-aaf6814). This DiscovEHR study densely sampled patients in a single healthcare system that serves a population with low migration rates. The 61K human exomes cohort is referred herein as the DiscovEHR dataset. A tremendous amount of family structure was identified within the DiscovEHR dataset, and simulations disclosed herein projected that 70%-80% of the individuals in the dataset will have a first- or second-degree relative when the study ascertains the target of 250K people.

Identity-by-decent (IBD) estimates were used to identify the different types of familial relationships within the dataset, and PRIMUS (Staples et al. (2014), Am. J. Hum. Genet. 95, 553-564) was used to classify the pairwise relationships into different familial classes and to reconstruct the pedigrees (further explained in Example 8). Due to the limitations of accurately estimating IBD proportions for distant relatives from whole-exome sequencing (WES) data, only the estimated first-degree, second-degree, and high-confidence third-degree relationships among the DiscovEHR dataset samples were included.

Figure 12A:
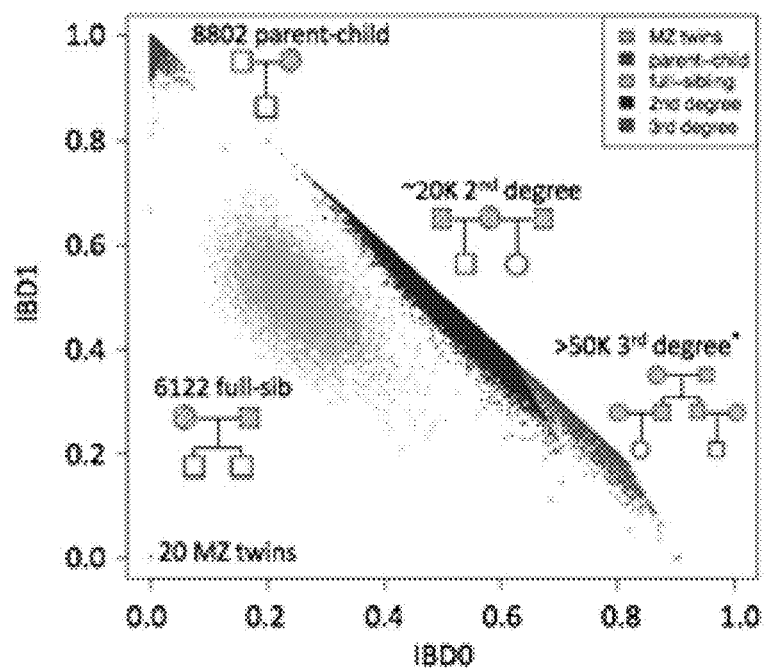
FIGS. 12A, 12B, 12C, and 12D illustrate the relatedness found in the first 61K sequenced individuals from the DiscovEHR cohort according to an exemplary embodiment. Panel A shows IBD0 vs IBD1 plot; Panel B: shows a histogram plotting the size distribution of first-degree family networks in the cohort analyzed; Panel C shows first-degree family network pedigree containing 25 sequenced individuals that was reconstructed from the pairwise-IBD estimates; and Panel D shows a scheme depicting the largest second-degree family network of 7,084 individuals.
Figure 12B:
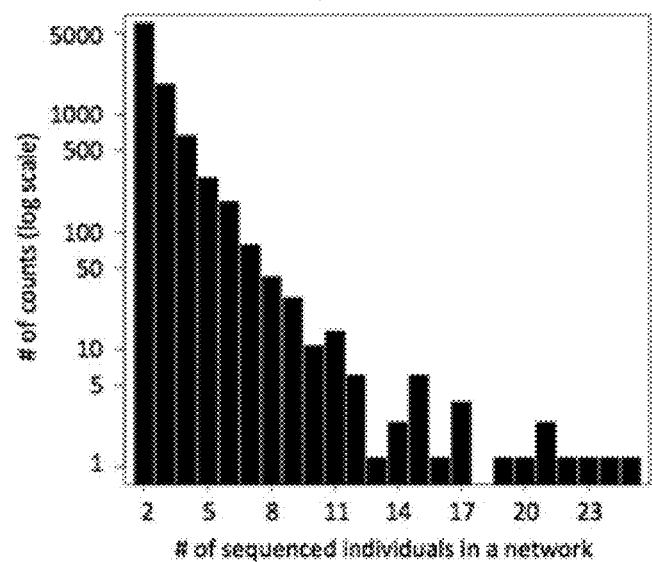

In total, 20 monozygotic twins, 8,802 parent child relationships, 6,122 full-sibling relationships, and ~20,000 second-degree relationships were identified within the dataset (FIG. 12A). Since the IBD sharing distributions of second- and third-degree relationships overlap with each other, a hard cutoff halfway between the two expected means was selected for this study. Third-degree relationships (marked by an asterisk in FIG. 12A) are challenging to accurately estimate due to technical limitations of exome data as well as the widening and overlapping variation around the expected mean IBD proportions of more distant relationship classes (e.g. fourth-degree and fifth degree). Next, individuals were treated as nodes and relationships as edges to generate undirected graphs. Using only first-degree relationships, 7,684 connected components were identified, which were referred to as first-degree family networks. FIG. 12B, shows the distribution in size of the first-degree family networks, which range from 2 to 25 sequenced individuals. Similarly, 7,136 second-degree family networks were found; the largest containing 7,123 individuals (~12% of the overall dataset; FIG. 12D). In FIG. 12D, first-degree family networks within the second-degree family network are depicted as red boxes proportionally sized to the number of individuals in the network (including the first-degree family network pedigree shown in FIG. 12C). Single individuals are depicted as black nodes connected by second-degree relationships, which are drawn as blue edges.

Approximately 4,500 third-degree relationships could also be identified within the second-degree family networks. Relaxing the minimum IBD cutoff for the IBD estimations within ancestral groups indicated, well over 50K 3rd degree relationships within the DiscovEHR dataset were identified. While individuals of European ancestries only make up 96.5% of DiscovEHR dataset (See Table 1a below), the vast majority (>99%) of the pairwise relationships found in the dataset involve individuals of European ancestry (See Table 1b below). Regardless, there are many relationships between people of the same, non-European ancestry and between individuals with different ancestries. For example, trios were found in the DiscovEHR dataset with a European father and an East Asian mother whose child was assigned an unknown ancestry because it did not closely match a reference population.

TABLE 1a (Ancestral breakdown of the DiscovEHR dataset)

| Ancestry class | # of sample | % of people |
|---|---|---|
| EUR | 58901 | 96.5% |
| AFR | 1192 | 2.0% |
| AMR | 513 | 0.8% |
| SAS | 110 | 0.2% |
| EAS | 106 | 0.2% |
| UNKNOWN | 197 | 0.3% |

TABLE 1b (complete breakdown of the ancestral backgrounds of individuals involved in first and second-degree relationships)

| relationship | ancestries | count |
|---|---|---|
| MZ twins | EUR | 20 |
| parent-child | EUR | 8573 |
| parent-child | AFR-EUR | 81 |
| parent-child | AMR-EUR | 43 |
| parent-child | AFR | 38 |
| parent-child | EUR-UNKNOWN | 18 |
| parent-child | AMR | 10 |
| parent-child | AMR-UNKNOWN | 7 |
| parent-child | EAS-UNKNOWN | 8 |
| parent-child | SAS | 7 |
| parent-child | UNKNOWN | 6 |
| parent-child | AFR-UNKNOWN | 5 |
| parent-child | AFR-AMR | 3 |
| parent-child | EAS | 1 |
| full-sibling | EUR | 6043 |
| full-sibling | AFR-EUR | 41 |
| full-sibling | AFR | 22 |
| full-sibling | AMR-EUR | 8 |
| full-sibling | UNKNOWN | 5 |
| full-sibling | AMR | 4 |
| full-sibling | AMR-UNKNOWN | 1 |
| full-sibling | EAS-UNKNOWN | 1 |
| 2nd-degree | EUR | 20461 |
| 2nd-degree | AFR-EUR | 50 |
| 2nd-degree | AFR | 41 |
| 2nd-degree | AMR-EUR | 17 |
| 2nd-degree | AMR | 10 |
| 2nd-degree | EUR-UNKNOWN | 5 |
| 2nd-degree | AFR-AMR | 1 |
| 2nd-degree | EAS | 1 |
| 2nd-degree | EAS-UNKNOWN | 1 |
| 2nd-degree | SAS | 1 |
| 3rd-degree | EUR | 1971 |
| 3rd-degree | AFR-EUR | 23 |
| 3rd-degree | AMR-EUR | 9 |
| 3rd-degree | AFR-AFR | 3 |
| 3rd-degree | EUR-UNKNOWN | 1 |
| all | EUR | 37069 |
| all | AFR-EUR | 195 |
| all | AFR | 104 |
| all | AMR-EUR | 77 |
| all | AMR | 24 |
| all | EUR-UNKNOWN | 24 |
| all | UNKNOWN-UNKNOWN | 11 |
| all | EAS-UNKNOWN | 10 |
| all | AMR-UNKNOWN | 8 |
| all | SAS-SAS | 8 |
| all | AFR-UNKNOWN | 5 |
| all | AFR-AMR | 4 |
| all | EAS-EAS | 2 |

Figure 13A:
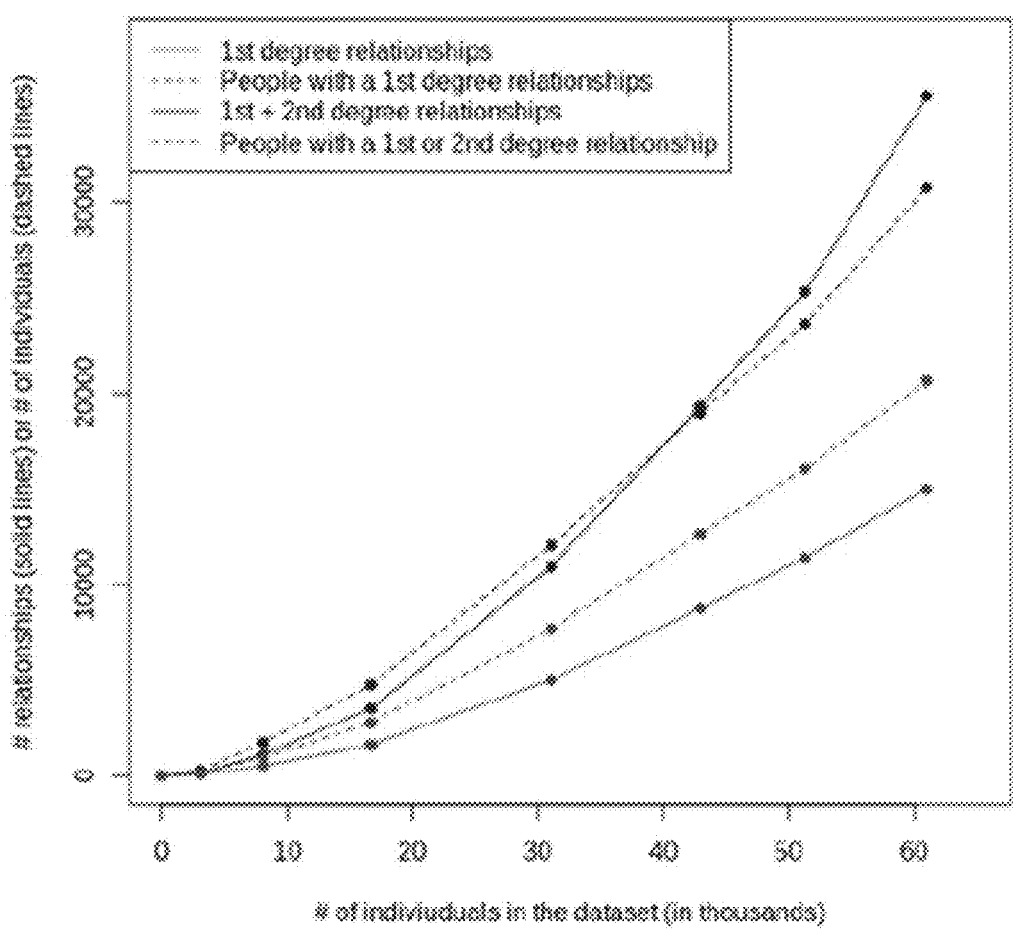
FIGS. 13A and 13B illustrate the accumulation of relatedness within the DiscovEHR cohort as a function of the number of ascertained individuals in the dataset ascertained by an exemplary embodiment.
Figure 13B:
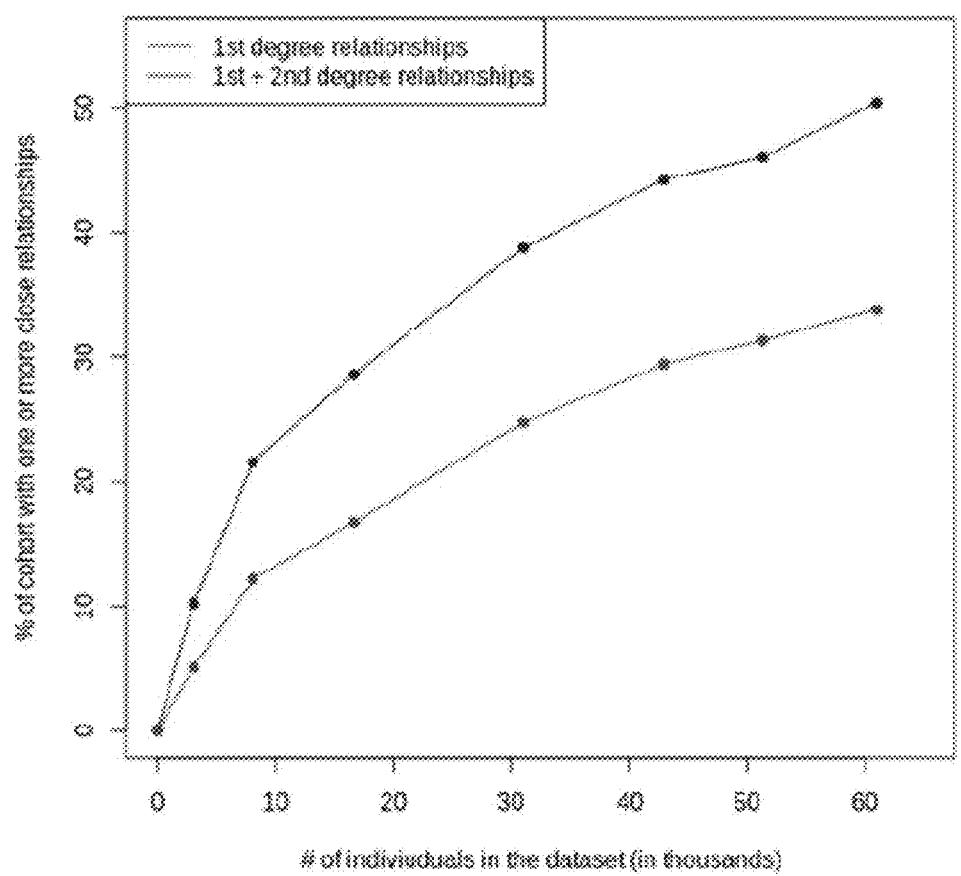

The rate of accumulating relatives far exceeded the rate with which samples were ascertained empirically (FIG. 13A) and through simulation (FIG. 14A) that the rate of accumulating relatives far exceeded the rate of ascertaining samples. The accumulation of additional pairwise relationships resulted in more individuals being involved in these relationships. Currently, 50.4% of the 61K individuals have one or more first- or second-degree relatives in the DiscovEHR dataset (FIG. 13B).

Example 1.2

Relationship Estimation and Relatedness Description in a Cohort of 92K Human Exomes A larger clinical cohort of 92,455 human exomes was analyzed. This cohort originated from the ongoing study by the Regeneron Genetics Center (RGC) and the Geisinger Health System (GHS) initiated in 2014 (Staples et al. (2018), Am. J. Hum. Genet. 102(5): 874-889). This expanded DiscoverEHR cohort is also a dense sample of participants from a single healthcare system that serves a largely rural population with low migration rate in central Pennsylvania.

The set containing the prepared and sequenced first 61K samples (example 1.1) was referred to as "VCRome set". The remaining set of 31K samples were prepared by the same process, except that in place of the NimbleGen probed capture, a slightly modified version of IDT's xGen probes was used wherein supplemental probes were used to capture regions of the genome covered by the NimbleGen VCRome capture reagent but poorly covered by the standard xGen probes. Captured fragments were bound to streptavidin-conjugated beads, and non-specific DNA fragment were removed by a series of stringent washes according to the manufacturer's (IDT's) recommended protocol. This second set of samples was referred to as the "xGen set." Variant calls were produced with the GATK. GATK was used for local realignment of the aligned, duplicate-marked reads of each sample around putative indels. GATK's HaplotypeCaller was used to process the INDEL realigned, duplicate-marked reads to identify all exonic positions at which a sample varied from the genome reference in the genomic variant call format (gVCF). Genotyping was accomplished with GATK's GenotypeGVCFs on each sample and a training set of 50 randomly selected samples outputting a single-sample variant call format (VCF) file identifying both single-nucleotide variants (SNVs) and indels as compared to the reference. The single-sample VCF files were then used to create a pseudo-sample that contained all variable sites from the single-sample VCF files in both sets. Further, independent pVCF files for the VCRome set by joint calling 200 single-sample gVCF files with the pseudo-sample to force a call or no-call for each sample at all variable sites across the two capture sets. All 200-sample pVCF files were combined to create the VCRome pVCF file and this process was repeated to create the xGen pVCF file. The VCRome and xGen pVCF files were combined to create the union pVCF file. The sequence reads to GRCh38 were aligned and variants were annotated by using Ensembl 85 gene definitions. The gene definitions were restricted to 54,214 transcripts, corresponding to 19,467 genes, that are protein-coding with an annotated start and stop. After the sample QC process, 92,455 exomes remained for analysis.

Figure 17A:
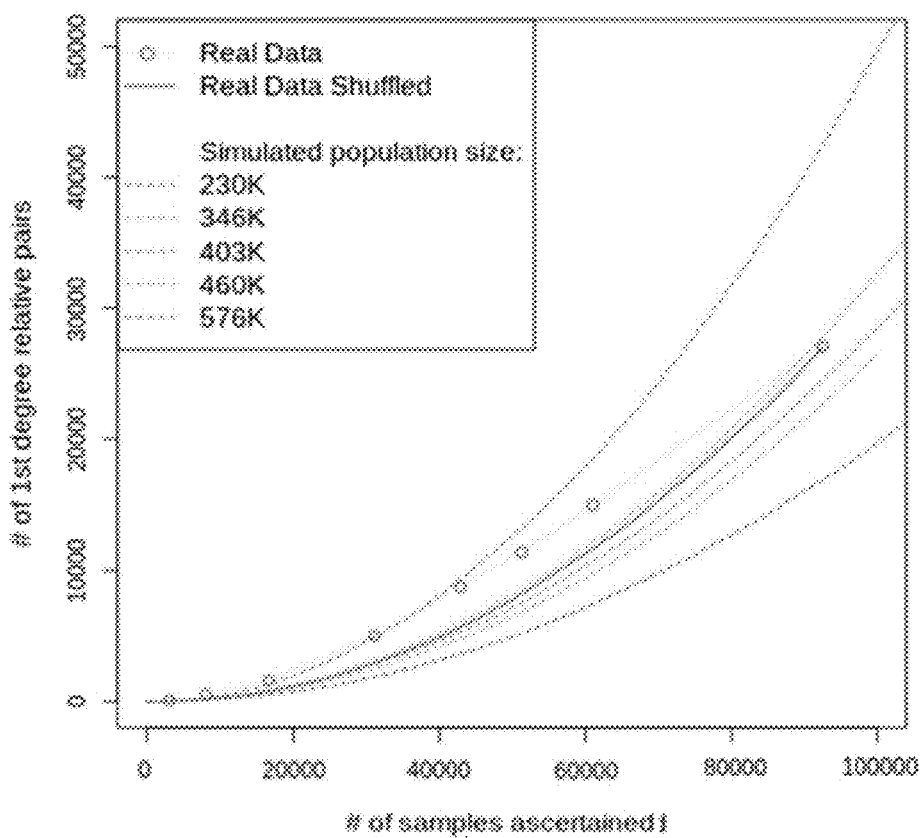

From the expanded DiscovEHR dataset of 92,455 individuals, 43 monozygotic twins, 16,476 parent-child relationships, 10,479 full-sibling relationships, and 39,000 second-degree relationships were identified (FIG. 16, panel A). Individuals were treated as nodes and relationships as edges to generate undirected graphs. Using only first-degree relationships, 12,594 connected components were identified, which are referred to as first degree family networks. FIG. 16, panel B shows the distribution in size of the first-degree family networks, which range from 2 to 25 sequenced individuals. Similarly, 10,173 second-degree family networks, the largest containing 19,968 individuals (22% of the overall dataset; FIG. 16, panel C) were identified. About 5,300 third-degree relationships within the second-degree family networks were also identified. Using a lower IBD cutoff (PIJ_HAT>0.09875) for the IBD estimations within ancestral groups without consideration of second-degree family networks, over 100,000 third-degree relationships were identified within the expanded DiscovEHR cohort. Given that 95.9% of expanded DiscovEHR individuals were of European ancestry (Table 2a), it is not surprising that the vast majority (98.6%) of the pairwise relationships found were between two individuals of European ancestry (Table 2b). Nonetheless, many relationships between people of the same, non-European ancestry and between individuals with different ancestries were identified; for example, there were several trios having one European parent, one East Asian parent, and a child whose ancestry was unassigned to a super-population because of the admixed nature of his or her genome. Importantly, empirically (FIG. 17A) and through simulation (FIG. 18A), it was determined that the rate of accumulating relatives far exceeded the rate of ascertaining samples. This was expected, given that there are combinatorially increasing numbers of possible pairwise relationships within the dataset as the size increases and that the likelihood that a previously unrelated individual in the dataset becomes involved in a newly identified relationship also increases. Currently, 39% of individuals in the expanded DiscovEHR cohort could have at least one first-degree relative in the dataset, and 56% of the participants have one or more first- or second-degree relatives in the dataset (FIG. 17, panel B).

TABLE 2a (Ancestral breakdown of the expanded DiscovEHR dataset)

| Ancestry class | # of sample | % of people |
|---|---|---|
| EUR | 88634 | 95.9% |
| AFR | 1984 | 2.1% |
| AMR | 959 | 1.0% |
| SAS | 196 | 0.2% |
| EAS | 194 | 0.2% |
| UNKNOWN | 488 | 0.5% |

TABLE 2b (complete breakdown of the ancestral backgrounds of individuals involved in first and second-degree relationships in the expanded DiscovEHR dataset)

| relationship | ancestries | count |
|---|---|---|
| MZ twins | EUR-EUR | 42 |
| MZ twins | SAS-SAS | 1 |
| Parent-child | EUR-EUR | 16028 |
| Parent-child | AFR-AFR | 115 |
| Parent-child | AFR-EUR | 86 |
| Parent-child | AMR-EUR | 83 |
| Parent-child | AMR-AMR | 43 |
| Parent-child | EUR-UNKNOWN | 43 |
| Parent-child | UNKNOWN-UNKNOWN | 20 |
| Parent-child | AFR-UNKNOWN | 13 |
| Parent-child | AMR-UNKNOWN | 13 |
| Parent-child | EAS-UNKNOWN | 13 |
| Parent-child | SAS-SAS | 11 |
| Parent-child | AFR-AMR | 5 |
| Parent-child | EUR-SAS | 2 |
| Parent-child | EAS-SAS | 1 |
| full-sibling | EUR-EUR | 10364 |
| full-sibling | AFR-AFR | 155 |
| full-sibling | AMR-EUR | 24 |
| full-sibling | AMR-AMR | 16 |
| full-sibling | UNKNOWN-UNKNOWN | 10 |
| full-sibling | AMR-UNKNOWN | 4 |
| full-sibling | SAS-SAS | 2 |
| full-sibling | EAS-EAS | 1 |
| full-sibling | EAS-UNKNOWN | 1 |
| full-sibling | EUR-SAS | 1 |
| full-sibling | EUR-UNKNOWN | 1 |
| 2nd-degree | EUR-EUR | 38746 |
| 2nd-degree | AFR-AFR | 163 |
| 2nd-degree | AFR-EUR | 57 |
| 2nd-degree | AMR-EUR | 41 |
| 2nd-degree | AMR-AMR | 23 |
| 2nd-degree | EUR-UNKNOWN | 23 |
| 2nd-degree | UNKNOWN-UNKNOWN | 17 |

TABLE 2b-continued (complete breakdown of the ancestral backgrounds of individuals involved in first and second-degree relationships in the expanded DiscovEHR dataset)

| relationship | ancestries | count |
|---|---|---|
| 2nd-degree | AFR-UNKNOWN | 3 |
| 2nd-degree | AFR-AMR | 2 |
| 2nd-degree | AMR-UNKNOWN | 1 |
| 2nd-degree | EAS-EAS | 1 |
| 2nd-degree | SAS-SAS | 1 |
| 3rd-degree | EUR-EUR | 5183 |
| 3rd-degree | AFR-EUR | 39 |
| 3rd-degree | AFR-AFR | 24 |
| 3rd-degree | AMR-EUR | 19 |
| 3rd-degree | EUR-UNKNOWN | 13 |
| 3rd-degree | AMR-AMR | 3 |
| 3rd-degree | AFR-UNKNOWN | 2 |
| 3rd-degree | AMR-UNKNOWN | 1 |
| all | EUR-EUR | 70363 |
| all | AFR-AFR | 357 |
| all | AFR-EUR | 182 |
| all | AMR-EUR | 167 |
| all | AMR-AMR | 85 |
| all | EUR-UNKNOWN | 80 |
| all | UNKNONW-UNKNOWN | 47 |
| all | AMR-UNKNOWN | 19 |
| all | AFR-UNKNOWN | 18 |
| all | SAS-SAS | 15 |
| all | EAS-UNKNOWN | 14 |
| all | AFR-AMR | 7 |
| all | EAS-EAS | 3 |
| all | EUR-SAS | 3 |

Example 2

Simulations with SimProgeny and Relatedness Projections

In an attempt to model, understand, and predict the growth of the relationship networks in the DiscovEHR and the expanded DiscovEHR dataset, a simulation framework (hereinafter "SimProgeny") was developed, which could simulate lineages of millions of people over hundreds of years dispersed across multiple sub-populations. From these simulated populations, it can model various sampling approaches, and estimate the amount of relatedness researchers should expect to find for a given set of populations and sampling parameters (See Example 17).

Figure 14A:
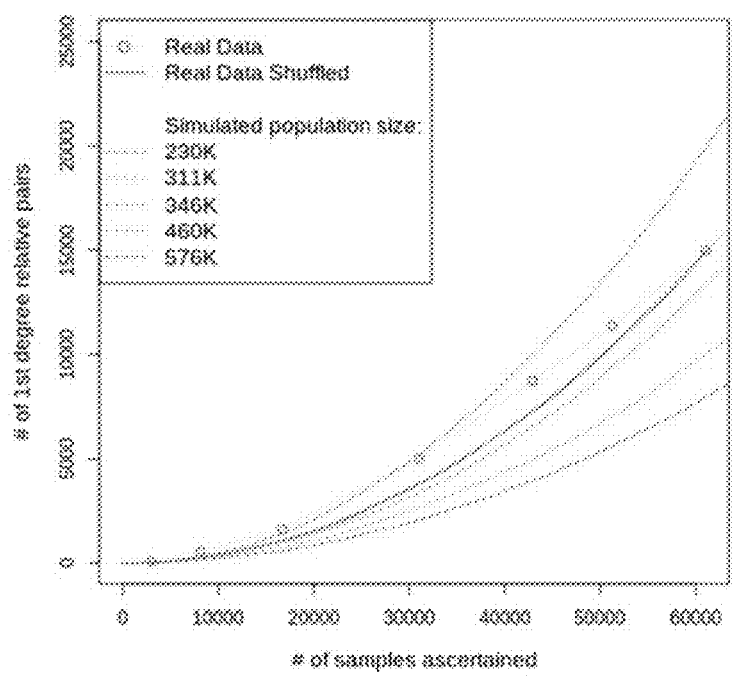
FIGS. 14A and 14B show a comparison between the ascertainment of first-degree relatives among 61K DiscovEHR participants and random ascertainment of simulated populations according to an exemplary embodiment. Panel A shows ascertainment of first-degree relative pairs and Panel B shows ascertainment of number of individuals with more than one first-degree relatives.
Figure 14B:
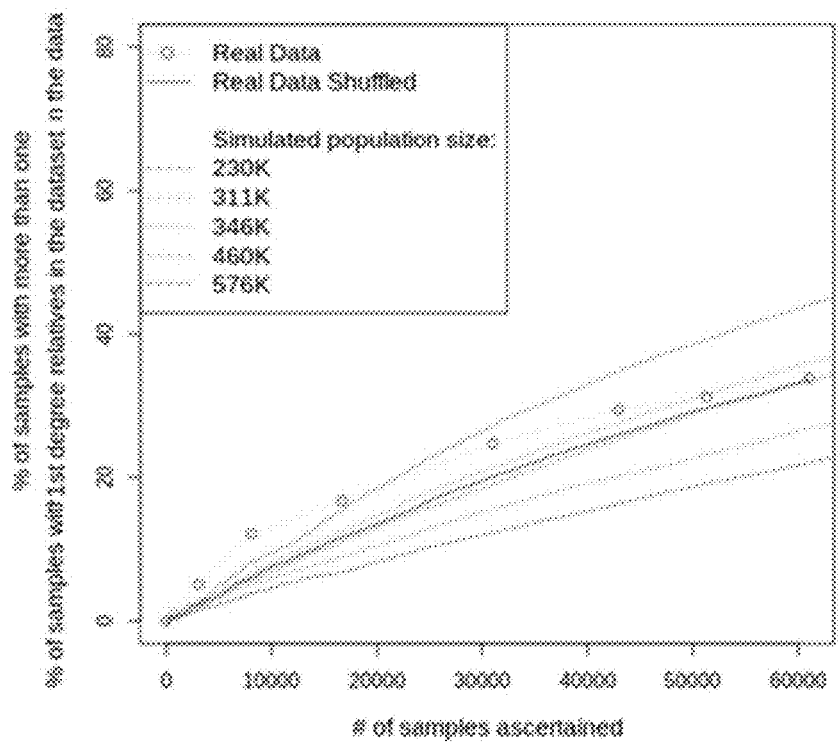
Figure 16A:
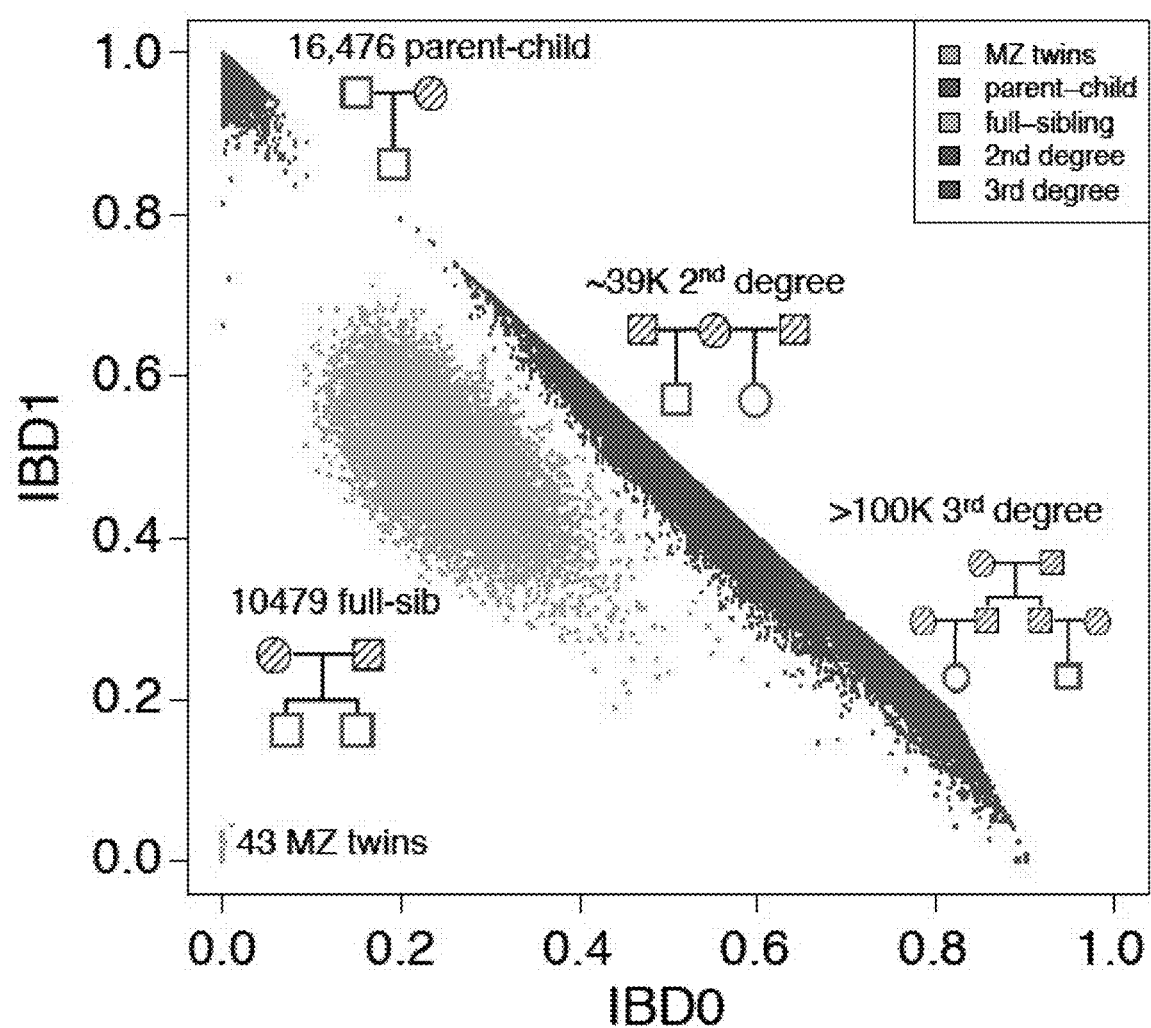
FIGS. 16A, 16B, 16C, and 16D illustrate the first 92K sequenced individuals from the expanded DiscovEHR cohort ascertained according to an exemplary embodiment. Panel A shows IBD0 vs IBD1 plot; Panel B shows histogram plotting the size distribution of first-degree family networks in the cohort analyzed; Panel C shows first-degree family network pedigree containing 25 sequenced individuals that was reconstructed from the pairwise-IBD estimates; and Panel D shows a scheme depicting the largest second-degree family network of 7,084 individuals.
Figure 16B:
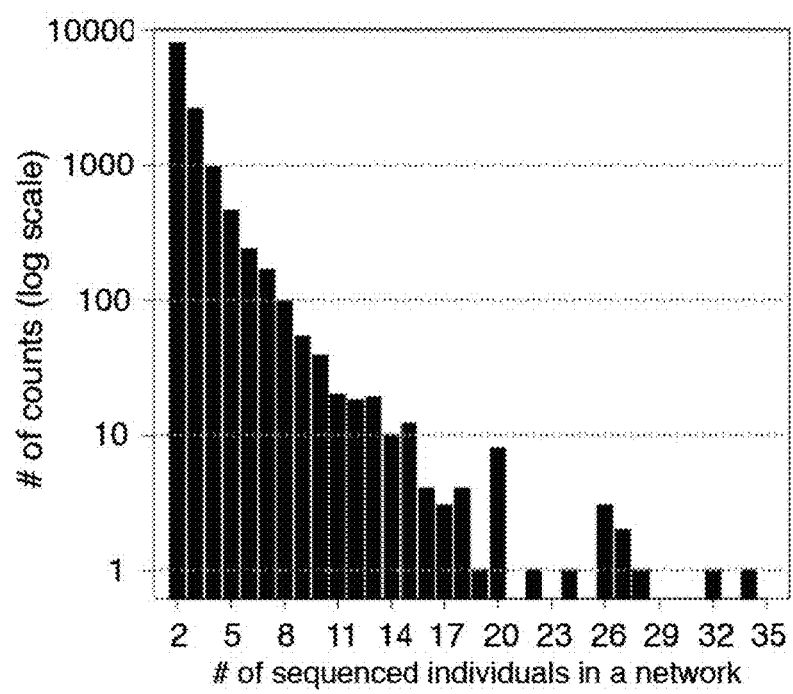
Figure 16C:
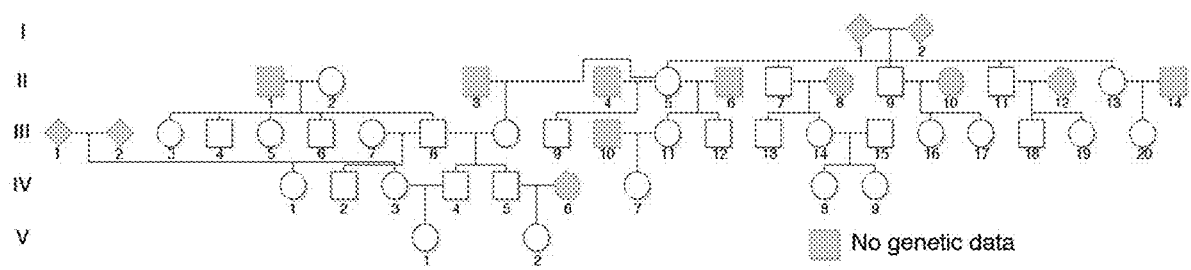
Figure 16D:
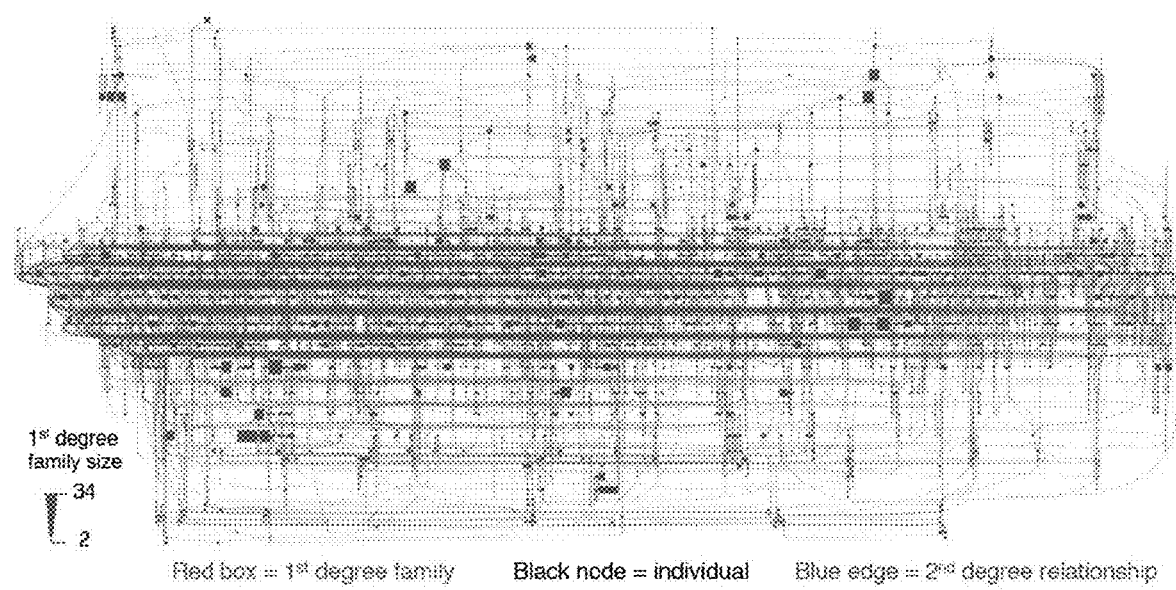

SimProgeny was used to simulate the DiscovEHR and the expanded DiscovEHR population and the ascertainment of the first 61K and first 92K participants from them, respectively. The simulations show that DiscovEHR and the expanded DiscovEHR participants were not randomly sampled from the population, but rather that the dataset was enriched for close relatives. As shown in FIGS. 14A and 14B, the real data were calculated at periodic "freezes" indicated with the punctuation points connected by the faint line. Samples and relationships identified in the 61K-person freeze were also taken and then shuffled the ascertainment order to demonstrate that the first half of the 61K DiscovEHR participants were enriched for first-degree relationships relative to the second half. Populations of various sizes were simulated using parameters similar to the real population from which DiscovEHR was ascertained. Random ascertainment from each of these populations was then performed to see which population size most closely fit the real data. A key takeaway is that none of these population sizes fit the real data and the random ascertainment approach is a poor fit. A different ascertainment approach that enriches for first-degree relatives compared to random ascertainment could produce a better fit. FIG. 14A shows that an ascertainment of first-degree relative pairs in an effective sampling population of size 270K closely fit the shuffled version of the real data, but underestimates the number of relative pairs below 61K ascertained participants and dramatically over estimates the number of relative pairs above 61K participants. FIG. 14B shows that a population of 270K most closely fits the shuffled real data with respect to the number of individuals with one or more first-degree relatives, but is a poor fit to the real data.

A similar result was observed using the expanded DiscovEHR dataset (FIG. 17A and FIG. 17B). Samples and relationships identified in the 92K-person freeze were then shuffled to demonstrate that the first half of the 92K expanded DiscovEHR participants were enriched for first-degree relationships relative the second half. Random ascertainment from each of these populations was then performed to see which population size most closely fit the real data. FIG. 17A shows that an ascertainment of first-degree relative pairs in an effective sampling population of size 403K closely fit the shuffled version of the real data, but underestimates the number of relative pairs below 92K ascertained participants and dramatically over estimates the number of relative pairs above 92K participants. FIG. 17B shows that a population of 403K most closely fits the shuffled real data with respect to the number of individuals with one or more first-degree relatives, but is a poor fit to the real data suggesting that the expanded DiscovEHR participants were not ascertained randomly.

Figure 18A:
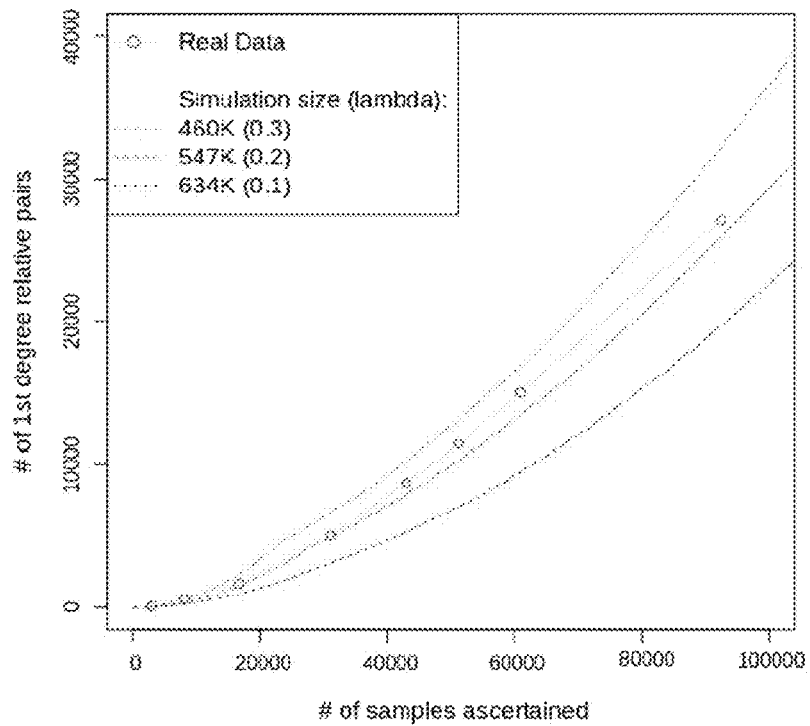
FIGS. 18A, 18B, 18C, and 18D show a simulated population and ascertainment fit to the accumulation of first-degree relatedness, in the expanded DiscovEHR cohort, according to an exemplary embodiment. Panel A shows accumulation of pairs of first-degree relatives; Panel B shows the proportion of the ascertained participants that have one or more first-degree relatives; Panel C sows simulated ascertainment projections with upper and lower bounds of the number of first-degree relationships; and Panel D shows simulated projections with upper and lower bounds of the proportion of the ascertained participants that have 1 or more first-degree relatives.
Figure 18B:
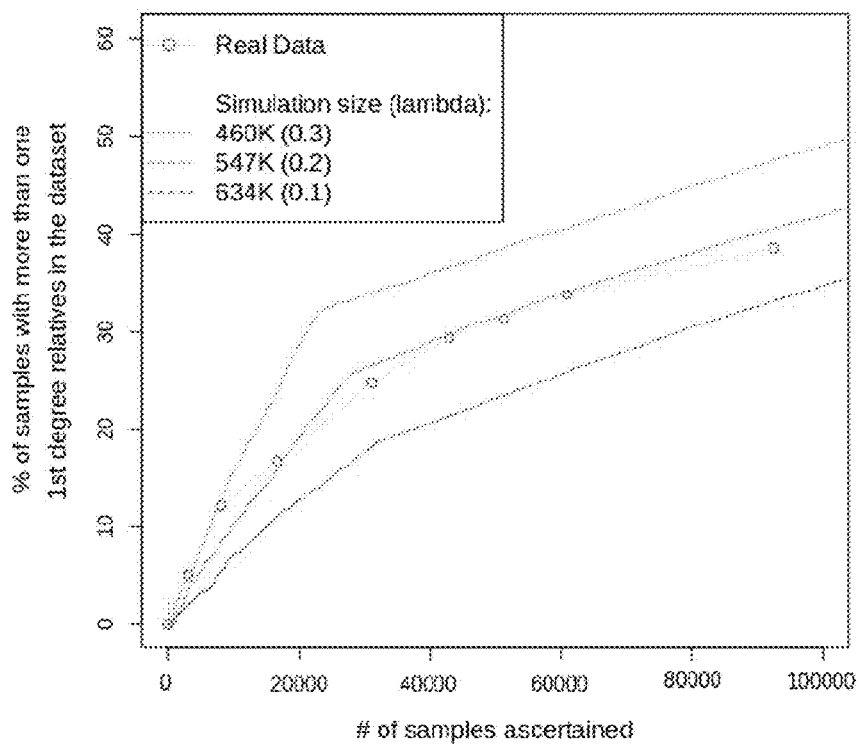
Figure 18C:
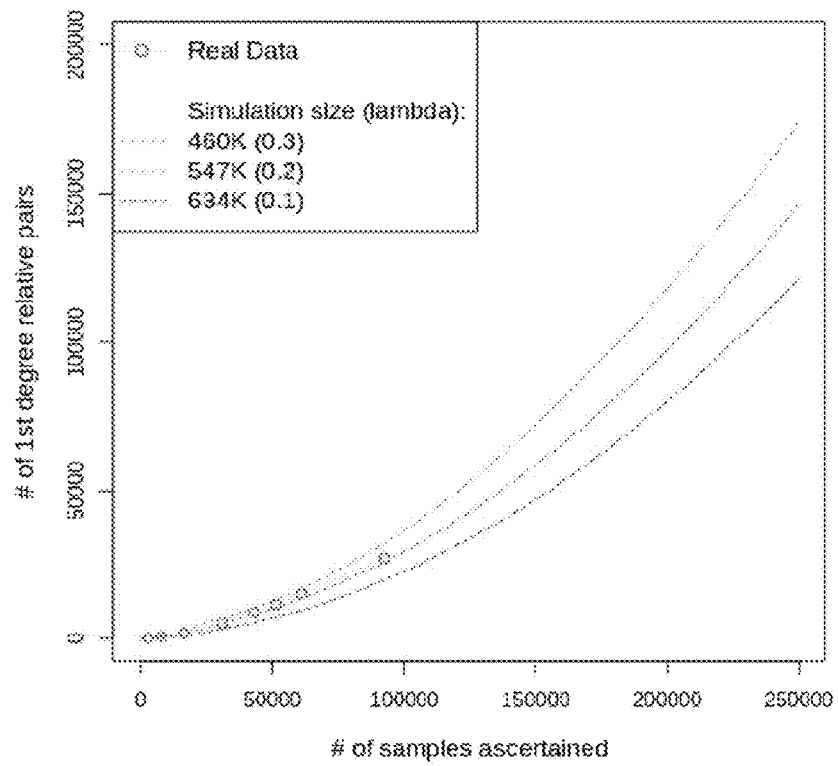

The enrichment of close relatives was modeled by using a clustered ascertainment approach (See Example 17) that produced simulations that better fit the real data for the DiscovEHR (FIG. 15A and FIG. 15B) and the expanded DiscovEHR (FIG. 18A and FIG. 18B). For both FIG. 15 and FIG. 18, the real data was calculated at periodic "freezes" indicated with the punctuation points connected by the faint line. Most simulation parameters were set based on information about the real population demographics and the DiscovEHR ascertainment approach. However, two parameters were unknown and selected based on fit to the real data: 1) the effective population size from which samples were ascertained and 2) the increased chance that someone is ascertained given a first-degree relative previously ascertained, which is referred to as "clustered ascertainment". All panels show the same three simulated population sizes spanning the estimated effective population size. Clustered ascertainment was simulated by randomly ascertaining an individual along with a Poisson-distributed random number of 1st degree relatives (the poison distributions lambda values are indicated in the legends). These simulation results suggested that the effective sampling population size was ~475K individuals and that a Poisson distribution with a lambda of 0.2 most closely matched the enrichment of first-degree relatives. This was consistent with the understanding that the majority of the current participants reside in a certain local geographical area, such as, the Danville, Pa. area (~500K individuals) in this example, rather than evenly distributed across the entire GHS catchment area (>2.5 million individuals).

Figure 18D:
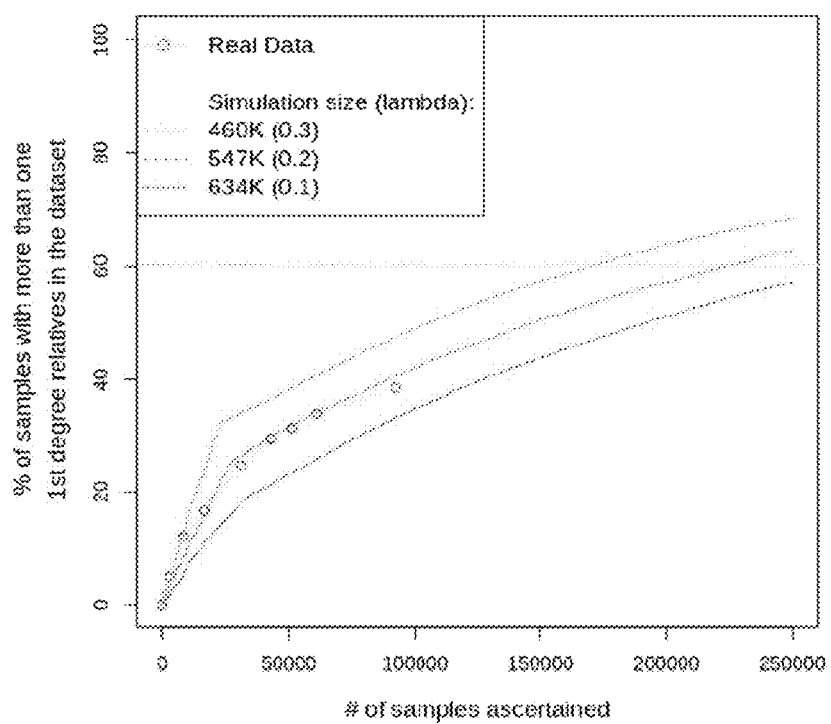
Figure 19A:
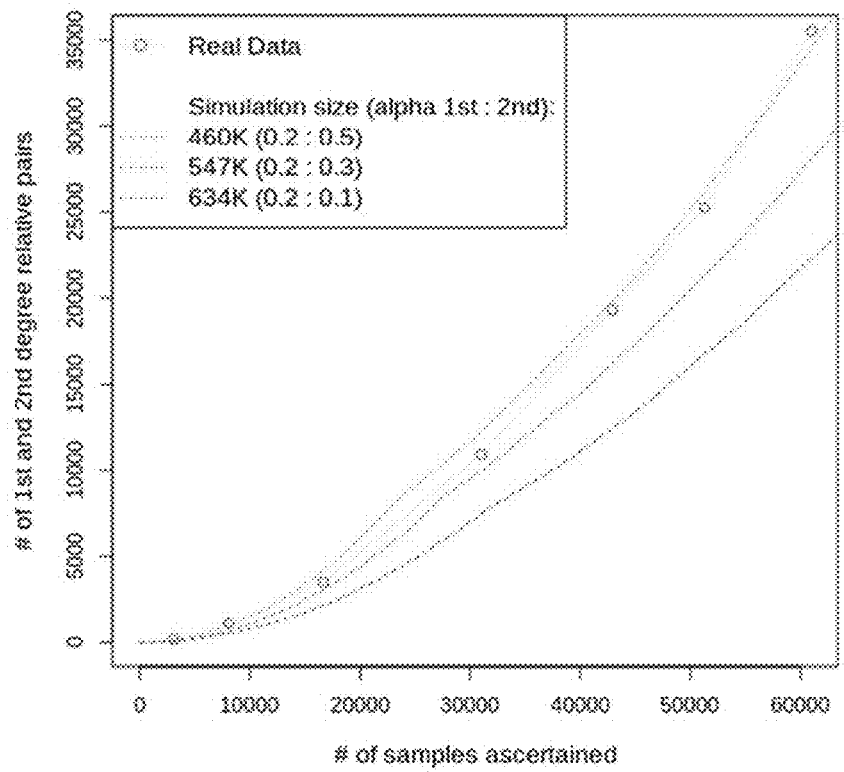
FIGS. 19A, 19B, 19C and 19D show a simulated population and ascertainment fit to the accumulation of first- and second-degree relatedness within the DiscovEHR cohort ascertained according to an exemplary embodiment. Panel A shows accumulation of pairs of first- and second-degree relatives; Panel B shows the proportion of the ascertained participants that have one or more first- and second-degree relatives; Panel C shows simulated ascertainment projections with upper and lower bounds of the number of first- and second-degree relationships; and Panel D shows simulated projection with upper and lower bounds of the proportion of the ascertained participants that have 1 or more first- or second-degree relatives.
Figure 19B:
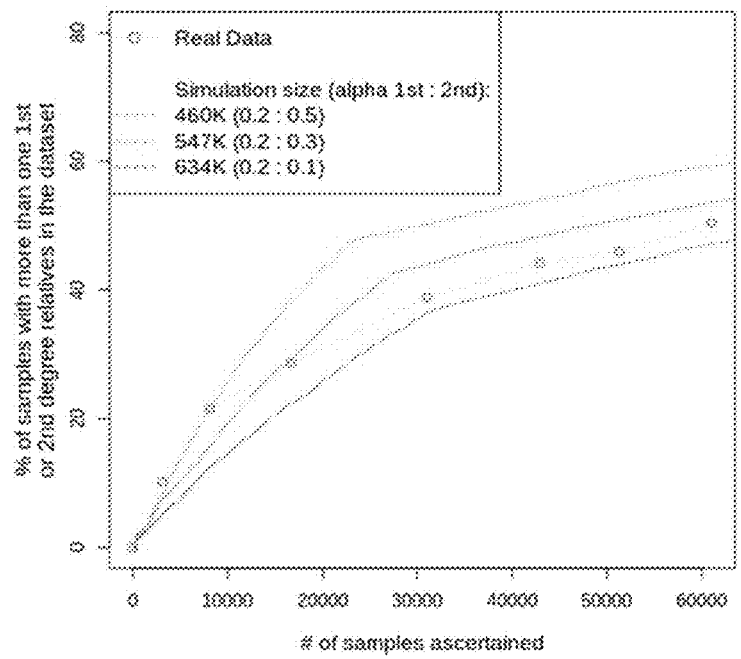
Figure 19C:
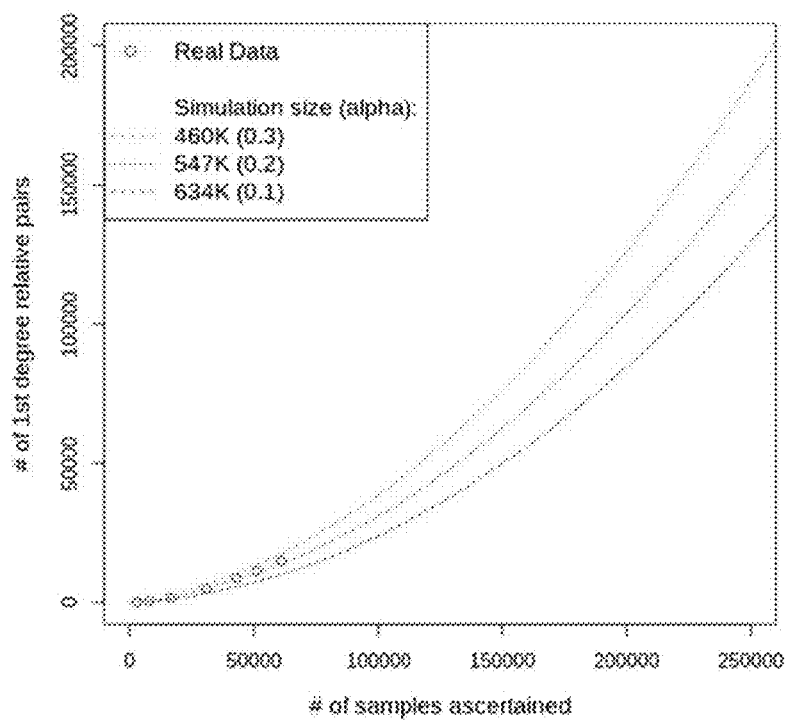
Figure 19D:
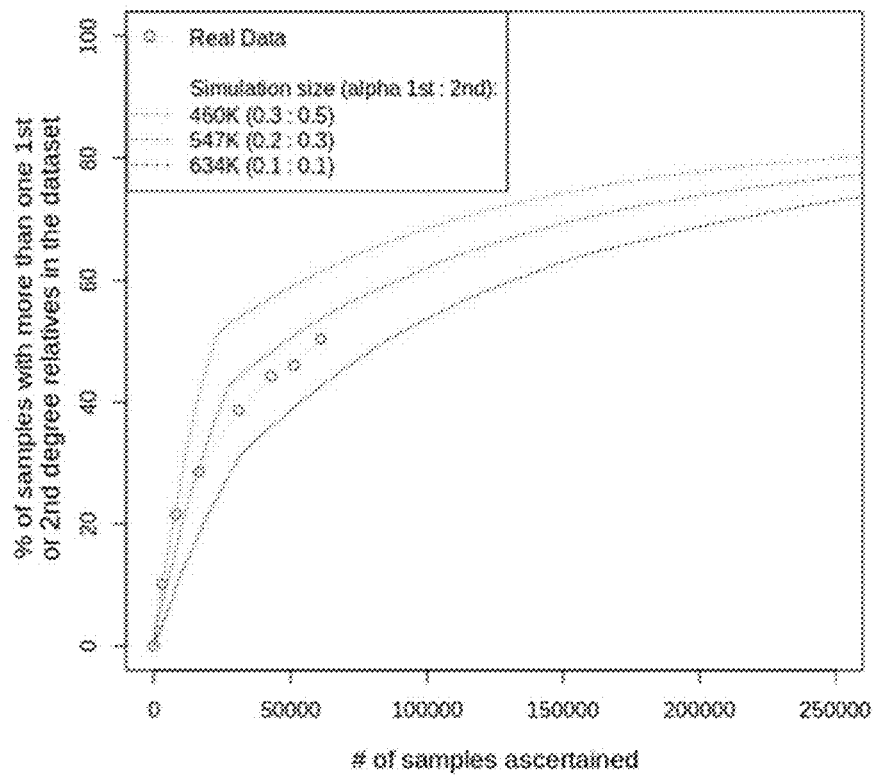
Figure 20A:
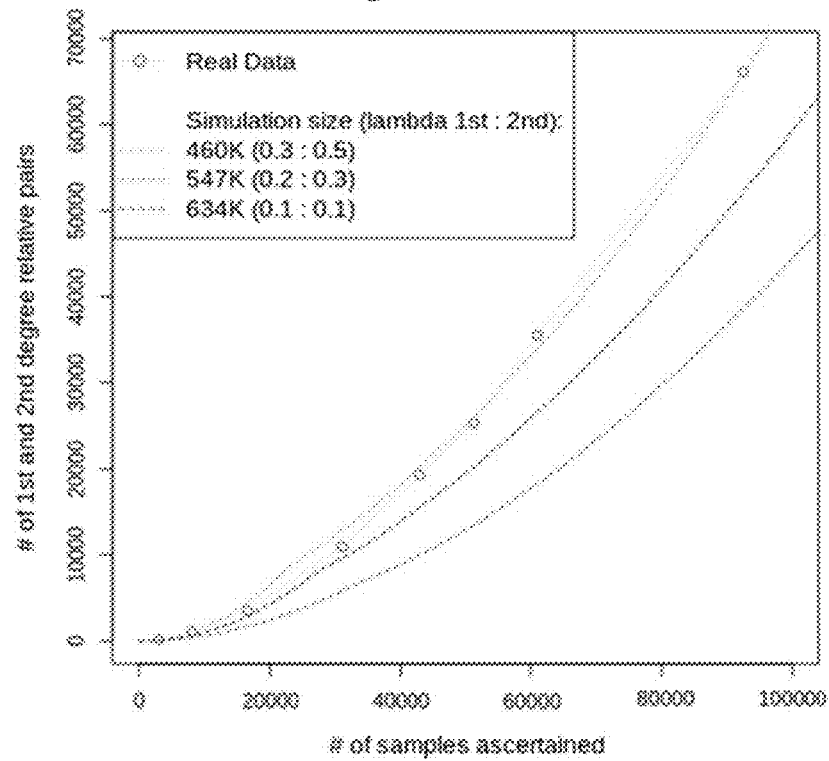
FIGS. 20A, 20B, 20C, and 20D show a simulated population and ascertainment fit to the accumulation of first- and second-degree relatedness within the expanded DiscovEHR cohort ascertained according to an exemplary embodiment. Panel A shows accumulation of pairs of first- and second-degree relatives; Panel B shows the proportion of the ascertained participants that have one or more first- and second-degree relatives; Panel C shows simulated ascertainment projections with upper and lower bounds of the number of first- and second-degree relationships; and Panel D shows simulated projection with upper and lower bounds of the proportion of the ascertained participants that have 1 or more first- or second-degree relatives.
Figure 20B:
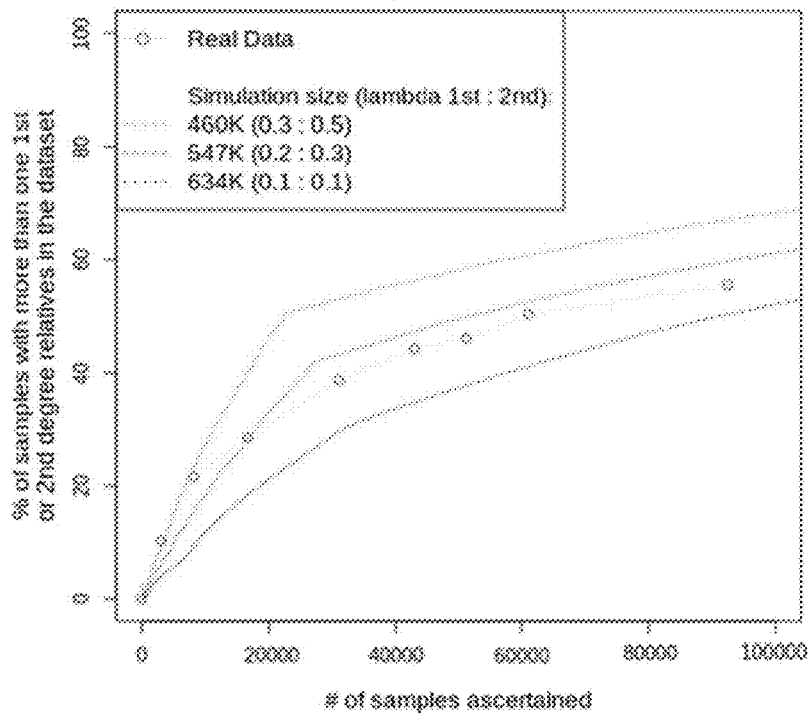
Figure 20C:
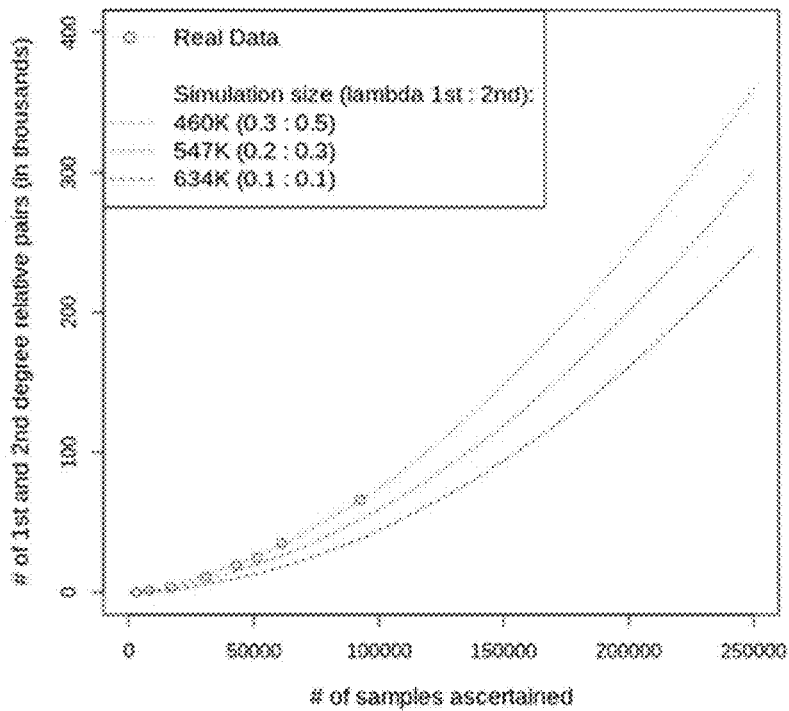
Figure 20D:
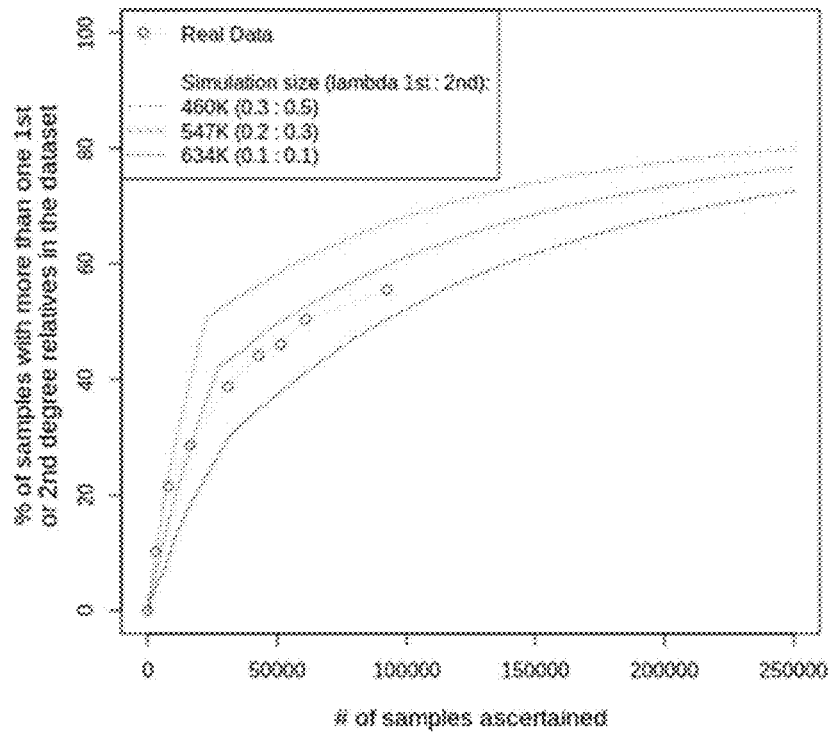

After simulation parameters were identified that reasonably fit the real data, SimProgeny was used to obtain a projection of the amount of first degree relationships that should be expected as the DiscovEHR and the expanded DiscovEHR study expands to the goal of 250K participants. The results indicated that if ascertainment of participants continued in the same way, obtaining ~150K first-degree relationships should be expected for DiscovEHR (FIG. 15C) and expanded DiscovEHR (FIG. 18 C), involving ~60% of DiscovEHR participants (FIG. 15D) and involving ~60% of the expanded DiscovEHR participants (FIG. 18D).

The simulation analysis was then expanded to include second-degree relationships, and the simulation results suggested that with 250K participants well over 200K combined first- and second-degree relationships involving over 70% of the individuals in DiscovEHR (FIG. 19) and expanded DiscovEHR (FIG. 20) should be expected. For this analysis, the real data was calculated at periodic "freezes" indicated with the punctuation points connected by the faint line in the figures. Most simulation parameters were set based on information about the real population demographics and the DiscovEHR ascertainment approach. All panels show the same three simulated population sizes spanning the estimated effective population size. Clustered ascertainment was simulated by randomly ascertaining an individual along with a Poisson distributed random number of 1st degree relatives and a separate random number of 2nd degree relatives (Both Poisson distributions have a lambda indicated in the figure legends.)

The simulation results demonstrated a clear enrichment of relatedness in the DiscovEHR HPG study as well as provided key insights into the tremendous amount of relatedness expected to be seen as ascertainment of additional participants was continued.

Example 3.1

Leveraging the Relatedness Instead of Treating it Like a Nuisance Variable for the DicoverEHR Dataset All 7,684 first-degree family networks were reconstructed in the DiscovEHR dataset using the pedigree reconstruction tool PRIMUS (Staples et al. (2014), Am. J. Hum. Genet. 95, 553-564), and it was found that 98.9% of these pedigrees reconstructed uniquely when considering IBD estimates and reported ages. These pedigrees included 1,081 nuclear families (925 trios, 134 quartets, 19 quintets, and 3 sextets); Table 3 below shows a breakdown of the trios by ancestry. The 1,081 nuclear families were broken out into their individual trio components. For example, a quartet would be split into two separate trios with the same parents. Since the DiscovEHR cohort was mostly European, the vast majority of the trios included individuals of European ancestry. The individuals with UNKNOWN ancestry were generally the children of parents with different ancestral backgrounds, e.g. all three of the EAS-EUR-UNKNOWN trios include a EUR father and EAS mother, resulting in an admixed child. Since there was not reference population that closely matched these EUR-EAS admixed individuals, they fell out as ancestry UNKNOWN.

TABLE 3

| (Breakdown of the trios by ancestral superclass) | |
|---|---|
| | # of trios |
| EUR | 1235 |
| SAS | 1 |
| AFR-EUR | 14 |
| AMR-EUR | 5 |
| EAS-EUR-UNKNOWN | 3 |
| EUR-UNKNOWN | 2 |
| AFR-EUR- | 1 |

TABLE 3-continued (Breakdown of the trios by ancestral superclass)

| | # of trios |
|---|---|
| UNKNOWN | |
| AFR-UNKNOWN | 1 |

Figure 12C:
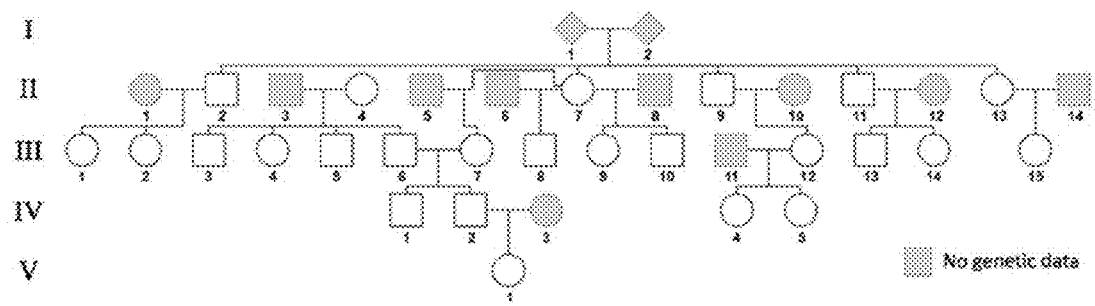
Figure 12D:
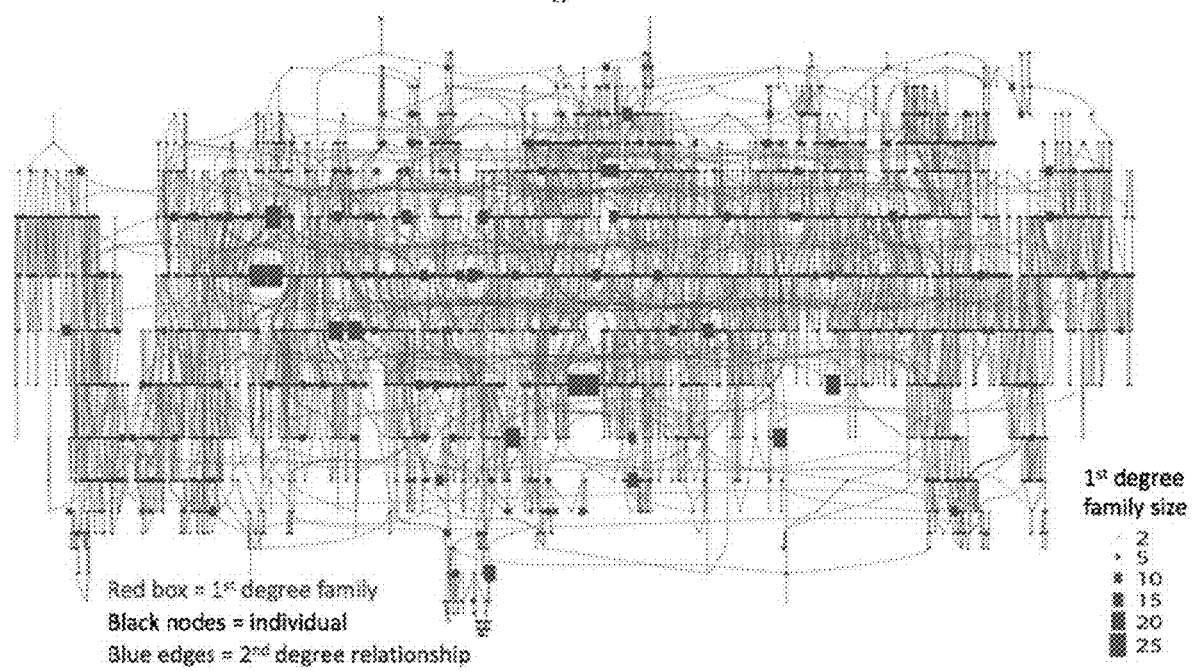

FIG. 12C, shows the largest first-degree pedigrees identified in the DiscovEHR dataset, which contains 25 sequenced individuals. These relationships and pedigrees were used in several ways, including the following.

Compound Heterozygous Mutations

A primary goal of human genetics is to better understand the function of every gene in the human genome. Homozygous loss-of-function mutations (LoFs) are a powerful tool to gain insight into gene function by analyzing the phenotypic effects of these "human knockouts" (KOs). Rare (MAF<1%) homozygous LoFs have been highlighted in recent large-scale sequencing studies and have been critical in identifying many gene-phenotype interactions (Lek et al. (2016), Nature Publishing Group 536, 285-291; Dewey et al. (2016), Science 354, aaf6814-aaf6814; Saleheen et al. (2017), Nature Publishing Group 544, 235-239; and Narasimhan et al. (2016), Science 352, 474-477). While rare compound heterozygous mutations (CHMs) of two heterozygous LoFs are functionally equivalent to rare homozygous KOs, they are rarely interrogated in these large sequencing studies (Lek et al. (2016), Nature Publishing Group 536, 285-291; Dewey et al. (2016), Science 354, aaf6814-aaf6814; and Saleheen et al. (2017), Nature Publishing Group 544, 235-239). Accurate identification of rare CHMs of LoFs is valuable because (1) rare CHMs substantially increase the number of human gene KOs, improving statistical power; (2) rare CHMs KOs may involve extremely rare heterozygous mutations, which may lack homozygous carriers; and (3) rare CHMs provide a more complete set of KOs for a "human KO project" (Saleheen et al. (2017), Nature Publishing Group 544, 235-239; Perdigoto (2017), Nat. Rev. Genet. 18, 328-329).

A survey of rare CHMs in the DiscovEHR dataset was performed. First, 39,459 high-quality potential CHMs (pCHMs) were identified consisting of pairs of rare heterozygous variants that were either putative LoFs (pLoF, i.e., nonsense, frameshift, or splice-site mutations) or missense variants with strong evidence of being deleterious (See Example 10). Second, pCHMs were phased using a combination of allele-frequency-based phasing using EAGLE and pedigree-based phasing using the reconstructed pedigrees and relationship data (FIG. 9). EAGLE phased the pCHMs with 91.4% accuracy based on trio validation (See Table 4 below). However, because there was extensive pedigree and relationships data within this cohort, nearly a third of the pCHMs could be phased based on these data with ~100% accuracy (See Table 4 below), reducing inaccurate phasing by an estimated 31%. The phased pCHMs spanned the entire range from singleton to 1% MAF (See Table 5 below).

TABLE 4

(Phasing accuracy of potential compound heterozygous mutations (pCHMs) with different phasing approaches)

| Phasing approach | Correct | Possible | Accuracy |
|---|---|---|---|
| parent/child | 597 | 597 | 100.00% |
| full-sibling | 33 | 33 | 100.00% |

TABLE 4-continued (Phasing accuracy of potential compound heterozygous mutations (pCHMs) with different phasing approaches)

| Phasing approach | Correct | Possible | Accuracy |
|---|---|---|---|
| distant relative | 120 | 120 | 100.00% |
| EAGLE | 459 | 502 | 91.43% |

All pCHMs with a MAF<1% and a MAC>1 that occurred in a child of a trio were phased using the reconstructed trio and assumed to be "truth". Any pCHMs where one or more of the contributing variants were determined to be de novo in the child were excluded. Then the other phasing methods were evaluated using the trio-phased pCHMs. EAGLE accuracy was evaluated by removing all first-degree relatives of one child from each reconstructed nuclear family and then phasing all variants in the remaining dataset. The EAGLE phased pCHMs were compared to the trio phased pCHMs.

TABLE 5

(Breakdown of the pCHMs found among 61K DiscovEHR participants by minor allele frequency (MAF) and minor allele count (MAC))

| MAF | MAC | # trans | # cis | unknown |
|---|---|---|---|---|
| (0%-0.001%) | 1 | 241 | 135 | 6 |
| (0.001%-0.005%] | 2-6 | 3138 | 3559 | 28 |
| (0.005%-0.01%] | 7-12 | 1830 | 2281 | 14 |
| (0.01%-0.05%] | 13-61 | 3675 | 5679 | 42 |
| (0.05%-0.1%] | 62-122 | 1205 | 2876 | 10 |
| (0.1%-0.5%] | 123-610 | 2742 | 5911 | 31 |
| (0.5%-1%) | 611-1,220 | 504 | 99 | 3 |

Because the accuracy of the pCHMs tended to decrease with extremely rare variants, the MAF for the rarer of the two pCHM variants was used to bin the pCHMs into their respective frequency bins. pCHMs with a MAC of 1 were phased using relationship data and were assumed NOT to be de novo mutations in the pCHM carrier. Unknown phase for pCHMs was a result of one or both pCHM variants being filtered by EAGLE (MAC=1 or missingness >10%) and a lack of relationship data for phasing.

Figure 22:
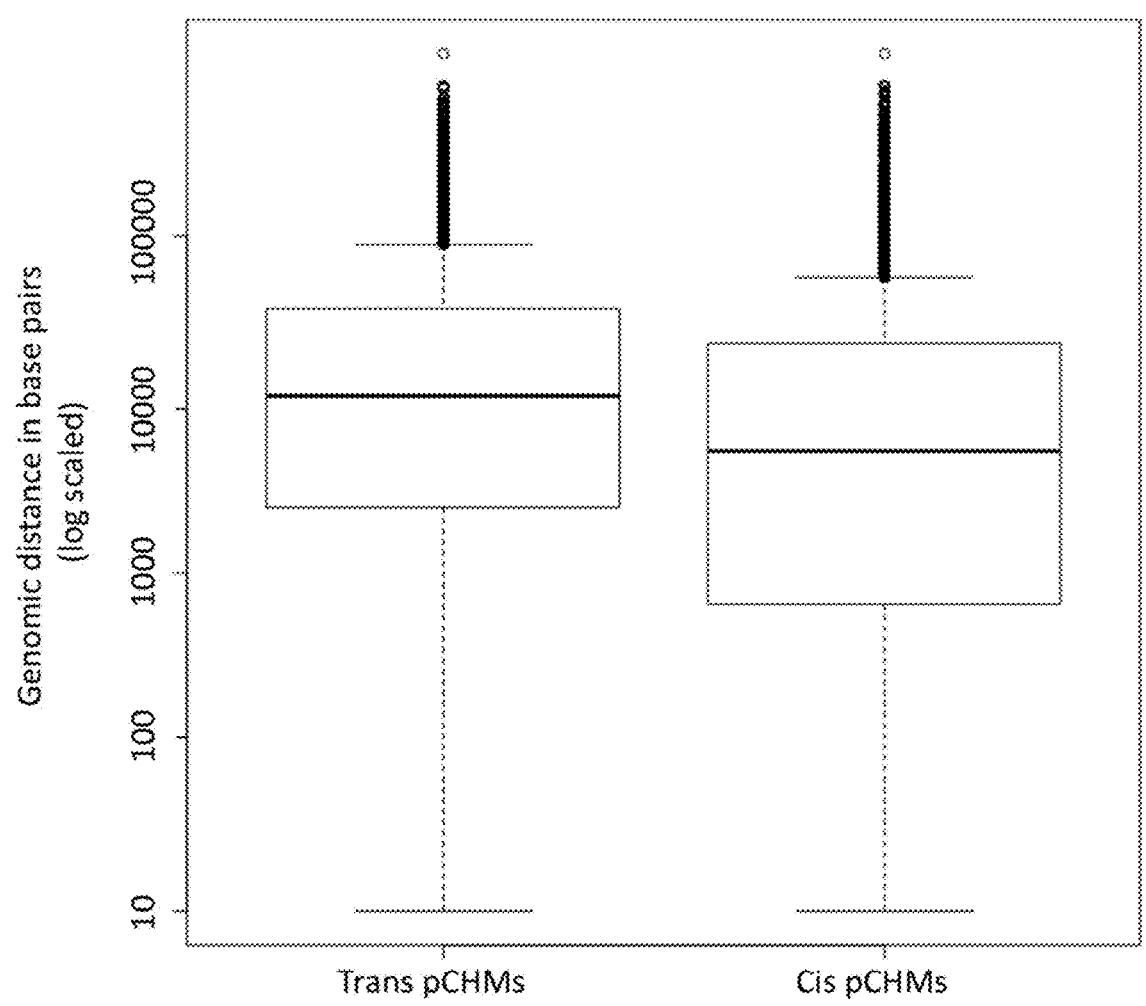
FIG. 22 is a chart illustrating the range of genomic distance between phased compound heterozygous mutant (CHM) variants identified for DiscovEHR dataset according to an exemplary embodiment.

After processing, 39% of the pCHMs were phased in trans, yielding a high-confidence set of 13,335 rare, deleterious CHMs distributed among 11,375 of the 61K individuals (mean=0.22; max=6; FIG. 21, panel A). The median genomic distance between pCHMs variants in cis (5,308 bps) was a little less than half the median distance between variants in trans (11,201 bps; FIG. 22). Nearly a third of the CHMs involved at least one pLoF and 9.8% of CHMs consisted of two pLoF variants (See Table 6 below). Over 3,385 of the 19,467 targeted genes contained one or more CHM carriers (See Table 7 below), and 1,555 (46%) had more than one carrier. The eleven genes with more than 85 CHM carriers were estimated to be among the most LoF tolerant in the genome based on ExAC pLI scores (Lek et al. (2016), Nature Publishing Group 536, 285-291) (See Table 8 below).

TABLE 6

(Breakdown of the functional classes and variant type contributing to the rare CHMs among 61K DiscovEHR participants)

| CHMs class | # CHMs | % CHMs | indel-indel | indel-SNP | SNP-SNP |
|---|---|---|---|---|---|
| pLoF-pLoF | 1302 | 9.8% | 445 | 501 | 356 |
| pLoF-missense | 2945 | 22.1% | 0 | 1212 | 1733 |
| missense-missense | 9088 | 68.2% | 0 | 0 | 9088 |

The table provides the breakdown of the CHMs made of up rare (<1% MAF) pLoF and missense variants. Also shown is how many of these CHMs were made up of indel-indel, indel-SNP, and SNP-SNP pairings.

TABLE 7

(Number of genes with both transcripts affected by rare (<1% MAF) predicted loss-of-function mutations and predicted deleterious mutations in 61K DiscovEHR participants.)

| # of carriers | Homozygotes | CHMs | Homozygotes + CHMs | % increase in KO genes w/CHMs |
|---|---|---|---|---|
| Precited loss-of-function variants only | | | | |
| ≥1 | 1409 | 480 | 1627 | 15% |
| ≥2 | 693 | 163 | 806 | 16% |
| ≥5 | 242 | 49 | 302 | 25% |
| ≥10 | 63 | 14 | 97 | 54% |
| ≥20 | 8 | 6 | 18 | 125% |
| Predicted loss-of-function + deleterious missense variants | | | | |
| ≥1 | 4298 | 3385 | 5519 | 28% |
| ≥2 | 2341 | 1768 | 3370 | 44% |
| ≥5 | 814 | 659 | 1554 | 91% |
| ≥10 | 181 | 254 | 627 | 246% |
| ≥20 | 19 | 92 | 180 | 847% |

TABLE 8

(Genes with the highest number of CHMs are predicted to be loss-of-function tolerant by the ExAC pLI scores.)

| # CHMs | gene | pLI score | pLI score tolerance percentile |
|---|---|---|---|
| 190 | OBSCN | 5.36E-91 | 100.00% |
| 168 | DNAH7 | 1.04E-47 | 99.96% |
| 165 | ADGRV/GPR98 | 8.11E-24 | 99.18% |
| 161 | NEB | 4.08E-17 | 97.79% |
| 123 | DNAH3 | 9.63E-51 | 99.96% |
| 117 | DNAH8 | 2.09E-37 | 99.85% |
| 116 | SYNE1 | 3.75E-27 | 99.45% |
| 111 | SSPO | na* | na* |
| 103 | MTMR2 | 2.13E-01 | 38.32% |
| 96 | FAT1 | 1.77906E-10 | 92.51% |
| 92 | DNAH1 | 4.42227E-20 | 98.68% |

*pLI score for SSPO is not reported by ExAC

For the 11 genes with the most CHMs, shown is their pLI scores as reported by ExAC. Also shown is each gene's percentile for LoF tolerance calculated by ranking all genes by their pLI score and dividing by the total number of genes with report pLi scores.

In order to obtain a more robust set of human knockout genes and demonstrate the added value of CHMs, the CHMs were combined with the 3,915 homozygous pLoFs found among the 61K DiscovEHR participants. pLoF-pLoF CHMs increased the number of genes with >1 and >10 individuals with a putative KO by 15% and 54%, respectively (See Table 6 above). The benefit of included CHMs in a KO analysis was even more significant when missense variants were considered that were predicted to disrupt protein function: CHMs provided 28% more genes with ≥1 carriers and 246% more genes with ≥10 carriers where both copies of the gene were predicted to be completely knocked out or disrupted.

Trio validation results indicated that the familial relationship-based phasing was 100% accurate (750/750 pCHMs), and EAGLE phasing was less accurate at 91.4% (459/502 pCHMs; see Table 3 above). Visual validation of the Illumina read data was also performed for 190 pCHMs (115 cis and 79 trans; 126 EAGLE phased and 74 pedigree/relationship phased). Visual validation showed an overall accuracy of 95.8% and 89.9% for pedigree/relationships and EAGLE phasing, respectively (see Table 9 below). While the Illumina read-based validation results were in line with the trio validation results, it is noted that the Illumina read-based validation accuracy results were lower than the phasing accuracy determined by phasing with trios. It is believed that the difference was likely due to the enrichment for false positive pCHMs in small problematic regions of exons prone to sequencing and variant calling errors.

TABLE 9

(Phasing validation results for 190 pCHMs for which both variants could be phased with Illumina 75 base-pairs reads.)

| | Total | # cis | # trans | cis correct | trans correct | cis accuracy | trans accuracy | overall accuracy |
|---|---|---|---|---|---|---|---|---|
| EAGLE | 119 | 71 | 48 | 65 | 42 | 92% | 88% | 89.9% |
| Pedigree/relationship | 71 | 40 | 31 | 40 | 28 | 100% | 90% | 95.8% |

200 pCHMs from among the 61K DiscovEHR participants where both variants were within 75 base-pairs of each other were randomly selected, and phase was then visually validated by looking at the read stack spanning the two variants. Ten (5%) could not be confidently phased using the read stacks because either there were no reads that overlapped both variants or the reads provided conflicting results (i.e. some reads indicated cis and others indicated trans).

De Novo Mutations

De novo mutations (DNMs) are a class of rare variation that is more likely to produce extreme phenotypes in humans due to a reduction in purifying selection. Recent sequencing studies have shown that DNMs are a major driver in human genetic disease (de Ligt et al. (2012), N. Engl. J. Med. 367, 1921-1929; Deciphering Developmental Disorders Study (2017). Prevalence and architecture of de novo mutations in developmental disorders. Nature Publishing Group 542, 433-438; and Fromer et al. (2014), Publishing Group 506, 179-184), demonstrating that DNMs are a valuable tool to better understand gene function.

Nuclear families reconstructed from the DiscovEHR dataset were used to confidently call 1,800 moderate- and high-confidence exonic DNMs distributed among 887 of the 1,262 available children in trios (See Example 12). The mean number of DNMs per individual was 1.43, with a max of 49 (FIG. 21C). PolyPhen2 predicted 28.2% (N=507) of the DNMs as "probably damaging" and an additional 8.6% (N=154) as "possibly damaging." The DNMs were distributed across 1,597 genes (FIG. 21D), with only one gene receiving more than five. The most common type of DNMs was nonsynonymous SNVs (57.17%) followed by synonymous SNVs (25.56%). Table 10 below provides a complete breakdown of DNM types and shows that proportions of DNMs falling into the different functional classes closely matched those found in a recent study of DNMs in children with development disorders.

TABLE 10

(Breakdown of the type of moderate- and high-confidence exonic DNMs found in the DiscovEHR cohort compared to a recent developmental delay exome study of 4,293 trios.)

| Type of DNM | # of DNMs | % of DNMs | # in DDD study* | % in DDD study* |
|---|---|---|---|---|
| nonsynonymous SNV | 1,029 | 57.2% | 4,797 | 57.8% |
| synonymous SNV | 460 | 25.6% | 1,629 | 19.6% |
| splicing | 74 | 4.1% | 671 | 8.1% |
| non-frameshift deletion | 42 | 2.3% | 167 | 2.0% |
| non-frameshift insertion | 30 | 1.7% | 28 | 0.3% |
| frameshift | 102 | 5.7% | 603 | 7.3% |
| stop-gain SNV | 61 | 3.4% | 402 | 4.8% |
| stop-loss SNV | 2 | 0.1% | 7 | 0.1% |

*The Deciphering Developmental Disorders Study (DDD) (Deciphering Developmental Disorders Study (2017). Prevalence and architecture of *de novo* mutations in developmental disorders. Nature Publishing Group 542, 433-438). The DDD paper also reported 57 DNMs of other classes that were not included in our analysis nor in this table; percentages were adjusted accordingly.

Visual validation of 23 high- and 30 moderate- and 47 low-confidence DNMs spanning all functional classes was attempted to be performed. Eight moderate- and two low-confidence variants could not be confidently called as true or false positive DNMs. Of those remaining, 23/23 (100%) high-confidence, 19/22 (86%) moderate-confidence, and 12/43 (28%) low-confidence DNMs could be validated as true positives. Visual validation also confirmed that the majority (40/49) of potential DNM in individuals with >10 DNMs were likely false positive calls.

Variant and Phenotype Segregation in Pedigrees

Figure 23A:
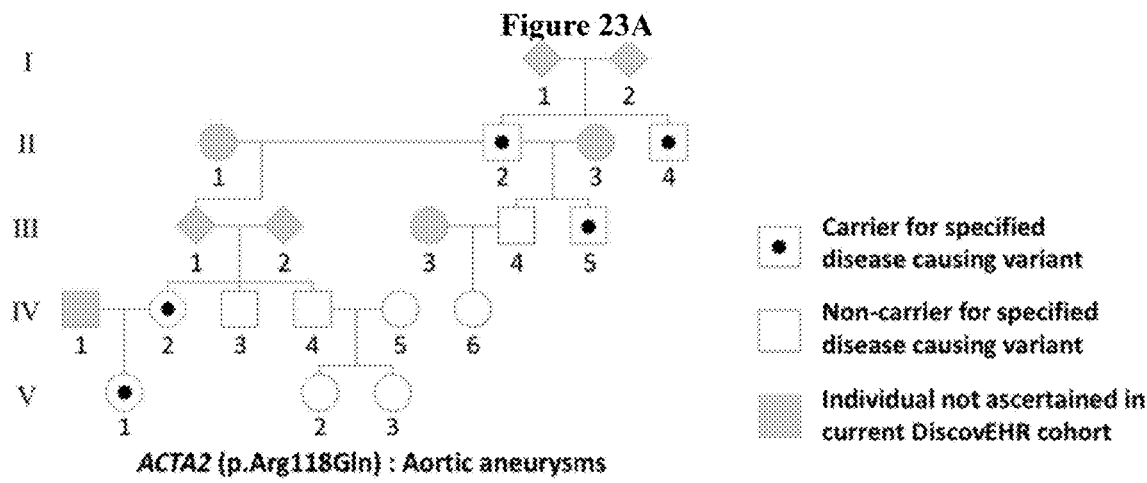
FIGS. 23A, 23B and 23C show reconstructed pedigrees from the DiscovEHR cohort demonstrating the segregation of known disease-causing variants, including variants for (A) aortic aneurysms, (B) long QT syndrome, and (C) thyroid cancer.
Figure 23B:
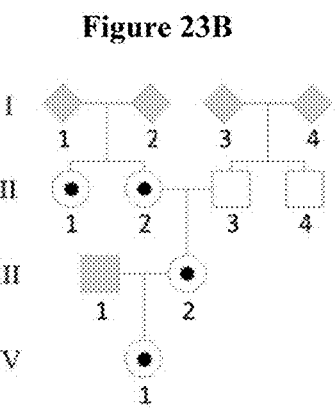
Figure 23C:
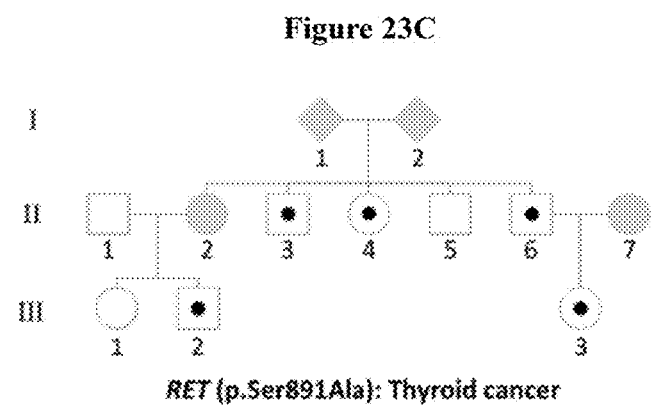
Figure 24:
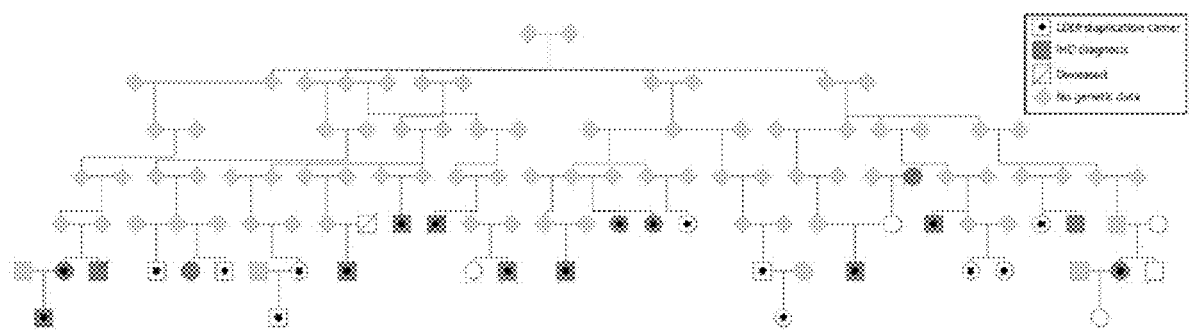
FIG. 24 is a reconstructed pedigree from the sequenced DiscovEHR containing 22/29 carriers of a tandem duplication in LDLR and ten unaffected related (first or second degree) individuals from the sequenced cohort.

The reconstructed pedigree data from among the DiscovEHR dataset were used to distinguish between novel/rare population variation and familial variants and were leveraged to identify highly penetrant disease variants segregating in families that are underappreciated in population-wide association analyses. While this is not intended to be a survey of all known Mendelian disease-causing variation transmitted through these pedigrees, a few illustrative examples were identified including familial aortic aneurysms (FIG. 23, panel A), long QT syndrome (FIG. 23, panel B), thyroid cancer (FIG. 23, panel C), and familial hypercholesterolemia (FH; FIG. 24) (Maxwell, E. K., et al. (2017). Profiling copy number variation and disease associations from 50,726 DiscovEHR Study exomes). The FH example was particularly interesting since 27/29 carriers of a novel familial hypercholesterolemia-causing tandem duplication in LDLR was reconstructed. Five additional carriers (not drawn) were also included in this pedigree. Elevated LDL and total cholesterol as well as increased prevalence of coronary artery disease and early-onset ischemic heart disease ("Age IHD"<55 for males and <65 for females) segregate with duplication carriers. Their shared ancestral history provides evidence that they all inherited this duplication event from a common ancestor approximately six generations back. The remaining two samples were first-degree relatives to each other, but they were not successfully genotyped and as a result could not be connected to the larger pedigree.

Sequencing studies continue to collect and sequence ever increasing proportions of human populations and are uncovering the extremely complex, intertwined nature of human relatedness. In the DiscovEHR dataset, ~35K first- and second-degree relationships were identified, 7,684 pedigrees reconstructed, and a second-degree family network of over 7,000 participants uncovered. Studies in founder populations have already highlighted the complexity of relationships (Old Order Amish (McKusick, V. A., HOSTETLER, J. A., and EGELAND, J. A. (1964). GENETIC STUDIES OF THE AMISH, BACKGROUND AND POTENTIALITIES. Bull Johns Hopkins Hosp 115, 203-222), Hutterites (Ober et al. (2001), The American Journal of Human Genetics 69, 1068-1079), and Ashkenazi Jews (Gusev et al. (2012), Mol. Biol. Evol. 29, 473-486), and recent studies of non-founder populations are reporting extensive levels of relatedness (UK Biobank (Bycroft et al. (2017). Genome-wide genetic data on ~500,000 UK Biobank participant), NHAMES (Malinowski et al. (2015), Front Genet 6, 317), and AncestryDNA (Han et al. (2017), Nat Commun 8, 14238). What once involved only a handful of individuals in large sequencing cohorts, close relationships are likely to involve a large proportion, if not a majority, of individuals in large health-care population-based genomic (HPG) studies. It is demonstrated here through simulations and real data that one can obtain a large number of close familial relationships, nuclear families, and informative pedigrees. This observation was likely to be more prominent in datasets collected for HPG studies since families tend to visit the same healthcare system and have similar genetic and environmental disease risks. It is becoming clear that one can no longer simply remove closely related pairs of individuals from association studies knowing that it is only a small fraction of the overall cohort. The traditional approach of obtaining a maximally sized unrelated set will dramatically reduce HPG cohort sizes, which is unsuitable for many key disease-phenotype analyses performed on these types of cohorts. Instead new methods are needed to leverage the relatedness information as outlined herein.

In this study, several ways have been demonstrated on how to leverage the relatedness information. First, the phasing accuracy of rare compound heterozygous mutations (CHMs) was improved. While accurate phasing of CHMs was obtained with EAGLE, pedigree- and relationship-based phasing was far more accurate, reducing the pCHM phasing error by an estimated 31%. The accuracy of the relationship-based phasing of pCHMs might decrease marginally as variants with >1% MAF are included because phasing using the pairwise relationships assumes that that if two variants appear together in two relatives, then they are in cis and have segregated together from a common ancestor. There is a much higher chance that two independently segregating common variants will appear together in multiple people, resulting in being incorrectly phased as cis by the algorithm. For common variants, phasing using population allele frequencies may be more appropriate than relationship-based phasing.

Second, pedigree reconstruction of the relationships identified with HPG studies provided valuable trios and informative pedigrees that can be used in a number of ways. 1,262 reconstructed trios were used to find 1,800 DNMs, and it was possible to track known disease-causing mutations through extended pedigrees. The number and size of informative pedigrees will continue to increase as a greater portion of the population is sequenced, providing an even richer pedigree dataset. Pedigrees and relationships are particularly useful for extremely rare variants because transmission of a rare variant through pedigrees provides strong evidence that it is real and allows for the use of more traditional Mendelian genetic approaches. Pedigrees particularly turned out to be useful when combined with DiscovEHR's ability to recontact patients and recruit additional family members to augment the small to moderately sized pedigrees in follow-up studies.

Rather than seeing the relatedness as a nuisance that needs to be dealt with, it should be seen as an opportunity to harness a valuable, untapped source of genetic insights. A the era of genomic-based precision medicine commences, a critical need emerges for innovative methods and tools that are capable of effectively mining the familial structure and distant relatedness contained within the ever-growing sequencing cohorts.

Example 3.2

Leveraging the Relatedness Instead of Treating it Like a Nuisance Variable for the Expanded DicoverEHR Dataset Pedigree structures for 12,574 first degree family networks in the expanded DiscovEHR dataset were reconstructed by using the pedigree reconstruction tool PRIMUS. It was found that 98.9% of these pedigrees reconstructed unambiguously to a single pedigree structure when we considered LBD estimates and reported participant ages. These pedigrees include 2,192 nuclear families (1,841 trios, 297 quartets, 50 quintets, 3 sextets, and 1 septet). Table 11 shows a breakdown of the trios by ancestry. FIG. 14, panel C shows the largest first-degree pedigree, which contains 34 sequenced individuals.

TABLE 11

(Breakdown of the trios by ancestral superclass)

| Ancestral estimate | # of trios |
| --- | --- |
| EUR | 2547 |
| AMR | 4 |
| SAS | 2 |
| AFR | 1 |
| AMR-EUR | 18 |
| AFR-EUR | 14 |
| EAS-EUR-UNKNOWN | 6 |
| EUR-UNKNOWN | 5 |
| AFR-UNKNOWN | 2 |
| AFR-EUR-UNKNOWN | 1 |
| AMR-UNKNOWN | 1 |
| EAS-UNKNOWN | 1 |

Figure 25:
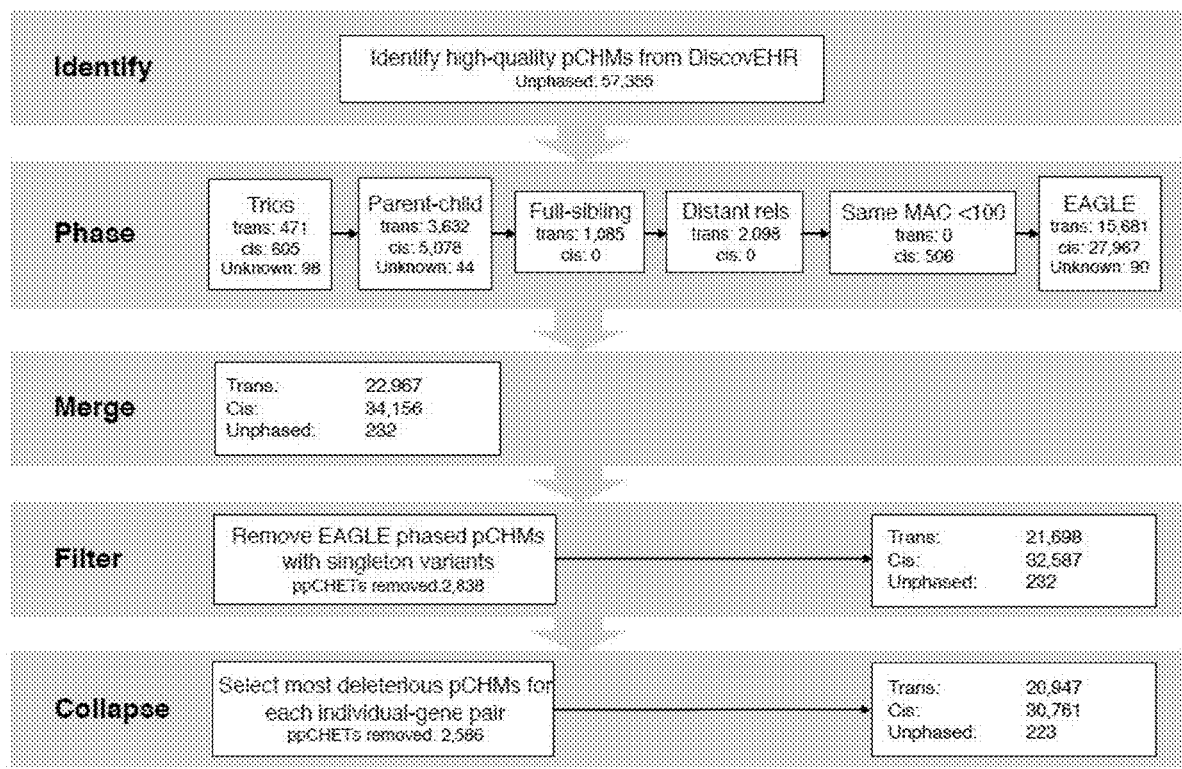
FIG. 25 is decision cascade of an exemplary embodiment for determining the phase of potential Compound Heterozygous Mutations (pCHMs) among the 92K Discover participants.
Figure 26A:
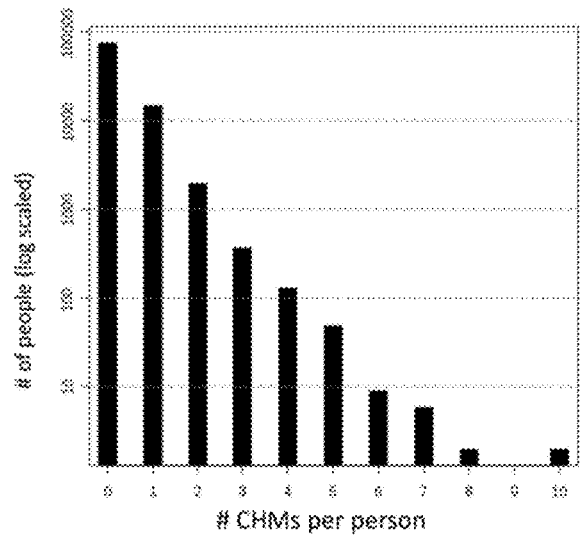
FIGS. 26A, 26B, 26C and 26D show the expanded DiscovEHR cohort that results for compound heterozygous mutations (CHMs) and de novo mutations (DNMs) identified according to an exemplary embodiment. Panel A shows distribution of the number of CHMs per individual in the DiscovEHR cohort; Panel B shows distribution of the number of CHMs per gene; Panel C shows distribution of 3,415 exonic high and moderate confidence DNMs among the children of trios in the DiscovEHR cohort; and Panel D shows distribution non-synonymous DNMs across the 2,802 genes with 1 or more.
Figure 26B:
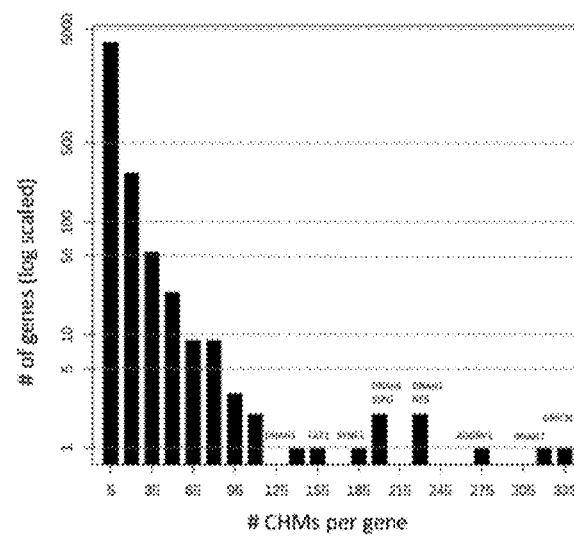
Figure 26C:
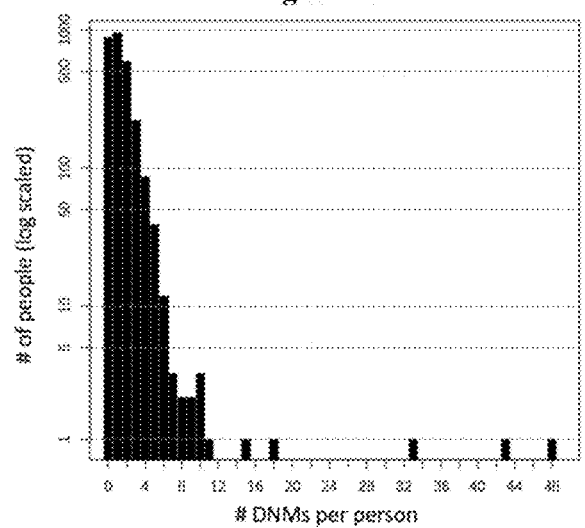
Figure 26D:
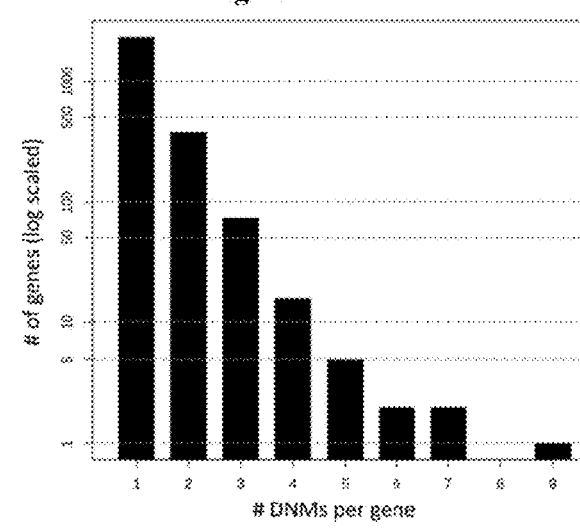

Compound Heterozygous Mutations 57,355 high-quality pCHMs consisting of pairs of rare heterozygous variants were recognized that are either putative LoFs (pLoF; i.e., nonsense, frameshift, or splice-site mutations) or missense variants with strong evidence of being deleterious. Second, phasing of the pCHMs by using a combination of a allele-frequency-based phasing with EAGLE and pedigree-based phasing with the reconstructed pedigrees and relationship data were carried out (FIG. 25). Trio validation indicated that EAGLE phased the pCHMs with an average of 89.1% accuracy (Table 12 below). However, because of the extensive pedigree and relationship data with in this cohort, 25.2% of the pCHMs were phased and 33.8% of the trans CHMs with highly accurate trio and relationship phasing data (R 98.0%; Table 12), reducing inaccurate phasing of trans CHMs by approximately a third. The phased pCHMs spanned the entire frequency range from singletons to 1% MAF (See Table 13 below).

TABLE 12

(Phasing accuracy of potential heterozygous mutations (pCHMs) with different phasing approaches)

| Phasing approach | Correct | Possible | Accuracy |
| --- | --- | --- | --- |
| parent/child | 844 | 844 | 100.0% |
| full-sibling | 48 | 49 | 98.0% |
| distant relative | 168 | 171 | 98.2% |
| realtionships combined | 1060 | 1064 | 99.6% |
| EAGLE | 766 | 860 | 89.1% |

All pCHMs with a MAF<1% and a MAC>1 that occurred in a child of a trio were phased using the reconstructed trio and assumed to be "truth". Any pCHMs where one or more of the contributing variants were determined to be de novo in the child were excluded. Then the other phasing methods were evaluated using the trio-phased pCHMs. EAGLE accuracy was evaluated by removing all first-degree relatives of one child from each reconstructed nuclear family and then phasing all variants in the remaining dataset. The EAGLE phased pCHMs were compared to the trio phased pCHMs.

TABLE 13

(Breakdown of the pCHMs found among 92K expanded DiscovEHR participants by minor allele frequency (MAF) and minor allele content (MAC))

| MAF | MAC | # trans | # cis | unknown |
| --- | --- | --- | --- | --- |
| (0%-0.001%) | 1 | 251 | 143 | 8 |
| (0.001%-0.005%] | 2-9 | 5663 | 6444 | 46 |
| (0.005%-0.01%] | 10-18 | 2669 | 3388 | 31 |
| (0.01%-0.05%] | 19-82 | 5455 | 8149 | 59 |
| (0.05%-0.1%] | 93-184 | 1854 | 3894 | 12 |
| (0.1%-0.5%] | 185-924 | 4302 | 8610 | 63 |
| (0.5%-1%) | 925-1,849 | 753 | 133 | 4 |

Figure 27:
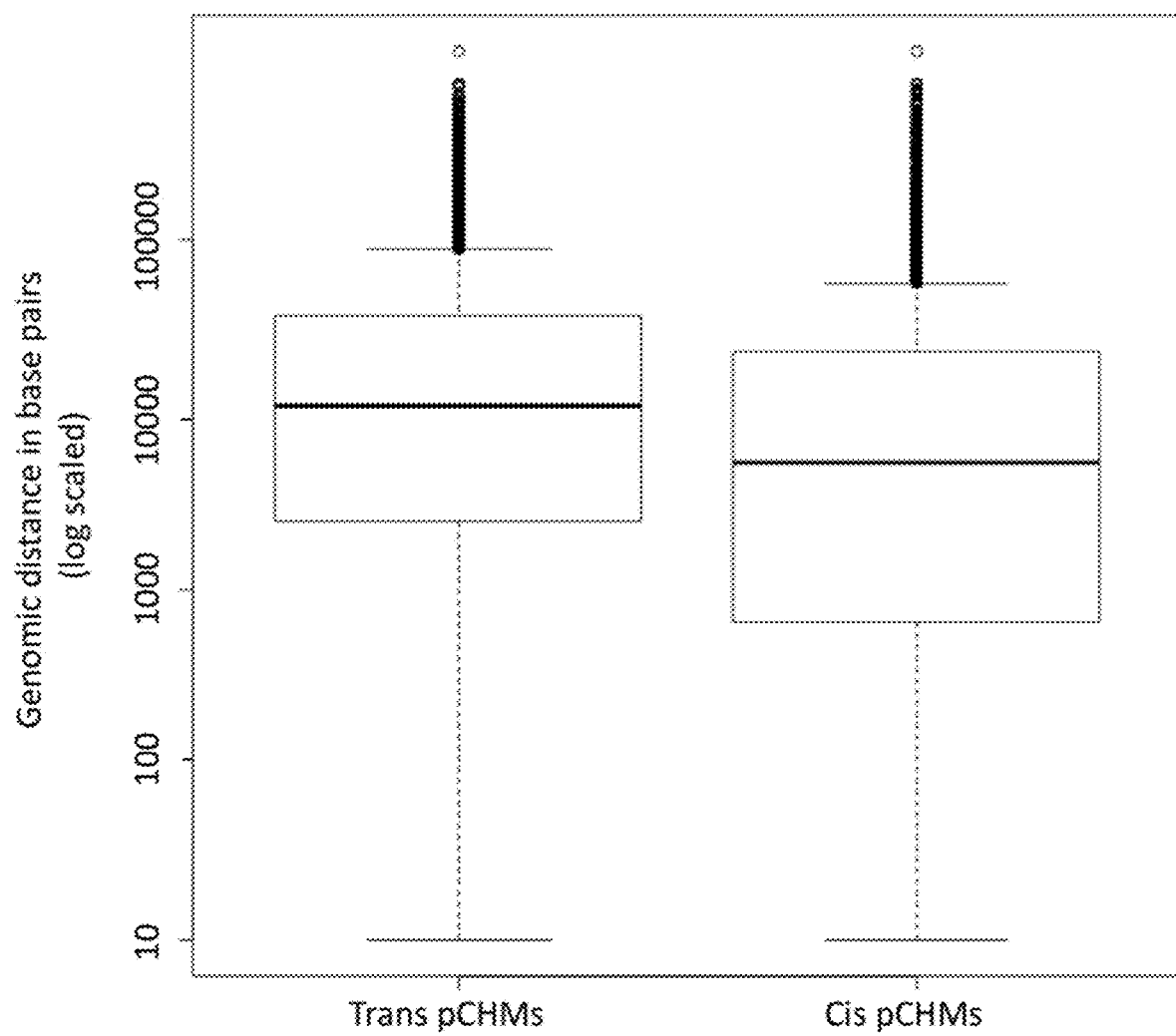
FIG. 27 is a chart illustrating the range of genomic distance between phased compound heterozygous mutant (CHM) variants identified for the expanded DiscovEHR according to an exemplary embodiment.

After processing, 40.3% of the pCHMs were phased in trans, yielding a high-confidence set of 20,947 rare, deleterious CHMs distributed among 17,533 of the 92K individuals (mean 0.23 per person; max ~10 per person; FIG. 26, panel A). The median genomic distance between pCHM variants in cis (5,955 bp) was a little more than half the median distance between the pCHMs in trans (11,600 bp; FIG. 27). Nearly a third of the CHMs involved at least one pLoF, and 8.9% of the CHMs consisted of two pLoF variants (See Table 14 below). More than 4,216 of the 19,467 targeted genes con rain one or more CHM carriers (See Table 15 below), and 2,468 have more than one carrier (FIG. 26, panel B). ExAC pLI scores indicate that the ten genes with more than 125 CHM carriers are likely to be among the most LoF tolerant in the genome. (See Table 16 below).

TABLE 14

(Breakdown of the functional classes and variant type contributing to the rare CHMs among 92K expanded DiscovEHR participants)

| CHMs class | # CHMs | % CHMs | indel-indel | indel-SNP | SNP-SNP |
| --- | --- | --- | --- | --- | --- |
| pLoF-pLoF | 1,864 | 8.9% | 505 | 796 | 563 |
| pLoF-missense | 4,688 | 22.4% | 0 | 1,860 | 2,828 |
| missense-missense | 14,395 | 68.7% | 0 | 0 | 14,395 |

The table provides the breakdown of the CHMs made of up rare (<1% MAF) pLoF and missense variants. Also shown is how many of these CHMs were made up of indel-indel, indel-SNP, and SNP-SNP pairings.

TABLE 15

(Number of genes with both transcripts affected by rare (<1% MAF) predicted loss-of-function mutations and predicted deleterious mutations in 92K expanded DiscovEHR participants.)

| # of carriers | Homozygotes | CHMs | Homozygotes + CHMs | % increase in KO genes w/CHMs |
|---|---|---|---|---|
| Predicted loss-of-function variants only | | | | |
| ≥1 | 1870 | 678 | 2151 | 15% |
| ≥2 | 995 | 257 | 1136 | 14% |
| ≥5 | 426 | 76 | 514 | 21% |
| ≥10 | 155 | 22 | 201 | 30% |
| ≥20 | 33 | 8 | 53 | 61% |
| ≥25 | 9 | 5 | 26 | 189% |
| Predicted loss-of-function + deleterious missense variants | | | | |
| ≥1 | 5306 | 4216 | 6667 | 26% |
| ≥2 | 3169 | 2468 | 4351 | 37% |
| ≥5 | 1415 | 1003 | 2243 | 59% |
| ≥10 | 503 | 503 | 1140 | 127% |
| ≥20 | 79 | 79 | 393 | 397% |
| ≥25 | 32 | 32 | 249 | 678% |

TABLE 16

(Genes with the highest number of CHMs are predicted to be loss-of-function tolerant by the ExAC pLI scores.)

| # CHMs | gene | pLI score | pLI score tolerance percentile |
|---|---|---|---|
| 326 | OBCSN | 5.36E-91 | 100.00% |
| 325 | DNAH7 | 1.04E-47 | 99.96% |
| 267 | ADGRV1/GRP98 | 8.11E-24 | 99.18% |
| 234 | DNAH3 | 9.63E-51 | 99.96% |
| 222 | NEB | 4.08E-17 | 97.79% |
| 204 | DNAH8 | 2.09E-37 | 99.85% |
| 193 | SSPO | na* | na* |
| 185 | SYNE1 | 3.75E-27 | 99.45% |
| 155 | SNAH1 | 4.42E-20 | 98.68% |
| 140 | FAT1 | 1.78E-10 | 92.51% |

*pLI score for SSPO is not reported by ExAC

For the 10 genes with the most CHMs, we show their pLI scores as reported by ExAC3. We also each gene's percentile for LoF tolerance calculated by ranking all genes by their pLI score and dividing by the total number of genes with report pLi scores.

In order to get a more robust set of genes where both copies of the gene are knocked out or disrupted in the same individual and to demonstrate the added value of CHMs, we combined the CHMs with the 6,560 rare (MAF<1%) homozygous pLoFs found among the 92K DiscovEHR participants. pLoF-pLoF CHMs increased the number of genes that were knocked out in R 1 and R 20 individuals by 15% and 61%, respectively (see Table 16 below). The benefit of including CHMs in a KO analysis is even more significant when we consider missense variants that are predicted to disrupt protein function. A combined 20,364 rare homozygous pLOFs and deleterious missense variants were found among the 92K participants. Carriers of homozygous pLoF or predicted deleterious missense variants provided a large number of genes that are predicted to be completely knocked out or disrupted. However, the inclusion of carriers of C HMs provided 26% more genes that are knocked out or disrupted in R 1 individuals and 397% more genes knocked out or disrupted in R 20 individuals (Table 15).

De Novo Mutations

Figure 28:
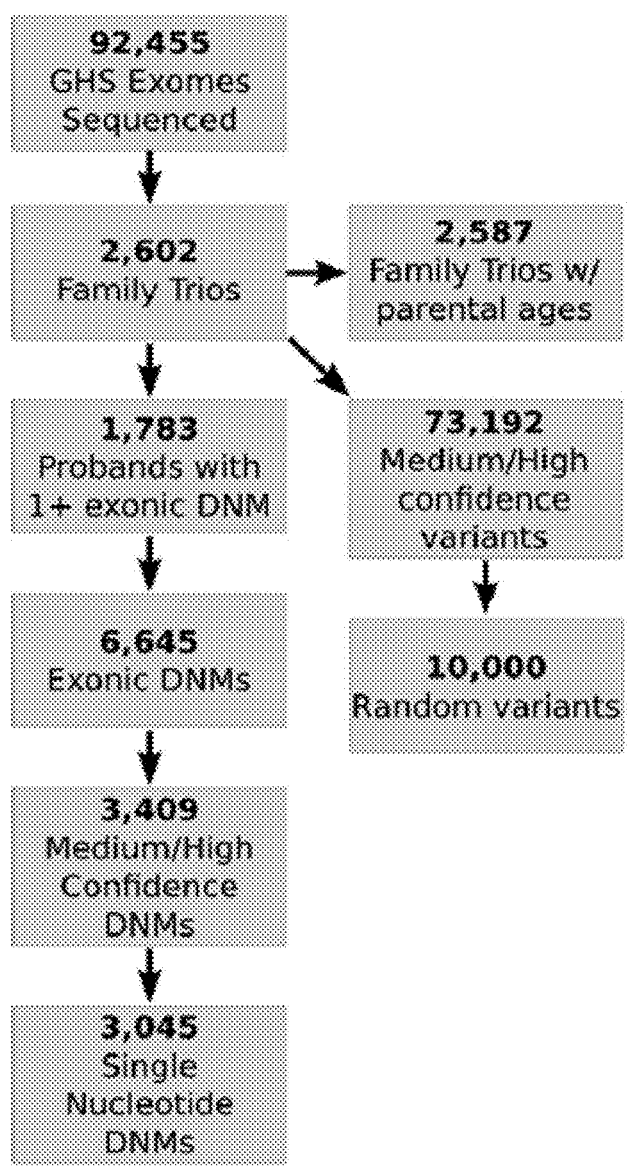
FIG. 28 is a cohort profile showing the number of family trios, family trios with parental ages, probands with 1+exonic DNMs, exonic DNMs, medium/high confidence DNMs, single nucleotide DNMs, medium/high confidence variants and random variants identified in the expanded DiscovEHR dataset according to an exemplary embodiment.
Figure 29A:
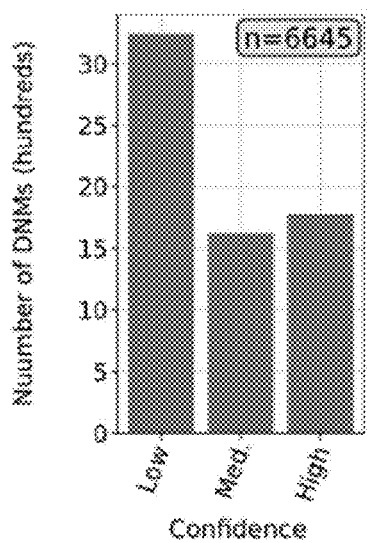
FIG. 29 shows the number of DNMs identified per confidence level and per person in the expanded DiscovEHR cohort according to an exemplary embodiment. Panel A shows the distribution of the number of DNMs per confidence level in the expanded DiscovEHR cohort and Panel B shows the distribution of the number of DNMs per individual in the expanded DiscovEHR cohort wherein the DNMs were identified according to an exemplary embodiment.
Figure 29B:
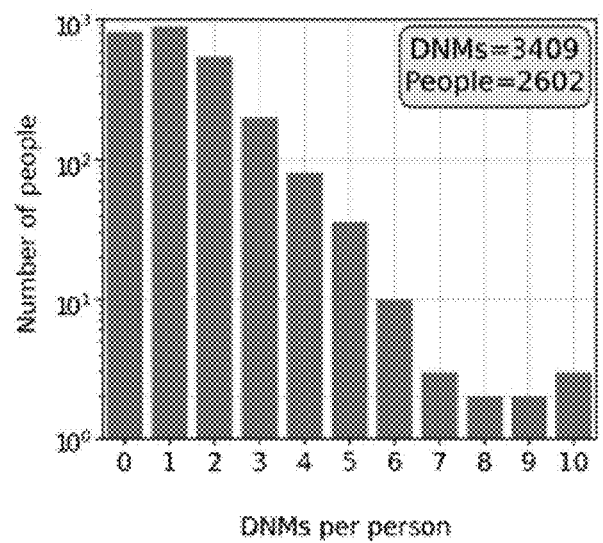

The nuclear families reconstructed from the 92 K expanded DiscovEHR participants could confidently call 3,415 moderate- and high-confidence exonic DNMs distributed among 1,783 of the 2,602 available children in trios (mean~1.31; max~48; FIG. 26, panel C). PolyPhen2 predicts 29.1% (n~995) of the DNMs as "probably damaging" and an additional 9.2% (n~316) as possibly damaging. The DNMs are distributed across 2,802 genes (FIG. 26, panel D), and TTN receives the most (nine). The most common types of DNM are nonsynonymous SNVs (58.5%), followed by synonymous SNVs (24.3%). Table 17 provides a complete breakdown of DNM types and shows that proportions of DNMs falling in to the different functional classes generally match those found in a recent study of DNMs in children with development disorders. As described in FIG. 7, DNM calling, filtering, and confidence ranking workflow were followed. From the cohort with the 92,455 GHS exomes sequenced, 2,602 trios were identified (FIG. 28). 6,645 exonic DNMs were identified from the trios which were sorted on the basis of low, medium, and high confidence DNMs. The families reconstructed from the expanded DiscovEHR dataset were used to confidently call 3,409 moderate- and high-confidence exonic DNMs and 3,045 single nucleotide DNMs from 2,602 family trios (FIG. 29, panels A and B). Most individuals in the cohort had less than 5 DNMs. Further, from the cohort with the 92,455 GHS exomes sequenced, 2,602 trios were identified which were sorted on the basis of low, medium, and high confidence variants to provide 73,192 medium/high confidence variants producing 10,000 random variants.

Figure 30:
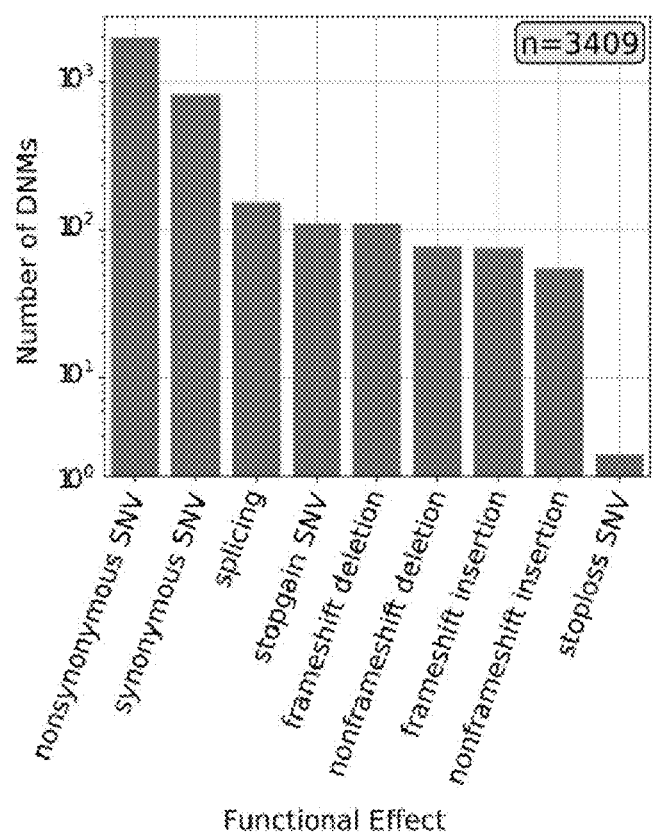
FIG. 30 is a histogram plotting the distribution of the number of DNMs identified per functional effect DNMs in the expanded DiscovEHR cohort according to an exemplary embodiment.

The most common type of DNMs was nonsynonymous SNVs followed by synonymous SNVs. Stop-loss SNV was the least common DNM. This result was similar to the results obtained for the DiscovEHR cohort containing 61K exome sequencing data (See Table 17 below). FIG. 30 provides a complete breakdown of the type of moderate- and high-confidence exonic DNMs (n=3409) found in the expanded DiscovEHR cohort and shows proportions of DNMs falling into the different functional effect classes.

TABLE 17

(Breakdown of the type of moderate- and high-confidence exonic DNMs found in the expanded DiscovEHR cohort compared to a recent developmental delay exome study of 4,293 trios.)

| Type of DNM | # of DNMs | % of DNMs | # in DDD study* | % in DDD study* |
|---|---|---|---|---|
| nonsynonymous SNV | 1,996 | 58.3% | 4,797 | 57.8% |
| synonymous SNV | 831 | 24.3% | 1,629 | 19.6% |
| splicing | 153 | 4.5% | 671 | 8.1% |
| non-frameshift deletion | 78 | 2.3% | 167 | 2.0% |
| non-frameshift insertion | 55 | 1.6% | 28 | 0.3% |
| frameshift | 187 | 5.5% | 603 | 7.3% |
| stop-gain SNV | 112 | 3.3% | 402 | 4.8% |
| stop-loss SNV | 3 | 0.1% | 7 | 0.1% |

*The Deciphering Developmental Disorders Study (DDD) (Deciphering Developmental Disorders Study (2017). Prevalence and architecture of de novo mutations in developmental disorders. Nature Publishing Group 542, 433-438). The DDD paper also reported 57 DNMs of other classes that were not included in our analysis nor in this table; percentages were adjusted accordingly.

Figure 31:
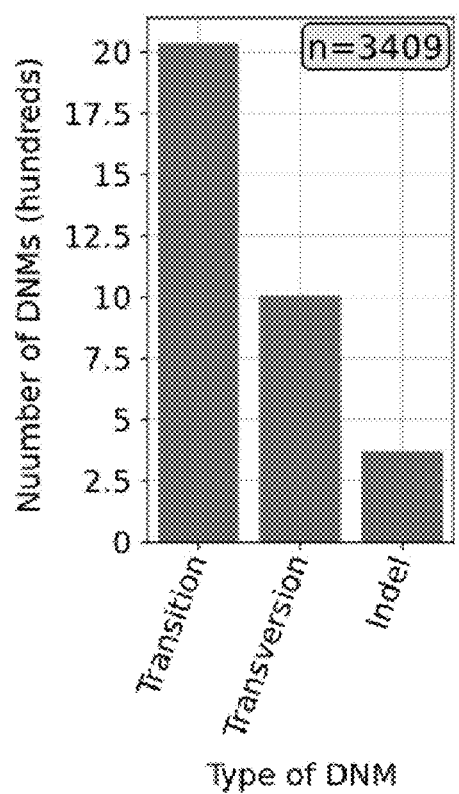
FIG. 31 is a histogram plotting the distribution of the number of DNMs identified per type of DNMs in the expanded DiscovEHR cohort (transition, transversion, and indels according to an exemplary embodiment.
Figure 32:
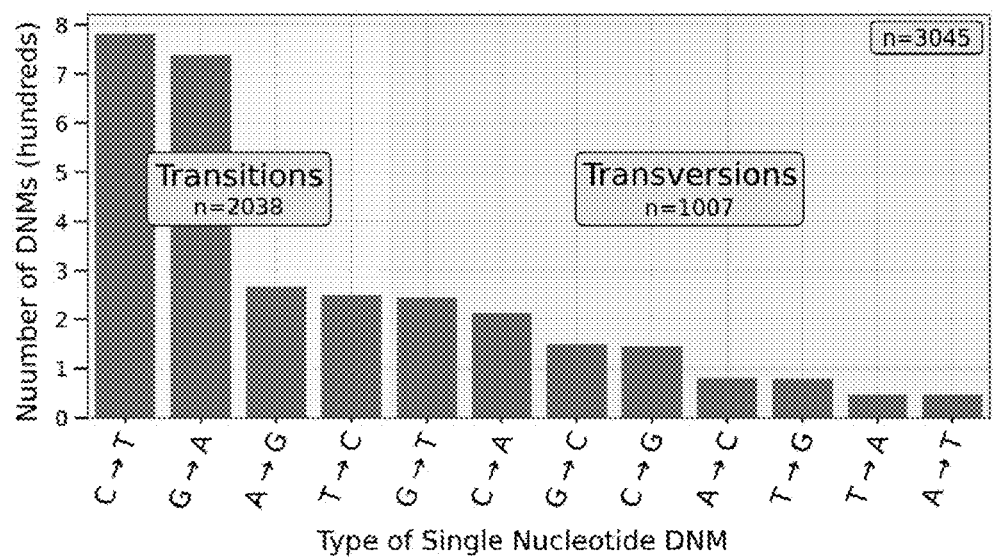
FIG. 32 is a histogram plotting the distribution of the number of DNMs identified per type of single nucleotide DNMs (→) in the expanded DiscovEHR cohort according to an exemplary embodiment.

FIG. 31 provides the breakdown of the type of moderate- and high-confidence exonic DNMs (n=3409) found in the expanded DiscovEHR cohort and shows proportions of DNMs caused by transition, tranversions, and indels. Among the of moderate- and high-confidence exonic DNMs (n=3409) found in the expanded DiscovEHR, the number of mutations due to transitions were 2038, the number of mutations due to transversions were 1007, and the number of mutations due to indels were 364. Thus, the transition to transversion ratio (Ti:Tv) was 2:1, which is similar to the transition to transversion ratio obtained from other studies. Among the single nucleotide DNMs (n=3045), cysteine to thymine and guanine to adenine were the most common mutations (FIG. 32).

Figure 33:
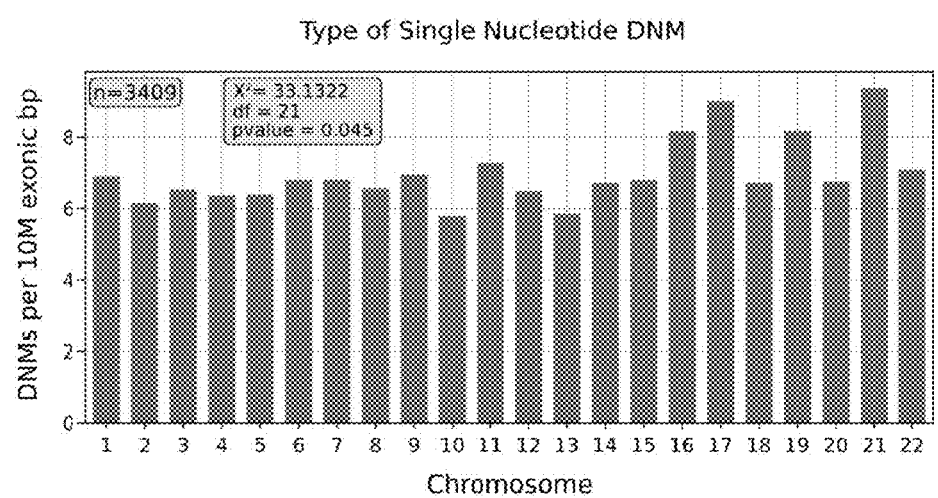
FIG. 33 is a histogram plotting the distribution of the number of DNMs identified per 10M exonic base pairs per chromosome in the expanded DiscovEHR cohort according to an exemplary embodiment.

The medium and high confidence DNMs were evenly distributed across the autosomes. The one-way chi-squared test ($\chi^2$ test) showed DNM per 10M exonic base pair did not significantly deviate from a random distribution (p=0.045) (FIG. 33).

Figure 34:
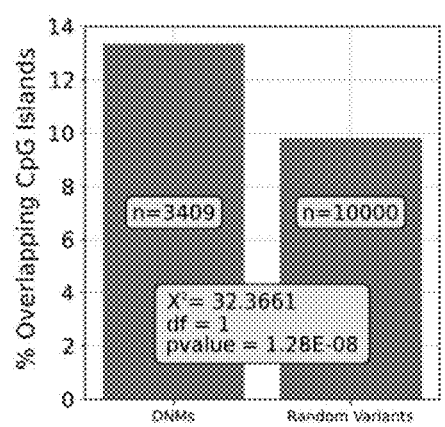
FIG. 34 is a bar chart plotting the distribution of percentage of DNMs or randomly selected variants occurring in regions of the genome know to be enriched for CG dinucleotide (conventionally noted CpG, "p" standing for the phosphate between the two bases) in the expanded DiscovEHR cohort according to an exemplary embodiment.

Mutations in CG dinucleotide (conventionally noted CpG, "p" standing for the phosphate between the two bases) are responsible for one third of disease-causing germ-line mutations in humans (Cooper and Krawczak (1990); Hum. Genet. 85: 55-74). Among the medium/high confidence DNMs (n=3,409), about 13% DNMs were accounted for due to DNMs at the CpG islands. Among the random variants (n=10,000), about 10% DNMs were accounted for due to DNMs at the CpG islands. DNMs were more likely than random variants to occur at CpG islands ($\chi^2$=32.3661, df value=1; p value=1.28E-08) (FIG. 34). This is expected due to the high mutability of these sites.

An attempt to perform visual validation of 23 high-confidence, 30 moderate-confidence, and 47 low confidence DNMs spanning all functional classes was carried out. Eight moderate- and two low-confidence variants could not be confidently called as true- or false-positive DNMs. Of those remaining, 23/23 (100%) high-confidence, 19/22 (86%) moderate-confidence, and 12/43 (28%) low-confidence DNMs were validated as true positives. Visual validation also confirmed that the majority (40/49) of potential DNMs in individuals with >10 DNMs are most likely false-positive calls.

Variant and Phenotype Segregation in Pedigrees

Figure 35:
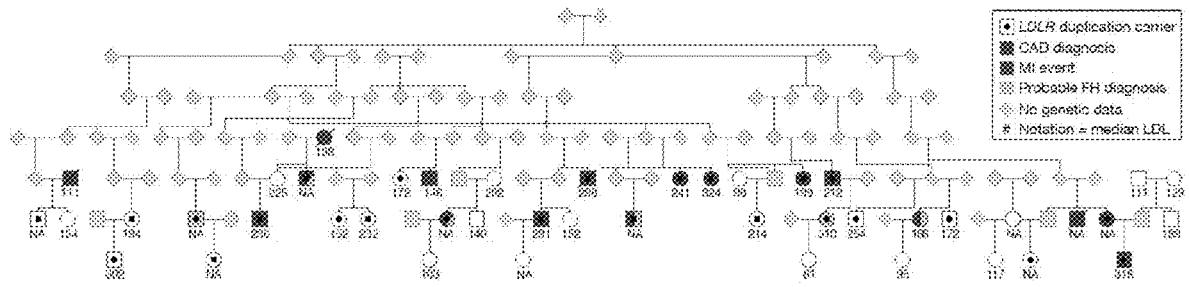
FIG. 35 shows an image of the reconstructed pedigree prediction containing 25/37 carriers of the novel FH-causing tandem duplication in LDLR and 20 non-carrier, related (first- or second-degree) individuals from the expanded DiscovEHR sequenced cohort.

The reconstructed pedigree data from among the 92K expanded DiscovEHR participants was used to distinguish between rare population variation and familial variants and have leveraged it to identify highly penetrant disease variants segregating in families. Although this is not intended to be a survey of all known Mendelian-disease-causing variation transmitted through these pedigrees, similar to the DiscoverEHR dataset, familial aortic aneurysms, long QT syndrome, thyroid cancer, and familial hypercholesterolemia (FH [MLM: 143890]; FIG. 35) have been identified. On updating the CNV calls, 37 carriers of the FH-causing tandem duplication among the 92K exomes have been found. Based on which, 30 out of the 37 carriers into a single extended pedigree were reconstructed. The carriers' shared ancestral history provided evidence that they all inherited this duplication event from a common ancestor approximately six generations back. Although two of the seven remaining carriers are second-degree relatives to each other, genotyping array data was not available to confirm that the remaining seven carriers are also distantly related to the other carriers in FIG. 36. For the pedigree described in FIG. 36, carrier and non-carrier status was determined from the exome data from each individual and it was found that elevated max LDL levels (value under symbols) as well as increased prevalence of coronary artery disease (CAD, red fill) and pure hypercholesterolemia (ICD 272.0; blue) segregated with duplication carriers. Five additional carriers (not drawn) were also found to be distant relatives (seventh- to ninth-degree relatives) of individuals in this pedigree (FIG. 36).

Example 4

Patients and Samples

Two sets of data were collected by applying the prediction model to cohorts—(A) DicovEHR cohort with exomes of 61,720 de-identified patients and (B) expanded DicovEHR cohort with exomes of 92,455 de-identified patients.

All of the de-identified patient-participants in both the cohorts obtained from the Geisinger Health System (GHS) were sequenced. All participates consented to participate in the MyCode® Community Health Initiative (Carey et al. (2016), Genet. Med. 18, 906-913) and contributed DNA samples for genomic analysis in the Regeneron-GHS DiscovEHR Study (Dewey et al. (2016), Science 354, aaf6814-aaf6814). All patients had their exome linked to a corresponding de-identified electronic health record (EHR). A more detailed description of the first 50,726 sequenced individuals has been previously published (Dewey et al. (2016), Science 354, aaf6814-aaf6814; Abul-Husn et al. (2016), Science 354, aaf7000-aaf7000).

The study did not specifically target families to participate in the study, but it enriched for adults with chronic health problems who interact frequently with the healthcare system, as well as participants from the Coronary Catheterization Laboratory and the Bariatric Service Example 5

Sample Preparation, Sequencing, Variant Calling, and Sample QC

Sample prep and sequencing have been previously described in Dewey et. al (Dewey et al. (2016), Science 354, aaf6814-aaf6814).

Upon completion of sequencing, raw data from each Illumina Hiseq 2500 run was gathered in local buffer storage and uploaded to the DNAnexus platform (Reid et al. (2014) 15, 30) for automated analysis. Sample-level read files were generated with CASAVA (Illumina Inc., San Diego, Calif.) and aligned to GRCh38 with BWA-mem (Li and Durbin (2009); Bioinformatics 25, 1754-1760; Li, H. (2013); arXiv q-bio.GN). The resultant BAM files were processed using GATK and Picard to sort, mark duplicates, and perform local realignment of reads around putative indels. Sequenced variants were annotated with snpEFF (Cingolani et al. (2012); Fly (Austin) 6, 80-92) using Ensembl85 gene definitions to determine the functional impact on transcripts and genes. The gene definitions were restricted to 54,214 transcripts that are protein-coding with an annotated start and stop, corresponding to 19,467 genes.

Individuals with low-quality DNA sequence data indicated by high rates of homozygosity, low sequence data coverage, or genetically-identified duplicates that could not be verified to be real monozygotic twins were excluded; 61,019 exomes remained for analysis. Additional information on sample prep, sequencing, variant calling, and variant annotation is reported in Dewey et al. (2016), Science 354, aaf6814-1 to aaf6814-10.

Example 6

Principal Components and Ancestry Estimation

PLINKv1.9 was used to merge the dataset with HapMap3 (International HapMap 3 Consortium, Altshuler et al. (2010); Nature Publishing Group 467, 52-58) and only SNPs were kept that were in both datasets. Also applied the following PLINK filters were applied: --maf 0.1--geno 0.05--snps-only --hwe 0.00001. The principal component (PC) analysis was calculated for the HapMap3 samples and then each sample was projected in the dataset onto those PCs using PLINK. The PCs for the HapMap3 samples were used to train a kernel density estimator (KDE) for each of the five ancestral superclasses: African (AFR), admixed American (AMR), east Asian (EAS), European (EUR), and south Asian (SAS). The KDEs were used to calculate the likelihood that each sample belongs to each of the superclasses. For each sample, the ancestral superclass was assigned based on the likelihoods. If a sample had two ancestral groups with a likelihood >0.3, then AFR was assigned over EUR, AMR over EUR, AMR over EAS, SAS over EUR, AMR over AFR; otherwise "UNKNOWN" (this was done to provide stringent estimates of the EUR and EAS populations and inclusive estimates for the more admixed populations in our dataset). If zero or more than two ancestral groups had a high enough likelihood, then the sample was assigned "UNKNOWN" for ancestry. Samples with unknown ancestry were excluded from the ancestry-based identity-by-decent (IBD) calculations.

Example 7

IBD Estimation

High-quality, common variants were filtered by running PLINK on the complete dataset using the following flags: --maf 0.1--geno 0.05--snps-only --hwe 0.00001. Then a two-pronged approach was taken to obtain accurate IBD estimates from the exome data. First, IBD estimates among individuals were calculated within the same ancestral superclass (e.g. AMR, AFR, EAS, EUR, and SAS) as determined from the ancestry analysis. The following PLINK flags were used to obtain IBD estimates out to second-degree relationships: --genome --min 0.1875. This allowed for more accurate relationship estimates because all samples shared similar ancestral alleles; however, this approach was unable to predict relationships between individuals with different ancestral backgrounds, e.g. a child of a European father and Asian mother.

Second, in order to catch the first-degree relationships between individuals with different ancestries, IBD estimates were calculated among all individuals using the --min 0.3 PLINK option. Individuals were then grouped into first-degree family networks where network nodes were individuals and edges were first-degree relationships. Each first-degree family network was run through the prePRI-MUS pipeline (Staples et al. (2014); Am. J. Hum. Genet. 95, 553-564), which matched the ancestries of the samples to appropriate ancestral minor allele frequencies to improve IBD estimation. This process accurately estimated first- and second-degree relationships among individuals within each family network (minimum PI_HAT of 0.15).

Finally, the IBD estimates from the two previously described approaches were combined by adding in any missing relationships from family network derived IBD estimates to the ancestry-based IBD estimates. This approach resulted in accurate IBD estimates out to second-degree relationships among all samples of similar ancestry and first-degree relationships among all samples.

IBD proportions for third-degree relatives are challenging to accurately estimate from large exome sequencing dataset with diverse ancestral backgrounds because the analysis often results in an excess number of predicted 3rd degree relationships due to artificially inflated IBD estimates. A --min 0.09875 cutoff was used during the ancestry specific IBD analysis to get a sense of how many third-degree relationships might be present in the DiscovEHR and expanded DiscovEHR cohort, but these were not used in any of the phasing or pedigree-based analyses. Rather, for the relationships-based analyses disclosed here, only high-confidence third-degree relationships identified within first- and second-degree family networks were used.

Example 8

Pedigree Reconstruction

All first-degree family networks identified within the DiscovEHR and expanded DiscovEHR cohort were reconstructed with PRIMUSv1.9.0. The combined IBD estimates were provided to PRIMUS along within the genetically derived sex and EHR reported age. A relatedness cutoff of PI_HAT>0.375 was specified to limit the reconstruction to first-degree family networks, and a cutoff of 0.1875 was specified to define second-degree networks.

Example 9

Allele-Frequency-Based Phasing

All bi-allelic variants from the 61,019 exomes were phased using EAGLEv2.3 (Loh et al. (2016); Nat Genet 48, 1443-1448). In order to parallelize the analysis within DNAnexus, the genome was divided into overlapping segments of ~40K variants with a minimum overlap of 500 variants and 250K base-pairs. Since the goal was to phase putative compound heterozygous mutations within genes, care was taken to have the segment break points occur in intergenic regions.

A lift-over of EAGLE's provided genetic_map_hg19.txt.gz file from hg19 to GRCh38 was performed and all variants were removed that switched chromosomes or changed relative order within a chromosome resulting in the chromosome position and cM position to not both be increasing order when sorted. In most cases, this QC step removed inversions around centromeres. SNPs that mapped to an alternate chromosome were also removed. In total, only 2,783 of the 3.3 million SNPs were removed from the genetic map file. The data for each segment was provided to EAGLE as PLINK formatted files and run on DNAnexus with the following EAGLE command line parameters:

--geneticMapFile=genetic_map_hg19_withX.txt.GRCh38_liftover.txt.gz
--maxMissingPerIndiv 1
--genoErrProb 0.01
--numThreads=16

Example 10

Compound Heterozygous Calling

The goal was to obtain high confidence compound heterozygous mutation (CHM) calls of putative loss-of-function (pLoF) variants to identify humans with both copies of genes potentially knocked out or disrupted. Variants were classified as pLoFs if they resulted in a frameshift, stop codon gain, stop codon loss, start codon gain, start codon loss, or splicing acceptor or donor altering variant. A second, expanded set of potentially harmful variants was created that included the pLoFs as well as likely disruptive missense variants, which were defined by being predicted deleterious by all five of the following methods: SIFT (Loh et al. (2016); Nat Genet 48, 1443-1448) (damaging), PolyPhen2 HDIV (damaging and possibly damaging), PolyPhen2 HVAR (damaging and possibly damaging), LRT (deleterious), and MutationTaster (Schwarz et al. (2014); Nat. Methods 11, 361-362) (disease causing automatic and disease causing).

Rare (alternate allele count <1%) potential compound heterozygous mutations (pCHMs) were identified by testing all possible combinations of heterozygous pLoFs and/or deleterious missense variants within a gene of the same person. All variants that were out of Hardy-Weinberg equilibrium (HWE) (p-value<$10^{-15}$ calculated with PLINK (Chang et al. (2015); Gigascience 4, 7)), that exceeded 10% missingness across the 61K samples, or that had another variant within 10 base-pairs in the same individual were excluded. Also excluded were SNPs with QD<3, AB<15%, and read depth <7, and INDELS with QD<5, AB<20%, and read depth <10. After filtering, 39,459 high-quality pCHMs had been obtained that were distributed among 25,031 individuals and that could knockout or disrupt the function of both copies of a person's gene if the pCHM variants were phased in trans.

The next step was to phase the pCHMs. A combination of population allele-frequency-based phasing with EAGLE and pedigree/relationship-based phasing was used to determine if the pCHMs were in cis or trans. FIG. 9 diagrams the pCHM phasing workflow that was employed to obtain the most accurate phasing for each pCHM in the DiscovEHR dataset. FIG. 2 diagrams the pCHM phasing workflow that was employed to obtain the most accurate phasing for each pCHM in the expanded DiscovEHR dataset. Pedigree and relationship phasing proved to be more accurate than EAGLE phasing, so the pedigree and relationship data was preferentially used for phasing. Table 18 below describes the logic employed to determine phase of the pCHMs for the different types of familial relationships. For all remaining pCHMs, the EAGLE phased data described above were used. Any EAGLE phased pCHM where one or both of the variants was a singleton was excluded because EAGLE phasing accuracy with singletons was not significantly different than random guessing (See Table 19 below for DiscovEHR dataset and Table 20 for expanded DiscovEHR dataset). In the DiscovEHR dataset, it was found that if the two variants in the pCHM had the same minor allele count (MAC) less than 100, then they were nearly always in cis (36 out of 37 occurrences among our trios), which exceeded the accuracy of EAGLE pCHM phasing. In the expanded DiscovEHR dataset, it was found that if the two variants in the pCHM had the same minor allele count (MAC) less than 100, then they were nearly always in cis (22 out of 22 occurrences among the trios), which exceeded the accuracy of EAGLE pCHM phasing.

TABLE 18

(Logic used for pedigree-based phasing)

| | Outcome |
|---|---|
| Trio Rules | |
| Only <=1 variant is present among parents | de novo |
| One parent has 0 copies of both variants and the other has 1 or more of both variants | cis |
| Each parent has exactly one copy of one variant in different variants from each other | trans |
| At least one parent has 1 or more copies of both variants and both parents are heterozygous for the same variant | ? |
| Both parents are homozygous for the same variant (not possible because then the child would be homozygous) | NA |
| One parent is homozygous for only one of the two variants, and the other parent has <=1 of that variant and has >=1 of the other variant | trans |
| One parent has 0 copies of variant, and the other parent is homozygous for the other variant | cis |
| One parent is homozygous for both variants | cis |
| Parent-Child Rules (assumes no de novo mutations and that the "NA" trio results don't happen) | |
| PC_rel has 0 variants | cis |
| PC_rel is homozygous for both variants | cis |
| PC_rel is het for both variants and both variants are rare | cis |
| PC_rel is het for both variants and >=1 is NOT rare | ? |
| PC_rel is homozygous for one variant and does not carry the other | trans |
| PC_rel is homozygous for one variant, and het for the other, and the het iss rare | cis |
| PC_rel is homozygous for one variant, and het for the other, and the het is not rare | ? |
| PC_rel is het for one variant and does not have the other, and the het is rare | trans |
| PC_rel is het for one variant and does not have the other, and the het is not rare | ? |
| Full-Sib Rules (assumes no de novo mutations and that the "NA" trio results don't happen) Trio Rules | |
| 1 rare variant in a sib without the other variant | trans |
| If rare variant doesnt appear alone, and the other variants is rare, and $0.5^{\wedge}N < .05$, where N is number of full-siblings | cis |
| >1st Degree Relative Rules | |
| 1 or both rare variants must be in realtive without the other variant | trans |

These rules were applied in order starting from the top rule for each relationship. "?" outcome means the pCHM could not be phased. "NA" outcome indicates that the outcome should not have happened, and was likely a results of sequencing error or other non-Mendelian transmissions of variants. PC_rel refers to the non-pCHM carrier of the parent-child relationship. "rare" refers to a MAF<1%, which includes all the variants used herein.

TABLE 19

(EAGLE phasing accuracy of pCHM by binned minor allele frequency (MAF))

| MAF bin | MAC bin | # of pCHMs | Correct calls/ total possible | Accuracy | incorrect calls (cis: trans) |
|---|---|---|---|---|---|
| (0%-0.001%) | 1 | 2421 (7.1%) | 15/29 | 52% | (8:6) |
| (0.001%-0.005%] | 2-6 | 5485 (16.1%) | 49/64 | 77% | (5:10) |
| (0.005%-0.01%] | 7-12 | 3827 (11.3%) | 66/68 | 97% | (1:1) |
| (0.01%-0.05%] | 13-61 | 9011 (26.5%) | 128/134 | 96% | (2:4) |
| (0.05%-0.1%] | 62-122 | 3976 (11.7%) | 40/41 | 98% | (0:1) |
| (0.1%-0.5] | 123-610 | 8683 (25.5%) | 120/123 | 98% | (1:2) |
| (0.5%-1%] | 611-1,220 | 606 (1.8%) | 12/12 | 100% | (0:0) |

All pCHMs with a MAF<1% were binned by the less frequent of the two variants that made up the pCHM. Correct calls and accuracy was determined by comparing EAGLE phasing of pCHMs to phasing determined with trios. The number of incorrectly EAGLE phased pCHMs that were determined to be cis or trans within the trios are also provided. pCHMs where one or both variants were determined to be de novo in the child of a trio were excluded. While pCHMs with a MAC>6 all had similar accuracy in the mid- to upper-nineties, a drop-off in accuracy was seen with a MAC between 2 and 6. EAGLE's singleton phasing did not perform significantly better that random guessing and therefore EAGLE phased singletons were excluded from the phased pCHM results as well as when measuring the overall accuracy of EAGLE phased pCHMs.

TABLE 20

(EAGLE phasing accuracy of pCHM by binned minor allele frequency (MAF))

| MAF bin | MAC bin | # of pCHMs | Correct calls/ total possible | Accuracy | incorrect calls (cis:trans) |
|---|---|---|---|---|---|
| (0%-0.001%) | 1 | 0/402 (0%)* | 39/69 | 57% | (14:16) |
| (0.001%-0.005%] | 2-9 | 9475/12153 (78%) | 99/129 | 77% | (8:22) |
| (0.005%-0.01%] | 10-18 | 9346/6088 (71.4%) | 105/114 | 92% | (3:6) |
| (0.01%-0.05%] | 19-92 | 9780/13663 (71.6%) | 229/243 | 94% | (8:6) |
| (0.05%-0.1%] | 93-184 | 4461/5760 (77.4%) | 76/78 | 97% | (0:2) |
| (0.1%-0.5] | 185-294 | 10056/12975 (77.5%) | 202/210 | 96% | (3:5) |
| (0.5%-1%] | 925-1849 | 613/890 (68.9 | 16/17 | 94% | (0:1) |

All pCHMs with a MAF<1% were binned by the less frequent of the two variants that make up the pCHM. Correct calls and accuracy was determined by comparing EAGLE phasing of pCHMs to phasing determined with trios. We also provide the number of incorrectly EAGLE phased pCHMs that were determined to be cis or trans within the trios. We excluded pCHMs where one or both variants were determined to be de novo in the child of a trio. While pCHMs with a MAC>9 all have similar accuracy ninety, we see a drop-off in EAGLE pCHM phasing accuracy with a MAC between 2 and 9. EAGLE's phasing of pCHMs containing a singleton does not perform significantly better that random guessing and therefore EAGLE phased singletons have been excluded from the phased pCHM results as well as when measuring the overall accuracy of EAGLE phased pCHMs. *2,838 pCHMs containing singleton variants were removed due to EAGLE's low phasing accuracy of singleton variants. Therefore, the 401 remaining singleton variants were phased with only trios and relationships data.

To obtain a good measure of accuracy for the EAGLE pCHM phasing across the entire dataset, EAGLE was run on the entire dataset excluding all first-degree relatives of one child in each nuclear family before phasing. This pruning was necessary since including parental haplotypes improves the phasing accuracy for the children of trios when compared to samples without parents in the dataset.

Finally, if there were more than one pCHM within the same gene of an individual, then only the pCHM with the most deleterious profile was retained (See Table 21 below). It was possible to phase >99% of all pCHMs, and identify 13,335 rare compound heterozygous mutations (CHMs).

TABLE 21

(Functional effect priority for variants contributing to pCHMs)

| Effect | Description | Functional effect priority |
|---|---|---|
| frameshift | Variant causes a frame shift (e.g., insertion or deletion (INDEL) size that is not a multiple of three) | 1 |
| stop gained | Variant causes a STOP codon (e.g., Cag/Tag, Q/*) | 2 |
| start lost | Variant causes start codon to be mutated into a non-start codon (e.g., aTg/aGg, M/R) | 3 |
| splice acceptor | Variant hits a splice acceptor site (defined as two bases before exon start, except for the first exon) | 4 |
| splice donor | Variant hits a splice donor site (defined as two bases after coding exon end, except for the last exon) | 5 |
| stop loss | Variant causes stop codon to be mutated into a non-stop codon (e.g., Tga/Cga, */R) | 6 |
| missense | Variant causes a codon that produces a different amino acid (e.g., Tgg/Cgg, W/R) | 8 |

TABLE 21-continued (Functional effect priority for variants contributing to pCHMs)

| Effect | Description | Functional effect priority |
|---|---|---|
| affects all transcripts | Both variants affect all transcriptions of the gene | 0 |
| affect some transcripts | Both variants have at least one transcript in common that they affect, but not all transcripts | 10 |
| trans | Variants phased in trans | 0 |
| cis | Variants phases in cis | 30 |

In the case that a person had 2 or more trans pCHMs in the same gene, the values in this table were used to identify and retain the most deleterious pCHM. Effect scores were calculated by adding the functional effect scores of the two variants and then penalizing the pair if they didn't affect all gene transcripts. The pCHM with the lower score was predicted to be the most deleterious and retained.

Example 11.1

Compound Heterozygous Mutation Validation for the DiscovEHR Dataset

Phasing accuracy was evaluated by comparing the phasing predictions to phasing done with trios and with Illumina reads. First, phasing accuracy of the pCHMs was evaluated by using the trio phased pCHMs as truth. Since the phasing approach of each familial relationship was performed independently from the trio phasing, it was possible to get a good measure of phasing accuracy of each of the relationship classes as long as the pCHM carrier was a child in a trio. Table 4 and Table 12 above shows that the accuracy of the familial relationship-based phasing was 100% accurate for these rare pCHMs. EAGLE phasing was less accurate at 91.4% and 89.1% for DiscovEHR and the expanded DiscovEHR dataset, respectively. For the DiscovEHR dataset, the accuracy of EAGLE at phasing pCHMs was evaluated at different minor allele frequency ranges, and found that it consistently attained an accuracy greater than 95% with a MAC greater than 6 and ~77% for a MAC between 2-6 (See Table 19 above). EAGLE phasing only performed poorly with singletons, which was to be expected.

Second, it was attempted to validate 200 pCHMs with short Illumina reads (~75 bp) by looking at the read stacks in Integrative Genomics Viewer (IGV) (Robinson et al. (2011); Nat. Biotechnol. 29, 24-26) to see if the two variants occur on the same read or independently. During this validation process, it was noticed that pCHMs composed of two deletions where the end of the first deletion is within 10 bps of second deletion were actually a single large deletion being incorrectly called as two separate deletions (N=1,109 out of 39,459 pCHMs). Since only 15 were phased as trans (~0.1% of the overall CHM dataset), these pCHMs were not excluded from the overall analysis, but were excluded when the 200 pCHMs were selected for validation. It was possible to use the reads to decisively phase 190 of the 200 randomly selected pCHMs using the short reads. The remaining ten showed read evidence of both cis and trans phasing, most likely due to one or both of the variants being a false positive call.

Example 11.2

Compound Heterozygous Mutation Validation for the Expanded DiscovEHR Dataset

For the DiscovEHR dataset, Table 12 above shows that the accuracy of family-based phasing was 99.6% (1060/1064 pCHMs) for rare pCHMs. EAGLE phasing was less accurate, at 89.1% (766/860 pCHMs; Table 12 above). EAGLE's pCHM-phasing accuracy in different ranges of minor-allele frequency was evaluated to find that EAGLE consistently attains an accuracy greater than 90% with a MAC greater than 9 and an accuracy around 77% for a MAC between 2 and 9 (See Table 20 above). EAGLE phasing performed poorly with singletons.

Second, it was attempted to validate 200 pCHMs with short (975 bp) Illumina reads by looking at the read stacks in the Integrative Genomics Viewer (IGV) (Robinson et al. (2011); Nat. Biotechnol. 29, 24-26) to see if the two variants occur on the same read or independently. 190 (115 cis and 79 trans; 126 EAGLE-phased and 74 pedigree- or relationship phased) selected pCHMs by using short reads. The remaining ten showed read evidence of both cis and trans phasing, most likely because one or both of the variants were false positive calls. Visual validation showed an overall accuracy of 95.8% and 89.9% for pedigree and relationship phasing and EAGLE phasing, respectively (See Table 22). Although the Illumina read-based validation results are in line with the trio validation results, the Illumina read-based validation accuracy results were lower than the accuracy of phasing with trios. The difference is most likely due to the enrichment for false-positive pCHMs in small problematic exon regions prone to sequencing and valiant calling errors.

TABLE 22

Phasing validation results for 190 pCHMs for which both variants could be phased with Illumina 75 base-pairs reads.

| | Total | # cis | # trans | cis correct | trans correct | cis accuracy | trans accuracy | overall accuracy |
|---|---|---|---|---|---|---|---|---|
| EAGLE | 119 | 71 | 48 | 65 | 42 | 92% | 88% | 89.9% |
| Pedigree/relationship | 71 | 40 | 31 | 40 | 28 | 100% | 90% | 95.8% |

200 pCHMs were randomly from among the 92K expanded DiscovEHR participants where both variants were within 75 base-pairs of each other, and visually validated phase by looking at the read stack spanning the two variants. Ten (5%) could not be confidently phased using the read stacks because either there were no reads that overlapped both variants or the reads provided conflicting results (i.e. some reads indicated cis and others indicated trans).

Example 12

De Novo Mutation (DNM) Detection

The results from two different approaches for detecting DNMs were merged. The first method was TrioDeNovo (Wei et al. (2015); Bioinformatics 31, 1375-1381), which reads in the child's and parents' genotype likelihoods at each of the child's variable sites. These likelihoods were input into a Bayesian framework to calculate a posterior likelihood that a child's variant was a DNM. The second program was DeNovoCheck (https://sourceforge.net/projects/denovocheck), which is described in the supplementary methods of de Ligt, et al. (de Ligt et al. (2012); N. Engl. J. Med. 367, 1921-1929). DeNovoCheck takes in a set of candidate DNMs identified as being called in the child and not in either parent. It then verifies the presence of the variant in the child and absence in both of the parents by examining the BAM files. These potential DNMs were filtered and a confidence level for each DNM in the union set is evaluated using a variety of QC metrics. FIG. 7 illustrates this DNM calling process, shows the variant filters we applied, and provides the criteria we used to classify each DNM as either low-confidence, moderate-confidence, or high-confidence.

Example 13.1

Figure 36A:
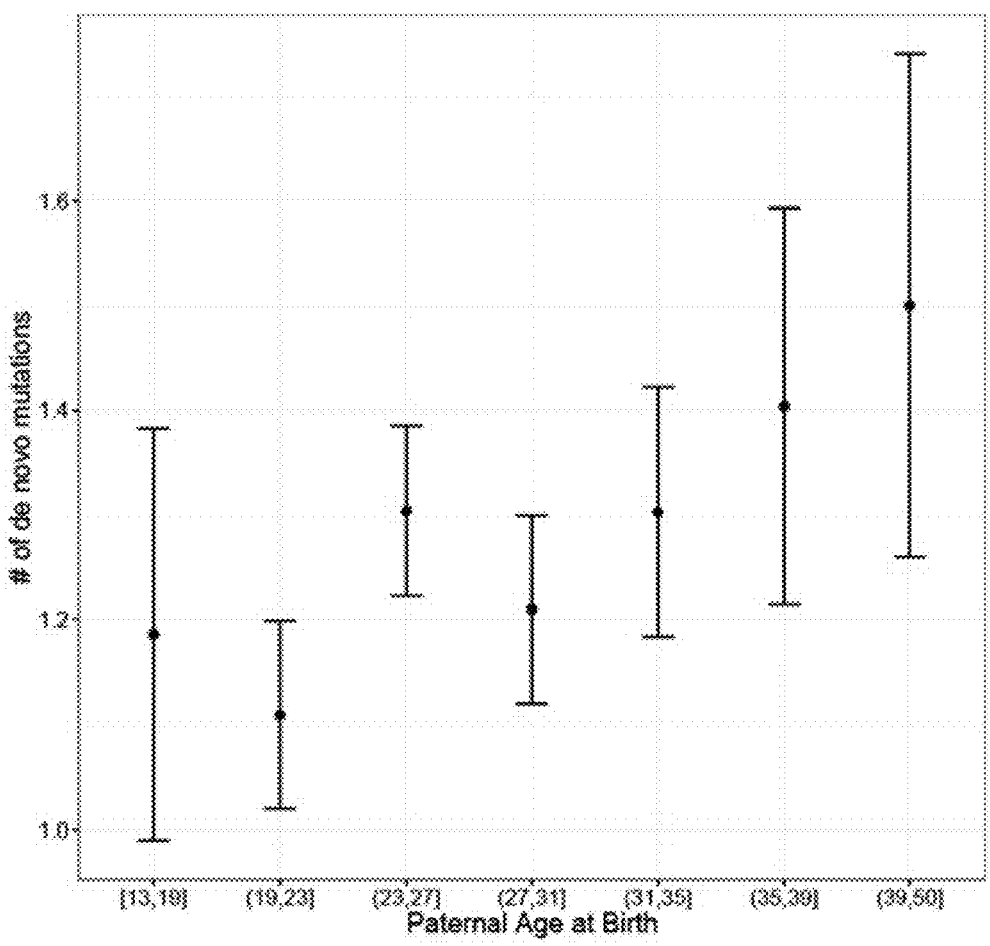

Testing for a Correlation Between Parent Age at Conception and # of DNMs in the Child in the DiscovEHR Dataset For this analysis, samples having more than 10 DNMs were excluded as outliers (N=6 excluded samples), likely indicating technical artifacts or somatic variation. Maternal and paternal age are highly correlated (rho=0.78, p=1.2× $10^\wedge$-262); when modelled jointly, neither were significant due to collinearity (0.0053 maternal DNMs/year, p=0.48; 0.0076 paternal DNMs/year, p=0.26; Poisson regression) (FIGS. 36A and 36B). Then parental age difference (paternal-maternal age) was tested alongside either maternal or paternal age at birth. Both paternal and maternal age turned out to be equally predictive of number of DNMs (i.e., age difference was not significantly associated with number of DNMs given maternal or paternal age).

Figure 37:
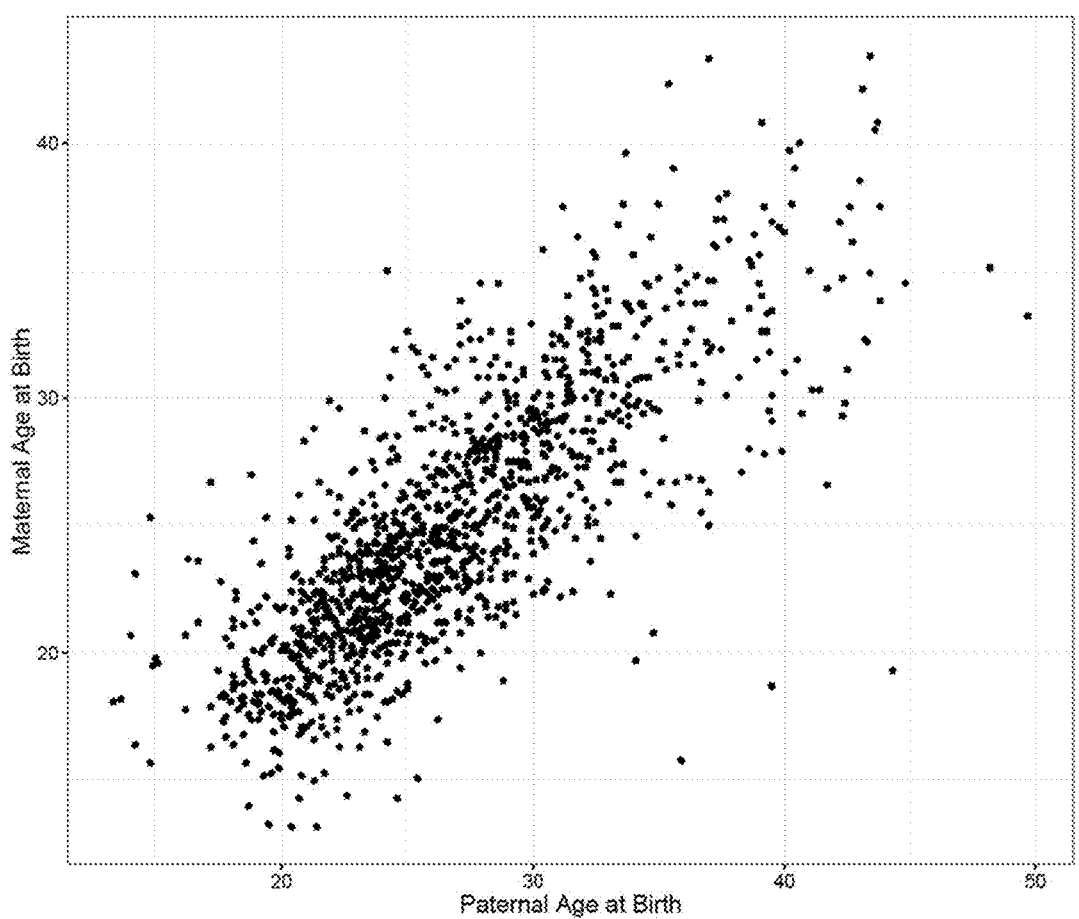
FIG. 37 is a chart showing a correlation of maternal and paternal age at birth of the child in the DiscovEHR cohort with DNMs identified in the child according to an exemplary embodiment.
Figure 38:
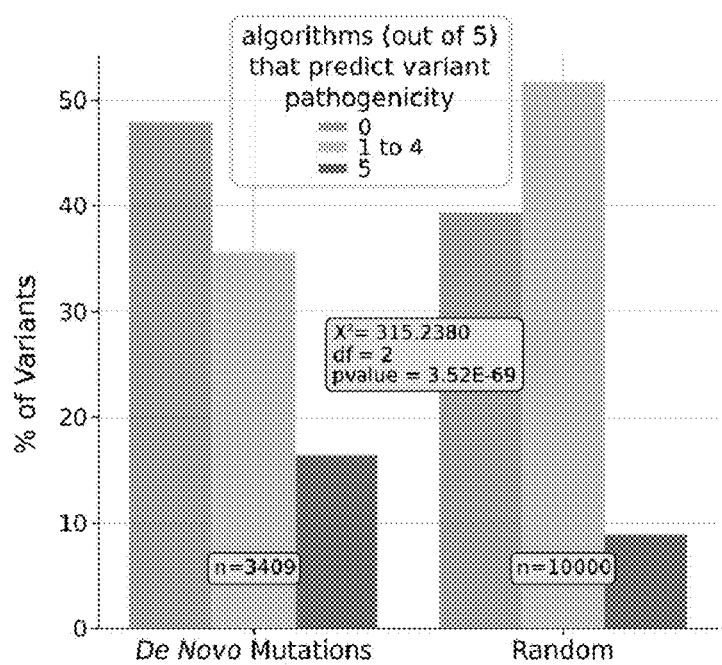
FIG. 38 is a histogram plotting the pathogenicity predictions for DNMs and random variants identified in the expanded DiscovEHR cohort according to an exemplary embodiment.

An increase in the number of exonic DNMs was also observed with respect to both maternal (0.012 DNMs/year, p=0.011; Poisson regression; FIG. 37) and paternal age at birth (0.011 DNMs/year; p=0.007), consistent with other reports (Deciphering Developmental Disorders Study (2017). Nature 542, 433-438; Kong et al. (2012) Nature 542, 433-438; Rahbari et al. (2016) Nat. Genet. 48, 126-133; and Wong et al. (2016) Nat. Commun. 7, 10486). Notably, maternal and paternal age at birth were highly correlated in the dataset (rho=0.78, p=1.2×$10^\wedge$-262; FIG. 38), thus the rates were not additive, and no significant difference was identified to distinguish either as the driving factor.

Example 13.2

Testing for a Correlation Between Parent Age at Conception and # of DNMs in the Child in the Expanded DiscovEHR Dataset The expanded DiscoverEHR cohort showed results similar to DiscovEHR cohort on testing for correlation between parents age at conception and number of DNMs in the child. An increase in the number of exonic DNMs with respect to both maternal (0.011 DNMs/year, p=7 $0.3×10^{-4}$; Poisson regression; FIG. 37) and paternal (0.010 DNMs/year; p=5.6×$10^{-4}$) age at birth was observed, consistent with other reports. Notably, maternal and paternal age at birth are highly correlated in the dataset (r=0.79; FIG. 39); thus, the rates are not additive, and no significant difference identified either as a driving factor.

Paternal age correlated with the number of DNMs per person, using a Poisson distribution (n=2587, coefficient=0.010, p=5.67E-4). Similarly, maternal age correlated with the number of DNMs per person, using a Poisson distribution (n=2587, coefficient=0.011, p=7.35E-4). Further, paternal and maternal age are also correlated with each other ($R^2$=0.79; p<10E-308).

Using functional prediction algorithms—SIFT (damaging), PolyPhen2 HDIV (damaging and possibly damaging), PolyPhen2 HVAR (damaging and possibly damaging), LRT (deleterious), and MutationTaster (Schwarz et al. (2014); Nat. Methods 11, 361-362) (disease causing automatic and disease causing), pathogenicity of the DNMs was predicted. Pathogenicity predictions of DNMs are significantly different than that of random variant distribution (FIG. 38). A higher percentage of DNMs also had unanimous predictions of non-pathogenicity. DNMs are 1.8 times more likely to be predicted as pathogenic by 5/5 algorithms. Random variants are 1.5 times more likely to have discordant predictions of pathogenicity.

Example 14

LDLR Tandem Duplication Distant Pedigree Estimation

Although it is not possible to know the true family history of the de-identified individuals in our cohort, PRIMUS (Staples et al. (2014); Am. J. Hum. Genet. 95, 553-564) reconstructed pedigrees, ERSA (Huff et al. (2011); Genome Res. 21, 768-774) distant relationship estimate, and PADRE's (Staples et al. (2016); The American Journal of Human Genetics 99, 154-162) ability to connect the pedigrees were used to identify the best pedigree representation of the mutation carriers of the novel tandem duplication in LDLR (Maxwell et al. (2017). Profiling copy number variation and disease associations from 50,726 DiscovEHR Study exomes). HumanOmniExpress array data were previously used to estimate the more distant relationships.

Example 15

SimProgeny

SimProgeny can simulate populations of millions of people dispersed across one or more sub-populations and track their decedents over hundreds of years. To find a good balance between simplistic and realistic, several key population level parameters were selected that can be adjusted by the user (See Table 23 below). These parameters were selected to provide a good approximation of a real population and familial pedigree structures while keeping the simulation tool relatively simple. Default values are based on US population statistics. The default values had been set to work for the both the cohorts, and these parameters could be easily customized to model different populations by modifying the configuration file included with the SimProgeny code (web resource). See Example 17 for a detailed description of the population simulation process.

TABLE 23

(Simulation parameters and default values used in SimProgeny)

| Parameter | Description | Default value |
| --- | --- | --- |
| Birth rate | Births per person per year | 0.0219 |
| Death rate | Deaths per person per year | 0.0095 |
| Marriage rate | Marriages per person per year | 0.01168 |
| Divorce rate | Divorces per person per year | 0.0028 |
| Full-sibling rate | Proportion of births to married couples | 0.88 |
| Fertility start | Youngest age an individual can reproduce | 15 |
| Fertility end | Oldest age an individual can reproduce | 49 or 50 |
| in-migration rate | Proportion of annual in-migrating | 0.01 |
| out-migration rate | Proportion of annual out-migrating each year | 0.021 |
| Fertility by age | Weighting vector for women ages 0 to 50 | ranges 0 to 1 |
| Male mortality by age | Weighting vector for men ages 0 to 120 | ranges 0 to 1 |
| Female mortality by age | Weigthing vector for women ages 0 to 120 | ranges 0 to 1 |
| Male marriage by age | Weighting vector for men ages 0 to 50 | ranges 0 to 1 |

TABLE 23-continued (Simulation parameters and default values used in SimProgeny)

| Parameter | Description | Default value |
|---|---|---|
| Female marriage by age | Weighting vector for women ages 0 to 50 | ranges 0 to 1 |

For the framework developed set for DiscovEHR cohort, the fertility end was 49 years and for framework developed set for expanded DiscovEHR cohort, the fertility end was 50 years.

In addition to modeling populations, SimProgeny simulates two ascertainment approaches to model selecting individuals from a population for a genetic study: random ascertainment and clustered sampling. Random ascertainment gives each individual in the population an equal chance of being ascertained without replacement. Clustered sampling is an approach to enrich for close relatives, and it is done by selecting an individual at random along with a number of their first- and second-degree relatives. The number of first-degree relatives is determined by sampling a value from a Poisson distributed with a user specified first-degree ascertainment lambda (default is 0.2). The number of second-degree relatives is determined in the same way and the default second-degree ascertainment lambda is 0.03. See Example 17 for additional information on SimProgeny's ascertainment options.

Example 16

Simulation of the Underlying DiscovEHR Population and its Ascertainment

In an effort to not over complicate the simulation model, the simulations contained individual populations with starting sizes of 200K, 300K, 400K, 450K, 500K, 550K, 600K, and 1000K. SimProgeny parameters (See Table 23 above) were tuned with publicly available country, state, and county level data as well as our own understanding of how individuals were ascertained through GHS. Sources for the selected parameters are available in supplementary file Simulation_parameters.xls. The immigration and emigration rates from the Pennsylvania (PA) average were reduced since GHS primarily serves rural areas, which tend to have lower migration rates than more urban areas. Simulations were run with a burn-in period of 120 years and then progressed for 101 years. Simulated populations grew by ~15%, which is similar to the growth of PA since the mid-20th century.

Both random and clustered ascertainment was performed. For both ascertainment approaches, the ascertainment order of the first 5% of the population (specified with the ordered-_sampling_proportion parameter) was shuffled in order to model the random sequencing order of the individuals in GHS biobank at the beginning of the collaboration. While the selection of this parameter has no effect on random ascertainment and a negligible effect on the accumulation of pairwise relationships in clustered ascertainment, it does affect the proportion of individuals with one or more relatives in the dataset that were ascertained with clustered sampling by causing an inflection point, which is more pronounced with higher lambda values. This inflection point would be less pronounced if we were to model the freeze process of the real data or model a smoother transition between sequencing samples from the biobank and newly ascertained individuals.

Example 17

SimProgeny Population and Ascertainment Simulation Process

The simulation began by initializing the user specified number of sub-populations and sizes. Ages were initially assigned between zero and the maximum fertile age (default was 49). Individuals in a population resided in one of three age-based pools: juveniles, fertile, or aged. Individuals were assigned to the sub-population's juvenile pool if they are under the fertility age (default of 15) or assigned to the sub-population's mating pool if within the fertility age range (15 to 49 by default). Individuals were moved from the juvenile pool to the mating pool as they aged above the minimum fertile age. Similarly, they were moved from the mating pool to the aged poll once they aged beyond the max fertile age. Individuals were removed from all age pools if they emigrated or passed away. After establishing an initial population, the simulation performed a burn-in phase of 120 years to establish family relationships and an age distribution that more closely matched the input parameters while requiring equal numbers of births and deaths and a net migration rate of zero. After burn-in, the simulations ran for a specified number of years with the provided population growth and migration rates. The simulations progressed at one-year increments and each year had the following steps that were performed within each sub-population, unless otherwise stated:

1. Age—move individuals who have aged out of their age pool to the next age pool.
2. Court—simulate a single man and a single woman entering into a monogamous marriage. This process is important to obtain a realistic number of full-sibling relationships. Pairs of men and women are chosen at random from the pool of single reproductive aged males and females, and they successfully marry based on their chances of getting married at their age, which are specified by the male and female "marriage by age" parameters. Pairs are drawn until the number of successful marriages is reached as defined by the marriage rate. Couples are restricted to being more distantly related than first-cousins. During the burn-in phase, the marriage rate is double until the user specified initial marriage rate is reached (default is 66% of the fertile pool being married).
3. Split—simulate a man and a woman breaking a marriage at the specified divorce rate. Couples are chosen at random and both individuals are marked as single.
4. Mingle—simulate all of the reproduction that may take place within a population for one year. Mother/father pairs are chosen at random from either the single reproductive age pool or the married pool in a ratio defined by the full-sibling rate (default is 88% of all births being to married couples). Pairs are drawn and reproduction attempts are made until the target number of successful conceptions is reached (default birthrate is 0.0219 births per person). The chances a successful conception occurs is based on the prospective mother's age and corresponding fertility rate. Parents are restricted to being more distantly related than first cousins, and all individuals are limited to having one child per year.
5. Cull—simulate individuals passing away. The death rate (default is 0.0095 deaths per person) is used to determine the expected number of deaths within the population in a given year. The male and female mortality by age parameters are used to weight the chance a randomly selected individual will pass away. If the random number between 0 and 1 exceeds the person's probability of dying at his/her age, then the individual is retained and another individual is selected. Unfortunate individuals are added to the departed pool and removed from any other pools of the living. All individuals who are older than 120 are automatically added to the departed pool and count towards the target number of deaths for the year.

6. Migrate—simulate migration to and from the population. Emigration is performed by randomly selecting an individual from the mating pool and removing him/her from the population along with his/her spouse if married and of a fertile age. The proportion of juvenile and aged individuals leaving is recorded along with the number of fertile aged married couples. Immigration is done in a way to maintain the age distributions and the number of fertile aged married couples. First, a juvenile is randomly selected from the existing population and a new individual of the same sex and age is added to the juveniles pool, and this process is repeated until the appropriate proportion of juveniles have been added. The same process is repeated for aged individuals. Next, two fertile aged individuals are selected from the existing population, and two new individuals are added with corresponding ages. One is assigned to be male and the other female, and the two immigrants are then married. This step is repeated until the number of married couples has been replenished. Finally, fertile aged individuals are added in the same process used to add new juveniles, and it is repeated until the target number of immigrants is achieved. This process helps maintain the population's age and sex distributions as well as the proportion of married fertile aged individuals.

7. Transplant—simulate people moving within sub-populations. To simulate the lack of genetic isolation between sub-populations, individuals can move between sub-populations within the overall population. A single rate of movement is used across the entire population. Individuals from a sub-population are selected at random and assigned at random to one of the other sub-populations until the desired number of transplants are achieved. This step does not occur if there is only one sub-population or if the transplant rate is 0 (default is 1% of the overall population transplants each year).

The simulation progresses for the specified length of time keeping track of each founder and their descendants.

Both random and clustered ascertainment was performed. For both ascertainment approaches, the ascertainment order of the first 5% of the population (specified with the ordered_sampling_proportion parameter) was shuffled in order model the random sequencing order of the individuals in GHS biobank at the beginning of our collaboration. While the selection of this parameter had no effect on random ascertainment and a negligible effect on the accumulation of pairwise relationships in clustered ascertainment, it did affect the proportion of individuals with one or more relatives in the dataset that were ascertained with clustered sampling by causing an inflection point, which was more pronounced with higher lambda values. This inflection point would have been less pronounced if one were to model the freeze process of the real data or model a smoother transition between sequencing samples from the biobank and new ascertained individuals. Users could specify the sub-population ascertainment order in the case they want to simulate ascertaining from one or more sub-populations before moving onto the next set of sub-populations. The default was to initially group all subpopulations and ascertain from them as if they had been a single population. Users could also specify the initial proportion of a population that was ascertained before moving onto other sub-populations or the overall population. The program established an output for the entire population in ped file format, the list of ascertained samples in the order they were ascertained, and several results files summarizing useful population and ascertainment statistics.

Example 18

Methods that use pedigree structures to aid in identifying the genetic cause of a given phenotype typically involve innovative variations on association mapping, linkage analysis, or both. Such methods include MORGAN31, pVAAST15, FBAT (www.hsph.harvard.edu/fbat/fbat.htm), QTDT (csg.sph.umich.edu/abecasis/qtdt/), ROADTRIPS, rareIBD, and RV-GDT. The appropriate method to use depends on the phenotype, mode of inheritance, ancestral background, pedigree structure/size, number of pedigrees, and size of the unrelated dataset. In addition to using the relationships and pedigrees to directly interrogate gene-phenotype associations, they can also be used in a number of other ways to generate additional or improved data: pedigree-aware imputation, pedigree-aware phasing, Mendelian error checking, compound heterozygous knockout detection and de novo mutation calling, and variant calling validation.

The disclosure is not limited to the exemplary embodiments described and exemplified above, but is capable of variation and modification within the scope of the appended claims.

What is claimed is:

1. A method for phasing genetic variants in a population by leveraging the population's relatedness, comprising:
    establishing an ancestral superclass designation for each of one or more of the samples,
    generating first identity-by-descent estimates of subjects within an ancestral superclass,
    generating second identity-by-descent estimates of subjects independent from subjects' ancestral superclass,
    clustering subjects into primary first-degree family networks based on one or more of the second identity-by-descent estimates,
    generating third identity-by-descent estimates of subjects within a primary first-degree family network,
    merging first and third identity-by-descent estimates to obtain merged identity-by-descent estimates,
    constructing secondary first-degree family networks of samples based on merged identity-by-descent estimates, and
    phasing variants in accordance with merged identity-by-descent estimates and secondary first-degree family networks as being or not being a compound heterozygous mutation (CHM), or identifying variants in accordance with merged identity-by-descent estimates and secondary first-degree family networks as a de novo mutation (DNM).

2. The method according to claim 1, wherein merging first and third identity-by-descent estimates comprises augmenting the first identity-by-descent estimates with pairwise identity-by-descent estimates unique to the third identity-by-descent estimates.

3. The method according to claim 1, wherein phasing variants as a compound heterozygous mutation (CHM) comprises:
phasing variants according to population allele frequencies,
removing variants outside of Hardy-Weinberg equilibrium (HWE) or within 10 base pairs of another variant in the same sample or both; and
removing SNPs with a quality by depth (QD) of about 2 or less, or a read depth (DP) of less than about 5, or an alternate allele balance (AB) of about 10% or less, or a combination thereof; and removing insertions or deletions (INDELS) with a QD of about 2 or less, or a DP of less than about 5, or an AB of about 10% or less, or a combination thereof,
selecting remaining variants as potential compound heterozygous mutations (pCHMs) where there are one or more pairs of variants in the same sample and in the same gene, and
phasing pCHMs as either cis or trans pCHMs, and then classifying the pCHM phased as trans pCHM as CHM.

4. The method according to claim 3, wherein phasing variants as a compound heterozygous mutation comprises:
removing variants outside of Hardy-Weinberg equilibrium (HWE) or within 10 base pairs of another variant in the same sample or both; and removing SNPs with a quality by depth (QD) of about 3 or less, or a read depth (DP) of less than about 7, or an alternate allele balance (AB) of about 15% or less, or a combination thereof; and removing insertions or deletions (INDELS) with a QD of about 5 or less, or a DP of less than about 10, or an AB of about 20% or less, or a combination thereof.

5. The method according to claim 3, further comprising:
scoring CHMs according to phenotype severity, and
selecting CHMs having the highest phenotype severity score per gene per sample, such that when the human has more than one CHM in the same gene, the CHM most likely to result in protein function inhibition is identified.

6. The method according to claim 1, wherein phasing variants as a de novo mutation comprises:
identifying variants in samples in secondary first-degree family networks and trios thereof,
assigning genotype likelihood scores to variants in parent samples and corresponding child sample in a trio and calculating a probability that the variant is a de novo mutation, and identifying the variant as a probable de novo mutation when the calculated probability is statistically significant,
identifying a variant in a child sample in a trio and identifying the variant as a probable de novo mutation when the variant is not present in either parent sample in the trio,
filtering probable de novo mutations identified by removing probable de novo mutations having a genotype quality (GQ) annotation in the child sample of less than about 35, or having an alternate allele count (AC) of 10 or greater across the samples, or having a read depth (DP) of less than about 7 and an alternate DP of less than about 4 in the child sample, or having an allele balance (AB) in either parent sample of greater than about 2%, or having an allele balance (AB) of less than about 15% in the child sample, or having an AB of greater than about 90% in the child sample, or having alternate allele homozygosity in either parent sample, or a combination thereof, and
combining filtered probable de novo mutations identified, thereby forming a probable de novo mutation dataset.

7. The method according to claim 6, further comprising:
classifying a probable de novo mutation in the probable de novo mutation dataset as a moderate confidence de novo mutation when the probable de novo mutation has an allele balance of about 0.15 or greater in the child sample and about 0.02 or less in each parent sample, and does not have a mapping quality of less than about 40, and does not have a quality by depth (QD) value of less than about 2, and has MAC of less than about 20 across the samples, and has about 3 soft-clipped reads or less at the variant site in the carrier of the probable de novo mutation, and is not an INDEL with a monopolymer run of more than about 4.

8. The method according to claim 7, further comprising:
classifying a moderate confidence de novo mutation as a high confidence de novo mutation when the moderate confidence de novo mutation has a genotype quality annotation in the parent sample of about 90 or greater, and has a read depth of about 10 or greater in each parent sample, and has an alternate read depth of about 7 or greater in the child sample, and has QD greater than about 3 for SNPs, and has QD greater than about 5 for INDELs.

9. The method according to claim 1, further comprising removing low-quality samples from the dataset, wherein the low-quality samples are samples having a D-stat of >0.12 or 20× read coverage of <75%, or both.

10. A system, comprising:
a data processor; a memory coupled with the data processor; and a program stored in the memory, the program including instructions for:
identifying variants in DNA sequence samples from a plurality of human subjects;
establishing an ancestral superclass designation for subjects based on identified variants;
generating first identity-by-descent estimates of subjects within an ancestral superclass;
generating second identity-by-descent estimates of subjects independent from subjects' ancestral superclass;
clustering subjects into primary first-degree family networks based on one or more of the second identity-by-descent estimates;
generating third identity-by-descent estimates of subjects within a primary first-degree family network;
merging first and third identity-by-descent estimates to obtain merged identity-by-descent estimates;
constructing secondary first-degree family networks based on merged identity-by-descent estimates;
phasing variants in samples according to population-allele frequencies;
classifying a phased variant as a potential compound heterozygous mutation ("CHM") based on the presence of two or more variants in the same subject and gene; and
phasing a potential CHM as cis or trans with another variant in the same subject and gene, and then classifying the potential CHM phased as trans as CHM.

11. The system of claim 10, wherein the program includes instructions for filtering identified variants before ancestral superclass designations for subjects are established.

12. The system of claim 10, wherein the program includes instructions for filtering identified variants before second identity-by-descent estimates of subjects are generated.

13. The system of any one of claim 10, wherein filtering variants comprises removing variants having alternate allele frequency greater than about 10% across the samples from the plurality of human subjects, or variants violating Hardy-Weinberg equilibrium (HWE) with a p-value >about 10-6, or variants having missing calls in >about 5% of the samples from the plurality of human subjects, or a combination thereof.

14. The system of any one of claim 11, wherein the program includes instructions for removing low-quality samples after identified variants have been filtered.

15. The system of claim 14, wherein low-quality samples are samples having a D-stat of >0.12 or 20× read coverage of <75%, or both.

16. The system of any one of claim 10, wherein merging first and third identity-by-descent estimates comprises augmenting the first identity-by-descent estimates with pairwise identity-by-descent estimates unique to the third identity-by-descent estimates.

17. A system, comprising:
  a data processor; a memory coupled with the data processor; and a program stored in the memory, the program including instructions for:
  identifying variants in DNA sequence samples from a plurality of human subjects;
  establishing an ancestral superclass designation for subjects based on identified variants;
  generating first identity-by-descent estimates of subjects within an ancestral superclass;
  generating second identity-by-descent estimates of subjects independent from subjects' ancestral superclass;
  clustering subjects into primary first-degree family networks based on one or more of the second identity-by-descent estimates;
  generating third identity-by-descent estimates of subjects within a primary first-degree family network;
  merging first and third identity-by-descent estimates to obtain merged identity-by-descent estimates;
  constructing nuclear families based on merged identity-by-descent estimates;
  identifying variants in nuclear families;
  assigning a genotype likelihood score to a variant in samples from each parent and child in a trio in a constructed nuclear family and calculating a probability that the variant is a de novo mutation, and selecting the variants with a significantly high probability that the variant is a de novo mutation, and independently naively identifying a called variant in a child sample that is not called in either parent sample in a trio, and then combining the two sets of de novo mutations, thereby forming a dataset of probable de novo mutations.

18. The system of claim 17, wherein the program includes instructions for filtering identified variants before ancestral superclass designations for subjects are established.

19. The system of claim 17, wherein the program includes instructions for filtering identified variants before second identity-by-descent estimates of subjects are generated.

20. The system of claim 18, wherein filtering variants comprises removing variants having alternate allele frequency greater than about 10% across the samples from the plurality of human subjects, or variants violating Hardy-Weinberg equilibrium (HWE) with a p-value >about 10-6, or variants having missing calls in >about 5% of the samples from the plurality of human subjects, or a combination thereof.

* * * * *